United States Patent
Gee et al.

(10) Patent No.: US 10,648,985 B2
(45) Date of Patent: May 12, 2020

(54) COMPOUNDS AND METHODS FOR CONJUGATION OF BIOMOLECULES

(71) Applicant: LIFE TECHNOLOGIES CORPORATION, Carlsbad, CA (US)

(72) Inventors: Kyle Gee, Springfield, OR (US); Upinder Singh, San Marcos, CA (US); Scott Grecian, Jasper, OR (US); Scott Clarke, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 16/107,762

(22) Filed: Aug. 21, 2018

(65) Prior Publication Data
US 2019/0079095 A1   Mar. 14, 2019

Related U.S. Application Data

(63) Continuation of application No. 14/000,819, filed as application No. PCT/US2012/027285 on Mar. 6, 2014, now abandoned.

(60) Provisional application No. 61/558,148, filed on Nov. 10, 2011, provisional application No. 61/449,396, filed on Mar. 4, 2011.

(51) Int. Cl.
| | |
|---|---|
| *C07D 213/46* | (2006.01) |
| *G01N 33/58* | (2006.01) |
| *G01N 33/533* | (2006.01) |
| *C07D 213/74* | (2006.01) |
| *C07D 213/79* | (2006.01) |
| *C07D 213/81* | (2006.01) |
| *C07D 215/12* | (2006.01) |
| *C07D 401/04* | (2006.01) |
| *C07D 235/14* | (2006.01) |
| *C07D 213/53* | (2006.01) |
| *C07D 213/68* | (2006.01) |
| *C07D 213/78* | (2006.01) |
| *C09B 23/06* | (2006.01) |
| *C09B 23/08* | (2006.01) |
| *C09B 11/24* | (2006.01) |
| *C07D 401/14* | (2006.01) |
| *C07K 14/575* | (2006.01) |

(52) U.S. Cl.
CPC ......... *G01N 33/582* (2013.01); *C07D 213/53* (2013.01); *C07D 213/68* (2013.01); *C07D 213/74* (2013.01); *C07D 213/78* (2013.01); *C07D 213/79* (2013.01); *C07D 213/81* (2013.01); *C07D 215/12* (2013.01); *C07D 235/14* (2013.01); *C07D 401/04* (2013.01); *C07D 401/14* (2013.01); *C07K 14/575* (2013.01); *C09B 11/24* (2013.01); *C09B 23/06* (2013.01); *C09B 23/083* (2013.01); *G01N 33/533* (2013.01)

(58) Field of Classification Search
CPC .......................... C07D 401/14; C07D 491/147
USPC ...... 546/274.4, 48, 316, 282.7, 277.4, 273.1
See application file for complete search history.

(56) References Cited

U.S. PATENT DOCUMENTS

| | | | |
|---|---|---|---|
| 6,207,671 B1 | 3/2001 | Schmidt et al. | |
| 2010/0016373 A1* | 1/2010 | Khilevich et al. | ........................... A61K 31/4439 514/341 |
| 2011/0190254 A1* | 8/2011 | Nishitani et al. | .... A61K 31/546 514/202 |

FOREIGN PATENT DOCUMENTS

| | | |
|---|---|---|
| WO | WO-2006116736 A2 | 11/2006 |
| WO | WO-2010009062 A1 | 1/2010 |
| WO | WO-2013025883 A1 | 2/2013 |

OTHER PUBLICATIONS

Guthikonda, R. N. et al.: Structure-activity relationships in the 2-arylcarbapenem series: synthesis of 1-methyl-2-arylcarbapenems. J. Med. Chem., vol. 30, pp. 871-880, 1987.*
Lee, J. et al.: Analysis of structure-activity relationships for the A-region of N-(4-t-butylbenzyl)-N'[4-(methylsulfonylamino)benzyl] thiourea analogues as TRPV 1 antagonists. Bioorganic & Medicinal Chem. Lett., vol. 15, pp. 4136-4142, 2005.*
12710600.3, , "Examination Report", 2014, 4 pages.
Buurman, ET. et al. Pyridines and Pyrimidines Mediating Activity against an Efflux-Strain of Candida albicans through Putative Inhibition of Lanosterol Demethylase. Antimicrobial Agents and Chemotherapy. 2004, vol. 48, p. 315.
Carey, FA. Organic Chemistry 6th Ed. McGraw Hill. 2006, chapter 1, p. 9.
Constable, Edwin C. et al., "First example of a CLICK reaction of a coordinated 4'-azido-2,2':6',2"-terpyridine ligand", Inorganic Chemistry Communications 13, 2010, 495-497.
Diaz, Philippe et al., "New Selenium-Containing Acetylenic Retinoids by Direct Coupling of Alkynylsilanes with Selenylhalides", Tetrahedron Letters, 39, Dec. 3, 1998, XP004140988, pp. 9003-9006.
Durot, Stephanie et al., "Synthesis of new copper(I)-complexed rotaxanes via click chemistry", Tetrahedron, 64, 2008, 8496-8503.
Extended European Search Report for Application No. 15178237.2, dated Oct. 14, 2015, 7 pages.

(Continued)

*Primary Examiner* — Charanjit Aulakh

(57) ABSTRACT

Low-copper click chemistry, 1.3-dipolar cycloadditions, and Staudinger ligations for modifying biomolecules is provided. Compositions, methods, and kits relating to low-copper click chemistry, 1.3-dipolar cycloadditions, and Staudinger ligations are also provided.

14 Claims, 24 Drawing Sheets

(56) References Cited

OTHER PUBLICATIONS

Glasnov, T. et al., "Microwave-Assisted Click Chemistry for the Preparation of 3- and 4-Triazolyl-2 (1H)-quinolones as Potential Fluorescent Probes", QSAR & Combinatorial Science, Wiley-VCH Verlag, vol. 26, No. 11-12, 2007, pp. 1261-1265.

Gui-Chao Kuang et al: "Chelation-Assisted, Copper(II)-Acetate-Accelerated Azide-Alkyne Cycloaddition", The Journal of Organic Chemistry, vol. 75, No. 19, Oct. 1, 2010 (Oct. 1, 2010), pp. 6540-6548, XP055026461, ISSN: 0022-3263, DOI: 10.1021/jo101305m.

Gupta, Sayam S. et al., "Accelerated Bioorthogonal Conjugation: A Practical Method for the Ligation of Diverse Functional Molecules to a Polyvalent Virus Scaffold", Bioconjugate Chemistrv. vol. 16, No. 6, 2005, 1572-1579.

Jain, Pooja et al., "Nicotinic Acid Adenine Dinucleotide Phosphate Analogues Containing Substituted Nicotinic Acid: Effect of Modification on Ca2+ Release", J. Med. Chem., 53, 2010, 7599-7612.

Lee, Jeewoo et al., "Analysis of structure-activity relationships for the 'A-region' of N-(4-tbutylbenzyi)-N'-[4-(methylsulfonylamino) benzyl] thiourea analogues as TRPV1 antagonists", 2005, vol. 15, 4136-4142.

Morten Meldal et al: "Cu-Catalyzed Azide-Alkyne Cycloaddition", Chemical Reviews, American Chemical Society, US, vol. 108, No. 8, Jan. 1, 2008 (Jan. 1, 2008), pp. 2952-3015, XP008136168, ISSN: 0009-2665, DOI: 10.1021/CR0783479 [retrieved on Aug. 13, 2008].

Nungaray J., et al., "Wave Chemistry: 2-(4'-Azido 3',5',6'-trifluoro 2'-Pyridyl)-Amino Ethylamine as a Key Photoactivatable Building Block with Wide Biological Applications", Synthetic Communications, 1996, vol. 26, No. 7, pp. 1273-1287.

PCT/US2012/027285 "International Search Report and Written Opinion", 2012, 20 pgs.

Sletten, J. , "Copper (II) Complex of the Tripodal Ligand Tris ((benzimidazol-2-yl)methyl)amine and its Bonding to a Sulfur Ligand of Thiolate Character", Acta Chemica Scandinavica, 1997, 822-831.

Tobey, Suzanne et al., "Energetics of Phosphate Binding to Ammonium and Guanidinium Containing Metallo-Receptors in Water", J. Am. Chem. Soc., 125, 2003, 14807-14815.

Tsuritani, Taka Yuki et al., "Efficient Synthesis of 1,4-Diaryl-5-methyl-1,2,3-triazole, A Potential mGiuR1 Antagonist, and the Risk Assessment Study of Arylazides", Organic Process Research & Development 13, 2009, 1407-1412.

Urankar, Damijana et al., "Concise and Diversity-Oriented Synthesis of Ligand Arm-Functionalized Azoamides", J. Comb. Chem., 10, 2008, 981-985.

Wu, H. , "A five-coordinate copper(II) perchlorate complex with tris(N-methylbenzimidazol-2-ylmethyl)amine and salicylate", Journal of Coordination Chemistry (Impact Factor: 2.01).(Abstract), 62(21 ), 2009, 3446-3453.

* cited by examiner

COMPOUNDS AND METHODS FOR CONJUGATION OF BIOMOLECULES

RELATED APPLICATIONS

This application is a continuation of U.S. Nonprovisional application Ser. No. 14/000,819, filed Mar. 6, 2014, which application is a 371 application of International Application No. PCT/US2012/027285, filed Mar. 1, 2012, which claims the benefit of priority to U.S. Provisional Application No. 61/558,148, filed Nov. 10, 2011, and U.S. Provisional Application No. 61/449,396, filed Mar. 4, 2011, which disclosures are herein incorporated by reference in their entirety.

FIELD

This invention relates to click chemistry, 1,3-dipolar cycloadditions, and Staudinger ligations for conjugating biomolecules.

BACKGROUND

Conjugation of biomolecules, such as polynucleotides, proteins, lipids, etc., can be useful for detection, isolation, and/or identification of biomolecules. Click chemistry was developed by K. Barry Sharpless as a robust and specific method of ligating two molecules together. See, e.g., Kolb et al. *Angew. Chemie Intern.* 40(11): 2004-21 (2001). Classic click reactions typically require Cu(I) ions in order to proceed efficiently. However, Cu(I) ions can have deleterious effects on cells and biomolecules. Reducing the amount and/or accessibility of Cu(I) ions used in click reactions could therefore be beneficial for conjugating biomolecules.

SUMMARY

In one aspect, the invention provides a compound of the formula:

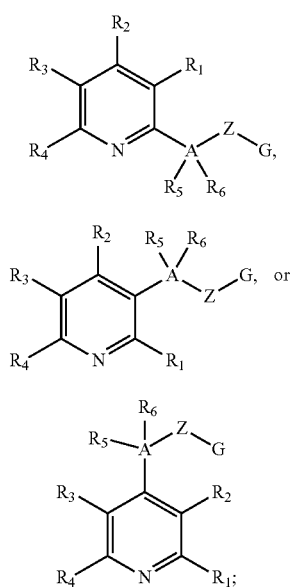

wherein:
A is a carbon, or A, $R_5$, and $R_6$ are absent;
$R_1$, $R_2$, $R_3$, and $R_4$, are independently selected from hydrogen, halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_1$, $R_2$, $R_3$, and $R_4$, wherein each of the at least two substituents are on different carbon atoms together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or at least two of the remaining substituents together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and any remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;
$R_5$, and $R_6$, are independently selected from hydrogen, halogen, —$SO_3X$, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido;
at least one substituent selected from $R_1$, $R_2$, $R_3$, $R_4$, $R_5$ and $R_6$ comprises X-L-, wherein:
X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl chain; and G is a chemical handle selected from an azide-reactive group, an alkyne-reactive group, and a phosphine-reactive group.

In some embodiments, the compound is of the formula (I). In some of these, the compound is of the formula:

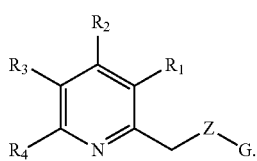

(IV)

In others, the compound is of the formula:

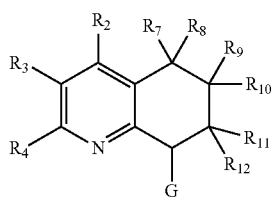

(XIII)

wherein $R_2$, $R_3$, $R_4$, and $R_7$ to $R_{12}$ are independently selected from hydrogen, halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_2$, $R_3$, $R_4$, and $R_7$ to $R_{12}$, wherein the two substituents are on different carbon atoms together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two of the remaining substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or $R_7$ to $R_{12}$, wherein the two substituents are on same carbon atom together form a spirocyclic moiety selected from alkyl or hetertoalkyl, portions of which are further optionally substituted with halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

at least one substituent selected from $R_1$, $R_2$, $R_3$, $R_4$, $R_5$ and $R_6$ comprises X-L-, wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl; and G is a chemical handle selected from an azide-reactive group, an alkyne-reactive group, and a phosphine-reactive group.

In some embodiments, the compound of the formula (I), (II) or (III) is selected from the group consisting of:

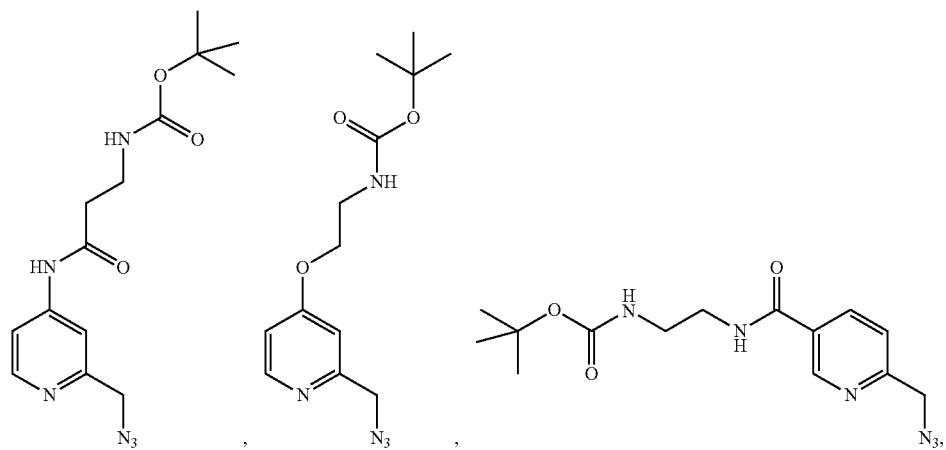
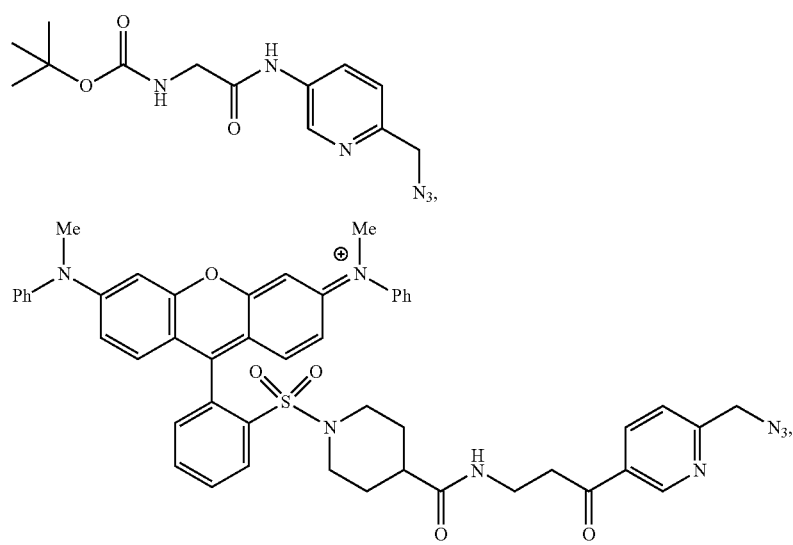
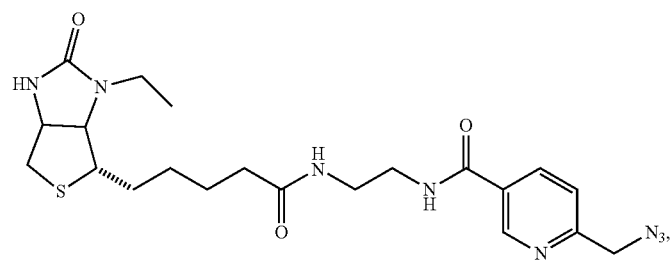
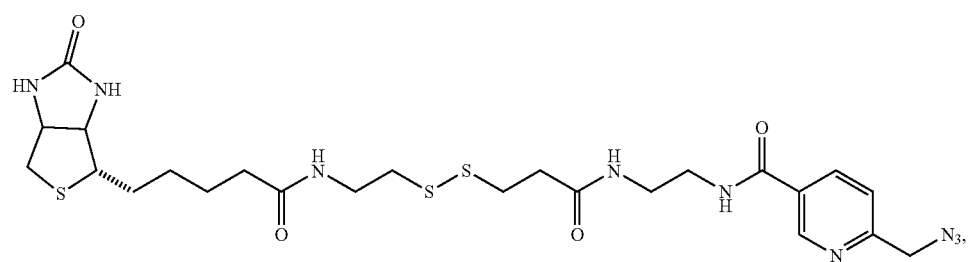

-continued
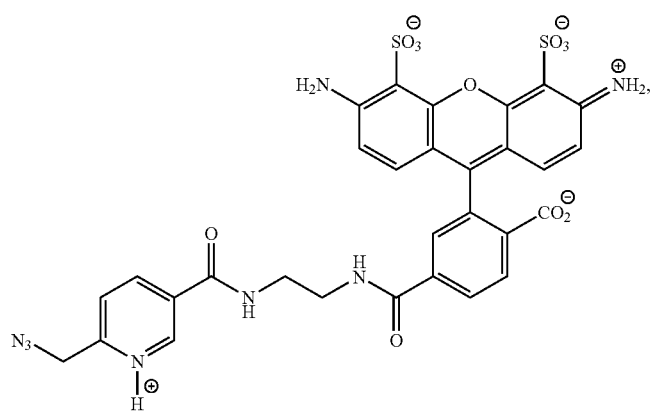
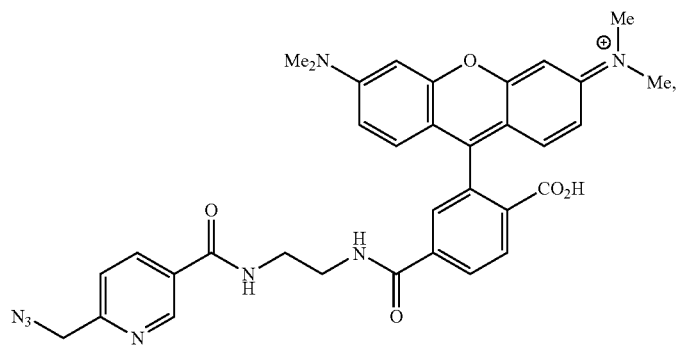
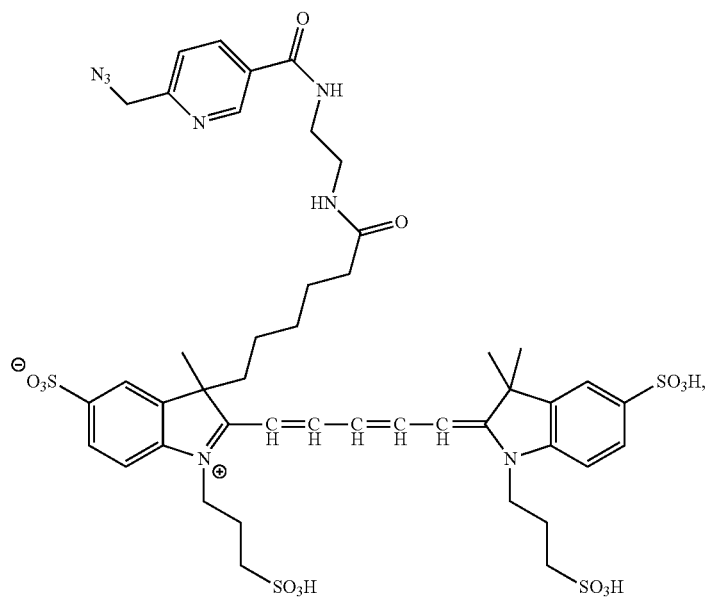

-continued

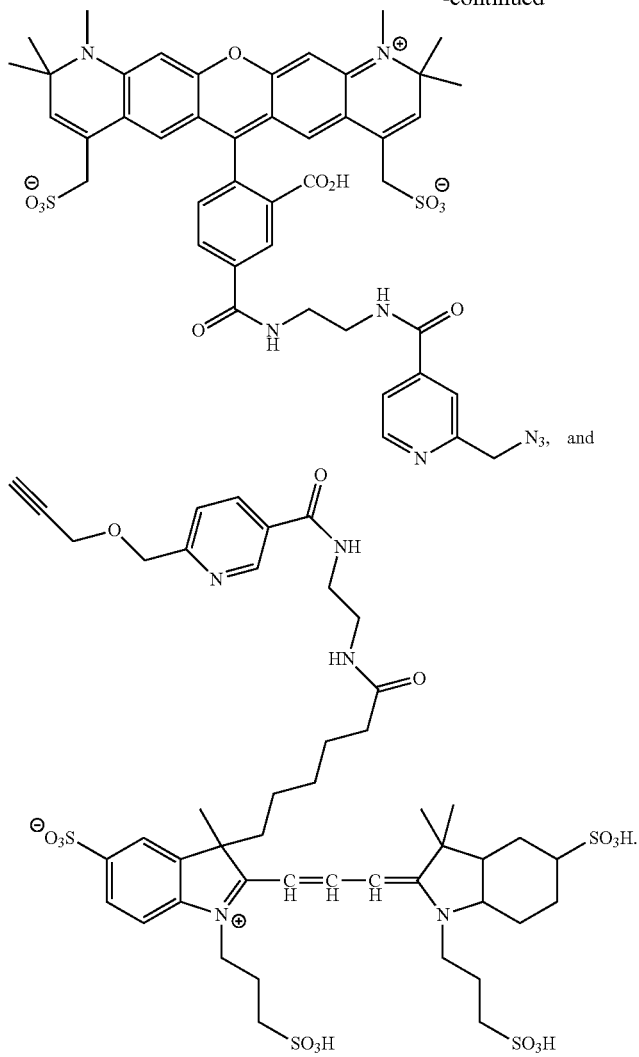

and

In another aspect, the invention provides a compound of the formula:

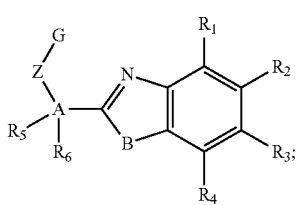

wherein:

$R_1$, $R_2$, $R_3$, and $R_4$ are independently selected from hydrogen, halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_1$, $R_2$, $R_3$, and $R_4$ together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining two substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, or the remaining two substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

R$_5$, and R$_6$, are independently selected from hydrogen, —SO$_3$X, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —SO$_3$X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or at least one substituent selected from R$_1$, R$_2$, R$_3$, R$_4$, R$_5$, and R$_6$ comprises X-L-, wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

A is a carbon, and R$_5$ and R$_6$ are independently selected from hydrogen, halogen, —SO$_3$X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —SO$_3$X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido or A, R$_5$, and R$_6$ are absent;

B is selected from O, S, and NR$_7$, wherein R$_7$ is selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl and X-L wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl chain; and G is a chemical handle selected from an azide-reactive group, an alkyne-reactive group, and a phosphine-reactive group.

In another aspect, the invention provides a compound of the formula:

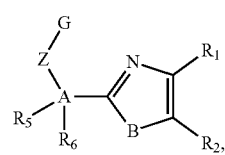

(VI)

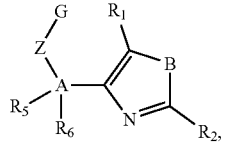

(VII)

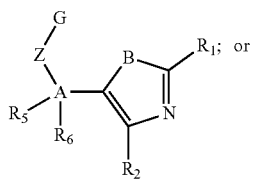

(VIII)

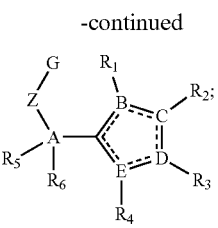

(XIV)

wherein:

A is a carbon, or A, R$_5$, and R$_6$ are absent;

R$_1$, R$_2$, R$_3$ and R$_4$ are independently selected from hydrogen, halogen, —SO$_3$X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl arylcarboxamido, alkyl and aryl portions are optionally substituted one or more times by halogen, —SO$_3$X, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido;

R$_5$, and R$_6$, are independently selected from hydrogen, —SO$_3$X, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —SO$_3$X, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from R$_1$, R$_2$, R$_3$, and R$_4$, wherein the two substituents are on different carbon atoms together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or at least one substituent selected from R$_1$, R$_2$, R$_3$, R$_4$, R$_5$, and R$_6$ comprises X-L-, wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

B, C, D and E are selected from O, S, and N where N is further substituted with either R$_7$, R$_8$ or R$_9$, wherein R$_7$, R$_8$ or R$_9$ are selected from hydrogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, substituted heteroaryl and X-L wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments, the compound is of formula (VI), and R$_1$, R$_2$, R$_3$, and R$_4$, are independently selected from hydrogen, halogen, —SO$_3$X, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, llkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or $R_1$ and $R_2$, $R_2$ and $R_3$, $R_3$ and $R_4$ together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and $R_5$ and $R_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl.

One embodiment is the compound:

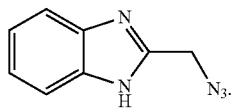 [SMILES: [N-]=[N+]=NCc1nc2ccccc2[nH]1]

In another aspect, the invention provides a compound of the formula:

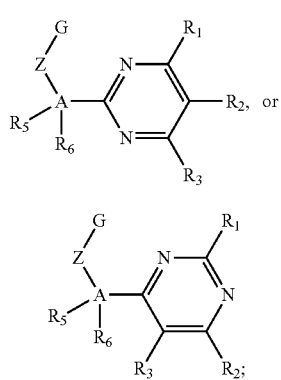

wherein:

A is a carbon, or A, $R_5$, and $R_6$ are absent;

$R_1$, $R_2$, and $R_3$ are independently selected from hydrogen, halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido;

$R_5$, and $R_6$, are independently selected from hydrogen, halogen, —$SO_3X$, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_1$, $R_2$, $R_3$, $R_5$, and $R_6$, wherein the two substituents are on different carbon atoms, together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

at least one substituent selected from $R_1$, $R_2$, $R_3$, $R_5$, and $R_6$ comprises X-L-, wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl having a chain length of 1-10 atoms, or is absent; and G is a chemical handle selected from an azide-reactive group, an alkyne-reactive group, and a phosphine-reactive group.

In another aspect, the invention provides a compound of the formula:

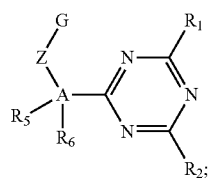

(XI)

wherein:

A is a carbon, or A, $R_5$, and $R_6$ are absent;

$R_1$, and $R_2$ are independently selected from hydrogen, halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, alkylthio, alkanoylamino, alkylaminocarbonyl, substituted alkoxy, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido;

$R_5$, and $R_6$, are independently selected from hydrogen, —$SO_3X$, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or at least one substituent selected from $R_1$, $R_2$, $R_5$, and $R_6$ comprises X-L-, wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl having a chain length of 1-10 atoms, or is absent; and G is a chemical handle selected from an azide-reactive group, an alkyne-reactive group, and a phosphine-reactive group.

In another aspect, the invention provides a compound of the formula:

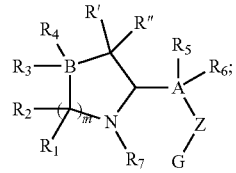

(XII)

wherein:

A is a carbon, or A, $R_5$, and $R_6$ are absent;

m and n is an integer between 1 and 4;

B is O or S and $R_3$ and $R_4$ are absent or N and $R_3$ or $R_4$ is absent;

$R_7$ is selected from hydrogen, alkyl, heteroalkyl, substituted alkyl, and substituted heteroalkyl;

$R_1$, $R_2$, $R_3$, $R_4$, each R', and each R" are independently selected from hydrogen, halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_1$, $R_2$, $R_3$, $R_4$, an R', and an R", wherein the two substituents are on different carbon atoms together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two of the remaining substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

wherein, $R_5$, and $R_6$, are independently selected from hydrogen, —$SO_3X$, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or at least one substituent selected from $R_1$, $R_2$, $R_3$, $R_4$, $R_5$, $R_6$, an R', and an R" comprises X-L-, wherein:

X is selected from a reporter molecule, a carrier molecule, a solid phase, or a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments of the compound of the formula (I), (II), (III), (IV), (XIII), (V), (VI), (VII), (VIII), (XIV), (IX), (X), (XI) or (XII), all but one of the R substituents are H.

In some embodiments of the compound of the formula (I), (II), (III), (IV), (XIII), (V), (VI), (VII), (VIII), (XIV), (IX), (X), (XI) or (XII), L is an alkyl group having a chain length of 0 to 15 atoms. In some of these, L is an alkyl group having a chain length of 0 to 5 atoms. In others, L is —NH—$(CH_2)_n$—NH—C(O)—, wherein n is 1 to 12. In others, the compound is:

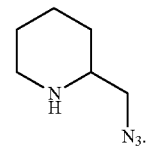

In some embodiments of the compound of the formula (I), (II), (III), (IV), (XIII), (V), (VI), (VII), (VIII), (XIV), (IX), (X), (XI) or (XII), the reporter molecule comprises a chromophore, fluorophore, fluorescent protein, phosphorescent dye, tandem dye, particle, hapten, enzyme, or radioisotope. In some of these, the fluorophore is a xanthene, coumarin, cyanine, pyrene, oxazine, borapolyazaindacene, or carbopyranine. In others, the enzyme is horseradish peroxidase, alkaline phosphatase, beta-galactosidase, or beta-lactamase. In others, the particle is a semiconductor nanocrystal.

In some embodiments of the compound of the formula (I), (II), (III), (IV), (XIII), (V), (VI), (VII), (VIII), (XIV), (IX), (X), (XI) or (XII), the carrier molecule is an amino acid, peptide, protein, polysaccharide, nucleoside, nucleotide, oligonucleotide, nucleic acid, hapten, psoralen, drug, hormone, lipid, lipid assembly, tyramine, synthetic polymer, polymeric microparticle, biological cell, cellular component, ion chelating moiety, enzymatic substrate, or virus.

In some embodiments of the compound of the formula (I), (II), (III), (IV), (XIII), (V), (VI), (VII), (VIII), (XIV), (IX), (X), (XI) or (XII), the carrier molecule is an antibody, antibody fragment, antigen, avidin, streptavidin, biotin, dextran, IgG binding protein, fluorescent protein, agarose, or non-biological microparticle.

In some embodiments of the compound of the formula (I), (II), (III), (IV), (XIII), (V), (VI), (VII), (VIII), (XIV), (IX), (X), (XI) or (XII), the solid support is an aerogel, hydrogel, resin, bead, biochip, microfluidic chip, silicon chip, multi-well plate, membrane, conducting metal, nonconducting metal, glass, or magnetic support.

In some embodiments of the compound of the formula (I), (II), (III), (IV), (XIII), (V), (VI), (VII), (VIII), (XIV), (IX), (X), (XI) or (XII), the solid support is a silica gel, polymeric membrane, particle, derivatized plastic film, glass bead, cotton, plastic bead, alumina gel, polysaccharide, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene, nylon, latex bead, magnetic bead, paramagnetic bead, superparamagnetic bead, or starch.

In some embodiments of the compound of the formula (I), (II), (III), (IV), (XIII), (V), (VI), (VII), (VIII), (XIV), (IX), (X), (XI) or (XII), the therapeutic molecule is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, or analogs or homologs thereof.

In some embodiments of the compound of the formula (I), (II), (III), (IV), (XIII), (V), (VI), (VII), (VIII), (XIV), (IX), (X), (XI) or (XII), the therapeutic molecule is an antimetabolite, alkylating agent, anthracycline, antibiotic, or anti-mitotic agent.

In some embodiments of the compound of the formula (I), (II), (III), (IV), (XIII), (V), (VI), (VII), (VIII), (XIV), (IX), (X), (XI) or (XII), the therapeutic molecule is abrin, ricin A, pseudomonas exotoxin, diphtheria toxin, tumor necrosis factor, γ-interferon, α-interferon, nerve growth factor, platelet derived growth factor, tissue plasminogen activator, interleukin-1, interleukin-2, interleukin-6, granulocyte macrophage colony stimulating factor, or granulocyte colony stimulating factor.

In some embodiments of the compound of the formula (I), (II), (III), (IV), (XIII), (V), (VI), (VII), (VIII), (XIV), (IX), (X), (XI) or (XII), G is an alkyne-reactive group. In some of these, the alkyne-reactive group is an azide.

In some embodiments of the compound of the formula (I), (II), (III), (IV), (XIII), (V), (VI), (VII), (VIII), (XIV), (IX), (X), (XI) or (XII), G is an azide-reactive group. In some of these, the azide-reactive group is a terminal alkyne.

In another aspect, the invention provides a method of modifying a biomolecule comprising the step of reacting in a solution a biomolecule comprising an azide reactive moiety with a compound of the formula (I), (II), (III), (IV), (XIII), (V), (VI), (VII), (VIII), (XIV), (IX), (X), (XI) or (XII), wherein the therapeutic molecule is an antimetabolite, alkylating agent, anthracycline, antibiotic, or anti-mitotic agent to provide a modified biomolecule.

In some embodiments, the azide reactive moiety comprises a terminal alkyne, an activated alkyne, or triarylphosphine.

In another aspect, the invention provides a method of modifying a biomolecule comprising the step of reacting in a solution a biomolecule comprising an alkyne reactive moiety with a compound of the formula (I), (II), (III), (IV), (XIII), (V), (VI), (VII), (VIII), (XIV), (IX), (X), (XI) or (XII), wherein G is an alkyne reactive moiety to provide a modified biomolecule.

In some embodiments, the alkyne reactive moiety comprises an azide.

In some embodiments, the biomolecule is a nucleic acid, oligonucleotide, protein, peptide, carbohydrate, polysaccharide, glycoprotein, lipid, hormone, drug, or prodrug.

In some embodiments, the solution further comprises copper ions. In some of these, the solution further comprises at least one reducing agent. In some of these, the at least one reducing agent is ascorbate, Tris(2-Carboxyethyl) Phosphine (TCEP), TCP (2,4,6-trichlorophenol), NADH, NADPH, thiosulfate, 2-mercaptoethanol, dithiothreitol, glutathione, cysteine, metallic copper, quinone, hydroquinone, vitamin K1, Fe2+, Co2+, or an applied electric potential. In some of these, the at least one reducing agent is ascorbate.

In some of these, the solution further comprises a copper chelator. In some of these, the copper chelator is a copper I chelator. In some of these, the copper chelator I is a compound of formula:

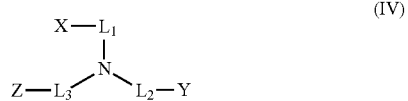

wherein X, Y, and Z each independently have the formula:

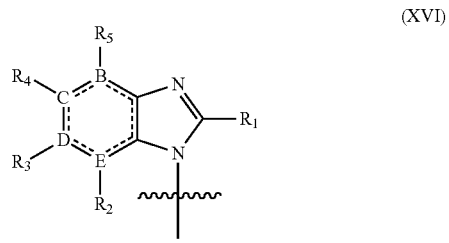

wherein:

$R_1$, $R_2$, $R_3$, $R_4$ and $R_5$ are independently selected from hydrogen, halogen, —$SO_3X$, a carboxylic acid, a salt of carboxylic acid, CN, nitro, hydroxyl, amino, alkyl, heteroalkyl, alkoxy, cycloalkyl, heterocycloalkyl, substituted alkyl, substituted heteroalkyl, substituted alkoxy, alkylthio, alkanoylamino, alkylaminocarbonyl, substituted cycloalkyl, substituted heterocycloalkyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; and B, C, D, and E are C or N; and $L_1$, $L_2$, and $L_3$ are covalent linkage having 1-5 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, and substituted heterocycloalkyl.

In some of these, $R_1$, $R_2$, $R_3$, $R_4$ and $R_5$ for at least one substituent selected from X, Y, and Z are each H. In some of these, $R_1$, $R_2$, $R_3$, $R_4$ and $R_5$ for each of X, Y, and Z are each H.

In some of these, $L_1$, $L_2$ and $L_3$ are each alkyl groups having a chain length of 1-5 atoms.

In some of these, $L_1$, $L_2$ and $L_3$ are each —$CH_2CH_2$—.

In others, the copper chelator is N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, or a derivative thereof, trientine, glutathione, histidine, polyhistidine, tris-(hydroxypropyltriazolylmethyl)amine (THPTA), or tetraethylenepolyamine (TEPA).

In others, the copper chelator is 1,10 phenanthroline, bathophenanthroline disulfonic acid (4,7-diphenyl-1,10-phenanthroline disulfonic acid), or bathocuproine disulfonic acid (2,9-dimethyl-4,7-diphenyl-1,10-phenanthroline disulfonate).

In another aspect, the provides a kit comprising a compound of the formula (I), (II), (III), (IV), (XIII), (V), (VI), (VII), (VIII), (XIV), (IX), (X), (XI) or (XII).

In some embodiments, the kit further comprises a copper ion source.

In some embodiments, the kit further comprises at least one reducing agent. In some of these, the at least one reducing agent is ascorbate, Tris(2-Carboxyethyl) Phosphine (TCEP), TCP (2,4,6-trichlorophenol), NADH, NADPH, thiosulfate, 2-mercaptoethanol, dithiothreitol, glutathione, cysteine, metallic copper, quinone, hydroquinone, vitamin K1, Fe2+, Co2+, or an applied electric potential. In others, the at least one reducing agent is ascorbate.

In some embodiments, the kit further comprises a copper chelator. In some of these, the copper chelator is a copper I chelator. In some of these, the copper chelator I is a compound of formula:

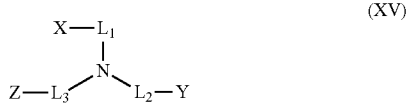

(XV)

wherein X, Y, and Z each independently have the formula:

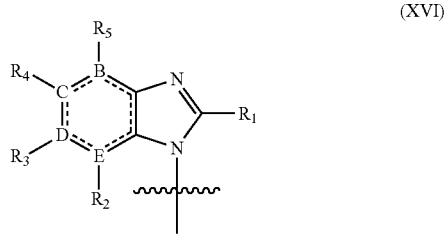

(XVI)

wherein:
$R_1$, $R_2$, $R_3$, $R_4$ and $R_5$ are independently selected from hydrogen, halogen, —$SO_3X$, a carboxylic acid, a salt of carboxylic acid, CN, nitro, hydroxyl, amino, alkylthio, alkanoylamino, alkylaminocarbonyl, arylcarboxamido, alkyl aryl portions are optionally substituted one or more times by halogen, —$SO_3X$, a carboxylic acid, a salt of carboxylic acid, CN, nitro, hydroxyl, amino, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; and
B, C, D, and E are C or N; and
$L_1$, $L_2$, and $L_3$ are covalent linkage having 1-5 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, and substituted heterocycloalkyl.

In some of these, $R_1$, $R_2$, $R_3$, $R_4$ and $R_5$ for at least one substituent selected from X, Y, and Z are each H. In some of these, $R_1$, $R_2$, $R_3$, $R_4$ and $R_5$ for each of X, Y, and Z are each H.

In some of these, $L_1$, $L_2$ and $L_3$ are each alkyl groups having a chain length of 1-5 atoms. In some of these, $L_1$, $L_2$ and $L_3$ are each —$CH_2CH_2$—.

In others, the copper chelator is N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, or a derivative thereof, trientine, glutathione, histidine, polyhistidine, tris-(hydroxypropyltriazolylmethyl)amine (THPTA), or tetraethylenepolyamine (TEPA).

In others, the copper chelator is 1,10 phenanthroline, bathophenanthroline disulfonic acid (4,7-diphenyl-1,10-phenanthroline disulfonic acid), or bathocuproine disulfonic acid (2,9-dimethyl-4,7-diphenyl-1,10-phenanthroline disulfonate).

In another aspect, the invention provides a compound selected from the group consisting of:

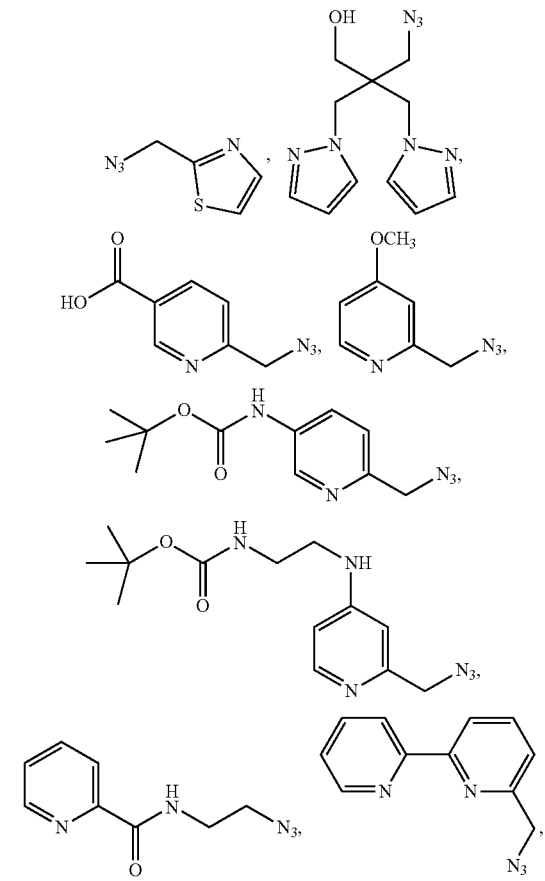

-continued

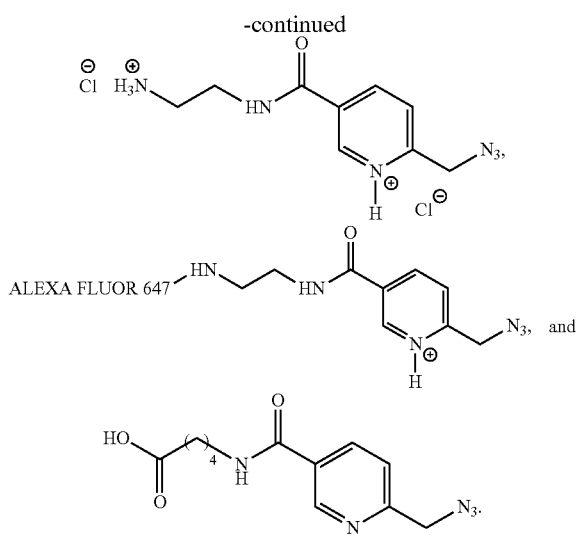

In another aspect, the invention provides a composition comprising a compound of the formula (I), (II), (III), (IV), (XIII), (V), (VI), (VII), (VIII), (XIV), (IX), (X), (XI) or (XII); and a copper chelator I of the formula (XV).

DETAILED DESCRIPTION

Figure 1A:
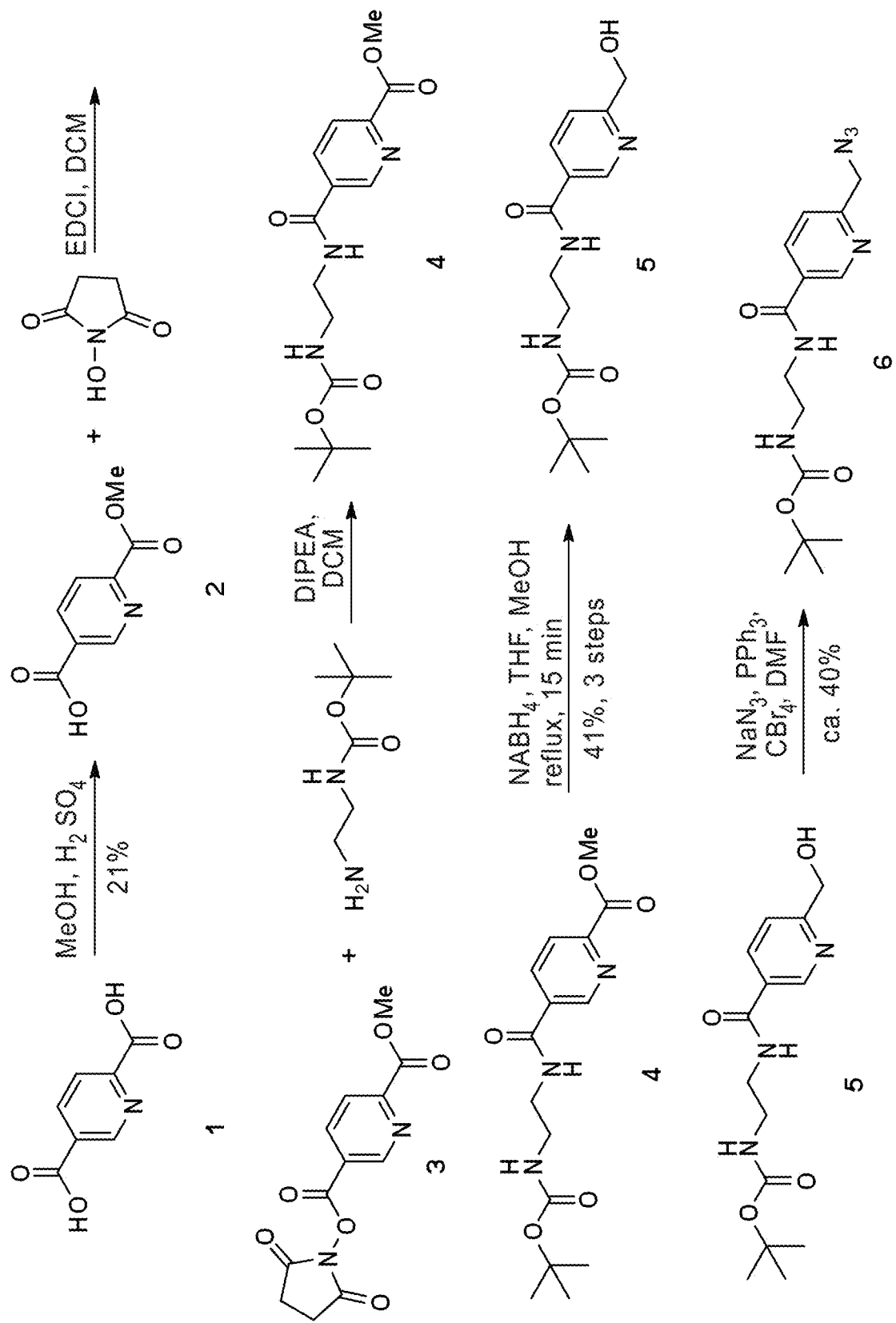
FIG. 1 shows a reaction scheme for (A) the synthesis of tert-butyl (2-(6-(azidomethyl)nicotinamido)ethyl) carbamate (6), and (B) fluorescent-labeling of compound (6), as described in Example 1.

The present invention has utility in the study of biomolecules, both in vivo and in vitro.

The present invention provides compositions, methods, and kits for the labeling, detecting, isolating and/or analysis of biomolecules modified by attachment of chemical handles.

Definitions and Abbreviations

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkenyl") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include derivatives of alkyl, such as those defined below, including heteroalkyl, cycloalkyl, heterocycloalkyl, substituted alkyl, substituted heteroalkyl, substituted cycloalkyl, and substituted heterocycloalkyl. Alkyl groups that are limited to hydrocarbon groups are termed "homoalkyl".

In some embodiments, an alkyl group contains between 1 and 25 carbons, between 1 and 20 carbons (i.e., $C_1$ to $C_{20}$ alkyl), between 1 and 15 carbons (i.e., $C_1$ to Cis alkyl), between 1 and 10 carbons (i.e., $C_1$ to $C_{10}$ alkyl), or between 1 and 8 carbons (i.e., $C_1$ to $C_8$ alkyl). Straight, branched or cyclic hydrocarbon chains having eight or fewer carbon atoms may also be referred to herein as "lower alkyl". In addition, the term "alkyl" as used herein may further include one or more substitutions at one or more carbon atoms of the hydrocarbon chain fragment.

The term "carboxyalkyl" as used herein refers to a straight or branched-chain alkyl including cycloalkyl comprising at least one —COOH substituent. The terms "alkoxy," "alkylamino" and "alkylthio" (or thioalkoxy) are used in their conventional sense, and refer to heteroalkyl groups attached to the remainder of the molecule via an oxygen atom, an amino group, or a sulfur atom, respectively.

The term "acyl" or "alkanoyl" by itself or in combination with another term, means, unless otherwise stated, a stable straight or branched chain, or cyclic alkyl, or combinations thereof, with an acyl radical on at least one terminus of the alkyl. An "acyl radical" is a group derived from a carboxylic acid by removing the —OH moiety therefrom.

The term "amino" or "amine group" refers to the group —NR'R" where R' and R" are independently selected from hydrogen, alkyl, heteroalkyl, cycloalkyl, heterocycloalkyl, substituted alkyl, substituted heteroalkyl, substituted cycloalkyl, substituted heterocycloalkyl, aryl, heteroaryl, substituted aryl, arylalkyl, substituted arylalkyl, and substituted heteroaryl. In a primary amine group, both R and R' are hydrogen, whereas in a secondary amine group, either, but not both, R' or R' is hydrogen. In a tertiary amine group, neither R' nor R" is a hydrogen. A substituted amine is an amine group wherein R' and/or R" is other than hydrogen. In addition, the terms "amine" and "amino" can include protonated and quaternized versions of nitrogen, comprising the group —NRR'R" and its biologically compatible anionic counterions.

As used herein, the term "heteroatom" includes oxygen (O), nitrogen (N), sulfur (S), phosphorus (P), silicon (Si), and selenium (Se).

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. In some embodiments, an aryl group contains twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; sulfo; alkyl- or arylsufonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl," "heteroaryl," etc.) includes both substituted and unsubstituted forms of the indicated radical. Nonlimiting exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR, =N—OR', —NR'R", —SR, -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

The term "chain length," as used herein, refers to the smallest number of carbon and/or heteroatoms between two substituents. As a nonlimiting example, the chain length between X and Y in the molecule X—(CH$_2$)$_3$—CH(CH$_2$CH$_3$)—NH—Y is 5.

The term "activated alkyne," as used herein, refers to a cyclooctyne that selectively reacts with an azide on another molecule to form a covalent chemical bond between the activated alkyne group and the alkyne reactive group. Activated alkynes include, but are not limited to, cyclooctynes and difluorocyclooctynes, described, e.g., in Agard et al., J. Am. Chem. Soc., 2004, 126 (46):15046-15047; dibenzocyclooctynes, described, e.g., in Boon et al., WO2009/067663 A1 (2009); and aza-dibenzocyclooctynes, described, e.g., in Debets et al., Chem. Comm., 2010, 46:97-99. These dibenzocyclooctynes (including the aza-dibenzocyclooctynes) described above are collectively referred to herein as cyclooctyne groups.

The term "affinity," as used herein, refers to the strength of the binding interaction of two molecules, such as an antibody and an antigen, or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "high affinity" refers to a ligand that binds to an antibody having an affinity constant (K$_a$) greater than 10$^4$ M$^{-1}$, typically 10$^5$-10$^{11}$ M$^{-1}$; as determined by inhibition ELISA or an equivalent affinity determined by comparable techniques such as, for example, Scatchard plots or using K$_d$/dissociation constant, which is the reciprocal of the K$_a$.

The term "alkyne reactive," as used herein, refers to a chemical moiety that selectively reacts with an alkyne, such as a terminal alkyne or an activated alkyne, on another molecule to form a covalent chemical bond between the alkyne modified group and the alkyne reactive group. Examples of alkyne-reactive groups include, but are not limited to, azide and nitrones. "Alkyne-reactive" can also refer to a molecule that contains a chemical moiety that selectively reacts with an alkyne group.

The term "antibody," as used herein, refers to a protein of the immunoglobulin (Ig) superfamily that binds noncovalently to certain substances (e.g. antigens and immunogens) to form an antibody-antigen complex. Antibodies can be polyclonal or monoclonal. Antibodies can also be chimeric, humanized, or human antibodies. It is understood that the term "antibody" as used herein includes within its scope any of the various classes or sub-classes of immunoglobulin derived from any of the animals conventionally used, or from human.

The term "antibody fragments," as used herein, refers to fragments of antibodies that retain the principal selective binding characteristics of the whole antibody. Nonlimiting exemplary antibody fragment include Fab, Fab', F(ab')$_2$, Fv, and single-chain Fv (scFv). Further nonlimiting exemplary antibody fragments include (i) the Fd fragment, consisting of the VH and CH1 domains; (ii) the dAb fragment (Ward, et al., Nature 341, 544 (1989)), which consists of a VH domain; and (iii) isolated CDR regions. In addition, arbitrary fragments can be made using recombinant technology that retains antigen-recognition characteristics.

The term "antigen," as used herein, refers to a molecule or molecules to which an antibody binds selectively. An antigen may comprise any type of molecule, such as, for example, protein, oligonucleotide, polysaccharide, or small molecule. In some embodiments, an antigen comprises more than one molecule, such as for example, a heterodimeric receptor, a receptor bound to its ligand, or a complex comprising a protein and a small molecule or oligonucleotide. In some embodiments, a target is an antigen.

The term "aqueous solution," as used herein, refers to a solution that is at least 50% water. In some embodiments, an aqueous solution retains the solution characteristics of water.

The term "azide reactive," as used herein, refers to a chemical moiety that selectively reacts with an azide on another molecule to form a covalent chemical bond between the azido modified group and the azide reactive group. Examples of azide-reactive groups include, but are not limited to, alkyne, including, but not limited to, terminal alkynes and activated alkynes; and phosphines, including, but not limited to, triarylphosphines. "Azide-reactive" can also refer to a molecule that contains a chemical moiety that selectively reacts with an azido group.

The term "biomolecule," as used herein, refers to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides, drugs, prodrugs, etc., which may be found in a living organism (including an isolated cell). A biomolecule need not be a naturally-occurring molecule, but may be a molecule that has been introduced into the living organism or an ancestor of the living organism, e.g., directly, through transgenic methods, or otherwise.

The term "carrier molecule," as used herein, refers to a biological or a non-biological moiety that is covalently bonded to a compound of the present invention, and which confers a desirable property on the compound and/or on a biomolecule conjugated thereto. Nonlimiting exemplary such desirable properties include binding properties, such as, for example, the ability to specifically bind to another moiety (e.g., a member of a binding pair); increasing half-life; increasing solubility; and directing the compound to a particular location in a cell or organism. Such moieties include, but are not limited to, amino acids, peptides, proteins, polysaccharides, nucleosides, nucleotides, oligonucleotides, nucleic acids, haptens, psoralens, drugs, hormones, lipids, lipid assemblies, synthetic polymers, polymeric microparticles, biological cells, viruses, and combinations thereof.

The term, "chemical handle," as used herein, refers to a functional group that is capable of undergoing a click reaction, a 1,3-dipolar cycloaddition, and/or a Staudinger ligation. Nonlimiting exemplary chemical handles include alkyne-reactive moieties, such as azide; and azide-reactive moieties, such as alkynes, including, but not limited to, terminal alkynes and activated alkynes; and phosphines, including, but not limited to, a triarylphosphine; and the like.

The term "complementary chemical handle," as used herein, refers to a functional group that is capable of undergoing a click reaction, a 1,3-dipolar cycloaddition, and/or a Staudinger ligation with a specified chemical handle. For example, for an azide chemical handle, complementary chemical handles include, but are not limited to, alkynes, such as terminal alkynes and activated alkynes, and phosphines, such as triarylphosphines.

The terms "click chemistry" and "click reaction," as used herein, refer to copper ion-catalyzed 1,3-dipolar cycloadditions between an azide and a terminal alkyne to form a 1,2,3-triazole.

The term "1,3-dipolar cycloaddition," as used herein, refers to reactions between an azide and an alkyne to form a 1,2,3-triazole.

The term "copper ion source," as used herein, refers to any source of Cu(I) ions, whether or not formation of Cu(I) ions involves other agents, such as reducing agents. Nonlimiting exemplary copper ion sources include copper salts, such as $Cu(NO_3)_2$ $Cu(OAc)_2$ or $CuSO_4$; copper halides, such as CuBr and CuI; and copper-containing metals, such as copper wire.

The terms "copper ion chelator" and "copper chelator," as used herein, refer to a moiety that binds to, and stabilizes, Cu(I) ions. Nonlimiting exemplary copper chelators are discussed herein.

The term "halogen," as used herein, refers to an atom selected from F, Cl, Br, and I.

The term "linker" or "L," as used herein, refers to a single covalent bond or a series of stable covalent bonds incorporating 1-30 nonhydrogen atoms selected from the group consisting of C, N, O, S, P, Si, and Se. Exemplary linking members include moieties that includes —C(O)NH—, —C(O)O—, —NH—, —S—, —O—, and the like. In some embodiments, a linker has a chain length of 1-30 atoms, or 1-25 atoms, or 1-20 atoms, or 1-15 atoms, or 1-10 atoms, or 1-5 atoms. A "cleavable linker" is a linker that has one or more covalent bonds that can be broken under particular reaction conditions or in the presence of a particular molecule or enzyme, such that the moiety on one side of the cleavable linker is no longer covalently bound to the moiety on the other side of the cleavable linker. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage (for both cleavable linkers and cleavable groups) is either chemical in nature, or enzymatically mediated. Exemplary enzymatically cleavable linkers and groups include natural amino acids or peptide sequences that end with a natural amino acid. In addition to enzymatically cleavable linkers and groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and heterobifunctional) spacer arms are commercially available. An exemplary cleavable linker or group, an ester, may be cleaved by a reagent, e.g. sodium hydroxide, resulting in a carboxylate-containing product and a hydroxyl-containing product.

The term "low copper," as used herein, refers to a copper concentration of less than 1 millimolar.

The term "modified biomolecule" as used herein refers to a biomolecule which has been modified by covalent attachment of at least one chemical handle. A biomolecule may be modified in vitro or in vivo.

The term "phosphine reactive" as used herein refers to a chemical moiety that selectively reacts via Staudinger ligation with a phosphine group, including but not limited to a triarylphosphine group, on another molecule to form a covalent chemical bond. Examples of phosphine reactive groups include, but are not limited to, azide.

The terms "protein" and "polypeptide" are used herein in a generic sense to refer to polymers of amino acid residues of any length. The term "peptide" is used herein to refer to polypeptides having fewer than 100 amino acid residues, typically fewer than 10 amino acid residues. The amino acid residues in a polypeptide, protein, or peptide may be naturally-occurring amino acid residues or non-naturally occurring amino acid residues.

The term "reducing agent," as used herein, refers to an agent that is capable of reducing Cu(II) to Cu(I). Nonlimiting exemplary reducing agents include ascorbate, tris(2-carboxyethyl) phosphine (TCEP), NADH, NADPH, thiosulfate, metallic copper, hydroquinone, vitamin $K_1$, glutathione, cysteine, 2-mercaptoethanol, dithiothreitol, and an applied electric potential. Nonlimiting exemplary metals that may act as reducing agents include Al, Be, Co, Cr, Fe, Mg, Mn, Ni, Zn, Au, Ag, Hg, Cd, Zr, Ru, Fe, Co, Pt, Pd, Ni, Rh, and W.

The term "reporter molecule" refers to a moiety that is directly or indirectly detectable. In some embodiments, and as a non-limiting example, a reporter molecule may be directly detectable, e.g., due to its spectral properties. In some embodiments, and as a non-limiting example, a reporter molecule may be indirectly detectable, e.g., due to its enzymatic activity, wherein the enzymatic activity produces a directly detectable signal. Such reporter molecules include, but are not limited to, radiolabels; pigments, dyes, and other chromogens; spin labels; fluorescent labels (i.e., fluorophores such as coumarins, cyanines, benzofurans, quinolines, quinazolinones, indoles, benzazoles, borapolyazaindacenes, and xanthenes, including fluoresceins, rhodamines, and rhodols); chemiluminescent substances, wherein the detectable signal is generated by chemical modification of substance; metal-containing substances; enzymes, wherein the enzyme activity generates a signal (such as, for example, by forming a detectable product from a substrate; haptens that can bind selectively to another molecule (such as, for example, an antigen that binds to an antibody; or biotin, which binds to avidin and streptavidin). Many reporter molecules are known in the art, some of which are described, e.g., in Richard P. Haugland, Molecular Probes Handbook of Fluorescent Probes and Research Products ($9^{th}$ edition, CD-ROM, September 2002), supra.

The term "solid support," as used herein, refers to a material that is substantially insoluble in a selected solvent system, or which can be readily separated (e.g., by precipitation) from a selected solvent system in which it is soluble. Solid supports useful in practicing the present invention may include groups that are activated or capable of activation such that one or more compounds described herein will bind to the solid support.

The terms "structural integrity of the [biomolecule] is not reduced" or "preservation of the structural integrity of the [biomolecule]", as used herein, mean that either: 1) when analyzed by gel electrophoresis and detection (such as staining), a band or spot arising from the labeled biomolecule is not reduced in intensity by more than 20%, and preferably not reduced by more than 10%, with respect to the corresponding band or spot arising from the same amount of the electrophoresed unlabeled biomolecule, arising from the labeled biomolecule analyzed; or 2) when analyzed by gel electrophoresis, a band or spot arising from the labeled biomolecule is not observed to be significantly less sharp than the corresponding band or spot arising from the same amount of the electrophoresed unlabeled biomolecule, where "significantly less sharp" (synonymous with "significantly more diffuse") means the detectable band or spot takes up at least 5% more, preferably 10% more, more preferably 20% more area on the gel than the corresponding unlabeled biomolecule. Other reproducible tests for structural integrity of labeled biomolecules include, without limitation detection of released amino acids or peptides, or mass spectrometry.

The term "therapeutic molecule" refers to a molecule that can be used to treat and/or alleviate a condition and/or symptom in a subject, and/or can be used to affect biological processes in cells in vitro. Therapeutic molecules include, but are not limited to, antimetabolites, alkylating agents, anthracyclines, antibiotics, and anti-mitotic agents. Nonlimiting exemplary therapeutic molecules include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, abrin, ricin A, pseudomonas exotoxin, diphtheria toxin, tumor necrosis factor, γ-interferon, α-interferon, nerve growth factor, platelet derived growth factor, tissue plasminogen activator, interleukin-1, interleukin-2, interleukin-6, granulocyte macrophage colony stimulating factor, or granulocyte colony stimulating factor, and analogs or homologs thereof.

The present invention provides low-copper click reactions, 1,3-dipolar cycloadditions, and Staudinger ligations involving a modified biomolecule and a compound of any one of Formulas (I) to (XIII). In some embodiments, the modified biomolecule comprises an azide moiety and the compound of any one of Formulas (I) to (XIII) comprises a terminal alkyne. In some embodiments, the modified biomolecule comprises an alkyne, such as a terminal alkyne or an activated alkyne, or a phosphine, such as a triarylphosphine, and the compound of any one of Formulas (I) to (XIII) comprises an azide moiety.

Accordingly, provided herein are compounds, compositions, methods, and kits for the labeling, detecting, isolating and/or analysis of biomolecules. In some embodiments, presented are novel compounds comprising an azide moiety or an alkyne moiety. In some embodiments, methods are provided for covalently attaching the novel compounds to modified biomolecules using a click reaction, a 1,3-dipolar cycloaddition, or a Staudinger ligation. In some such embodiments, the method comprises labeling, detecting, isolating and/or analyzing the biomolecule.

Click Chemistry

Azides and terminal alkynes can undergo Cu(I)-catalyzed Azide-Alkyne Cycloaddition (CuAAC) at room temperature. Such Cu(I)-catalyzed azide-alkyne cycloadditions, sometimes referred to as click chemistry, typically results in formation of a 1,2,3-triazole. Various exemplary click reactions are known in the art, and are described, e.g., in U.S. Publication No. 2005/0222427.

Click reactions can be performed in a variety of aqueous solutions, including, but not limited to, water, and mixtures of water and various miscible or partially miscible organic solvents. Nonlimiting such organic solvents include alcohols, dimethyl sulfoxide (DMSO), dimethyl formamide (DMF), tert-butanol (tBuOH) and acetone.

In some embodiments, the copper used as a catalyst in a click reaction is Cu(I) ions. Exemplary sources of Cu(I) ions include, but are not limited to, cuprous halides such as cuprous bromide or cuprous iodide. In some embodiments, a click reaction is carried out in the presence of Cu(II) ions and a reducing agent, which reduces the Cu(II) to Cu(I) in situ. Exemplary sources of Cu(II) ions include, but are not limited to, $Cu(NO_3)_2$, $Cu(OAc)_2$, and $CuSO_4$. Nonlimiting exemplary reducing agents include ascorbate, tris(2-carboxyethyl) phosphine (TCEP), NADH, NADPH, thiosulfate, metallic copper, hydroquinone, vitamin $K_1$, glutathione, cysteine, 2-mercaptoethanol, dithiothreitol, $Fe^{2+}$, $Co^{2+}$, and an applied electric potential. In some embodiments, a reducing agent is a metal selected from Al, Be, Co, Cr, Fe, Mg, Mn, Ni, Zn, Au, Ag, Hg, Cd, Zr, Ru, Fe, Co, Pt, Pd, Ni, Rh, and W.

In some embodiments, the reducing agent is included in a click reaction in a micromolar to millimolar range. In some embodiments, the concentration of the reducing agent is between 100 μM and 100 mM, between 10 μM and 10 mM, or between 1 μM and 1 mM.

In some embodiments, a click reaction includes a chelator that stabilizes Cu(I) ions. Nonlimiting exemplary such chelators are described herein.

In some embodiments, at least one copper chelator is included in a click reaction. In some such embodiments, the copper chelator is added after a Cu(II) source has been contacted with a reducing agent. In some embodiments, the copper chelator is added at the same time the Cu(II) source is contacted with a reducing agent. In some embodiments, a copper chelator is added to a solution containing one or both of the click reactants (i.e., a solution containing one or both of the azide-containing reactant and the alkyne-containing reactant), and a solution containing the Cu(II) source and the reducing agent is subsequently added to initiate the click reaction.

In some embodiments, a click reaction comprises a compound of any one of Formulas (I) to (XIII) and a modified biomolecule. In some such embodiments, the compound of any one of Formulas (I) to (XIII) comprises a terminal alkyne and the modified biomolecule comprises an azide. In some embodiments, the compound of any one of formulas (I) to (XIII) comprises an azide and the modified biomolecule comprises a terminal alkyne. In some embodiments, a click reaction further comprises Cu(I) ions. In some embodiments, a click reaction further comprises Cu(II) ions and at least one reducing agent. In some embodiments, a click reaction further comprises a copper chelator.

Activated Alkyne Chemistry (1,3-Dipolar Cycloadditions)

In some instances, azides and alkynes can undergo catalyst-free 1,3-dipolar cycloaddition when an activated alkyne is used. In some embodiments, alkynes can be activated by ring strain such as, by way of example only, eight membered ring structures, including seven to ten-membered ring structures with electron-withdrawing groups appended thereon. In some embodiments, alkynes can be activated by the addition of a Lewis acid such as, by way of example only, Au(I) or Au(III). Nonlimiting exemplary activated alkynes include cyclooctynes and difluorocyclooctynes, which are described, e.g., in Agard et al., *J. Am. Chem. Soc.,* 2004, 126 (46):15046-15047; dibenzocyclooctynes, which are described, e.g., in Boon et al., WO2009/067663 A1; and aza-dibenzocyclooctynes, which are described, e.g., in Debets et al., *Chem. Comm.,* 2010, 46:97-99.

Typically, an activated alkyne conjugated with fluorophores or antibody undergoes cycloaddition to azide in one to twelve hour at room temperature. The reaction can be carried out in organic or aqueous solvents, buffers like PBS, TRIS or mixtures of buffers and organic solvents.

In some embodiments of the methods described herein, a modified biomolecule comprises an activated alkyne and a compound of any one of Formulas (I) to (XIII) comprises an azide.

Staudinger Ligation

In a Staudinger ligation, an azide is reacted with a triarylphosphine comprising an electrophilic trap (typically, a methyl ester). Following formation of an aza-ylide intermediate, the intermediate rearranges to produce a ligated product having an amide linkage, and a phosphine oxide. Such ligations are described, e.g., in U.S. Publication No. 2006/0276658. In some embodiments, the phosphine comprises an acyl group such as an ester, thioester or N-acyl imidazole (i.e. a phosphinoester, phosphinothioester, phosphinoimidazole) to trap the aza-ylide intermediate and form an amide bond upon hydrolysis. In some embodiments, the phosphine can be a di- or triarylphosphine to stabilize the phosphine. The phosphines used in Staudinger ligation methods described herein include, but are not limited to, cyclic or acyclic, halogenated, bisphosphorus, or polymeric phosphines.

A typical procedure for a Staudinger ligation is as follows (J. Am. Chem. Soc. 2002, 124, 14893-14902): The cells were pelleted (3500 rpm, 3 min) and washed twice with 200 µL of labeling buffer (1% FBS in PBS, pH) 7.4). After the second wash, cells were typically resuspended in a volume of 50 µL of labeling buffer and 50 µL of 2 in solution (0.5 mM in PBS, pH) 7.4). After incubation at room temperature for 1 h, the cells were pelleted (3500 rpm, 3 min) and washed three times with ice-cold labeling buffer, the cells were pelleted, washed with 200 µL of ice-cold labeling buffer, and then diluted to a volume of 400 µL for flow cytometry analysis.

In some embodiments of the methods described herein, a modified biomolecule comprises a phosphine and a compound of any one of Formulas (I) to (XIII) comprises an azide.

Compounds for Conjugating Biomolecules

In some embodiments, the present invention provides compounds having the formula:

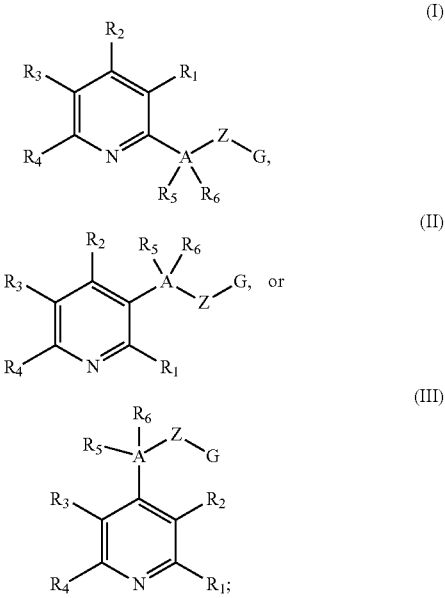

wherein:

A is a carbon, or A, $R_5$, and $R_6$ are absent;

$R_1$, $R_2$, $R_3$, and $R_4$, are independently selected from hydrogen, halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido; or two substituents selected from $R_1$, $R_2$, $R_3$, and $R_4$, wherein each of the at least two substituents are on different carbon atoms together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or at least two of the remaining substituents together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and any remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

$R_5$, and $R_6$, are independently selected from hydrogen, halogen, —$SO_3X$, a carboxylic acid, a salt of carboxylic acid, CN, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido, alkyl and aryl portions are optionally substituted one or more times by halogen, —$SO_3X$, a carboxylic acid, a salt of carboxylic acid, CN, nitro, hydroxyl, amino, hydrazine, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, alkylthio, alkanoylamino, alkylaminocarbonyl, aryl, heteroaryl, substituted aryl, arylalkyl, substituted arylalkyl, and substituted heteroaryl, arylcarboxamido;

at least one substituent selected from $R_1$, $R_2$, $R_3$, $R_4$, $R_5$ and $R_6$ comprises X-L-, wherein:

X is selected from a reporter molecule, a carrier molecule, a solid phase, a therapeutic molecule such as peptide, a protein, an antibody, a polysaccharide, a nucleic acid polymer, an ion complexing moiety, a lipid or a non-biological organic polymer or polymeric micro or nano particle, that are optionally bound to one or more additional fluorophores; or X is a reactive group such as carboxylic acid, an activated ester of carboxylic acid, an amine, a hydrazine, a haloacetamide, an alkyl halide, an isothiocynate or a maleimide group; and L is an independently a single covalent bond or L is covalent linkage having 1-24 non-hydrogen atoms selected from the group consisting of C, N, O, P and S and composed of any combinations of single, double, triple or aromatic carbon-carbon bonds, carbon-nitrogen bonds, nitrogen-nitrogen bonds, carbon-oxygen bonds, carbon-sulfur bonds, phosphorus-oxygen bonds and phosphorus-nitrogen bonds in the form of alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl;

Z is an independently a single covalent bond or Z is covalent linkage having 1-10 non-hydrogen atoms selected from the group consisting of C, N, O, P and S and composed of any combinations of single, double, triple or aromatic carbon-carbon bonds, carbon-nitrogen bonds, carbon-oxygen bonds, and carbon-sulfur bonds in the form of a straight- or branched-chain alkyl or heteroalkyl chain;

G is a chemical handle selected from an azide-reactive group, an alkyne-reactive group, and a phosphine-reactive group.

In some embodiments, the compound is of the formula:

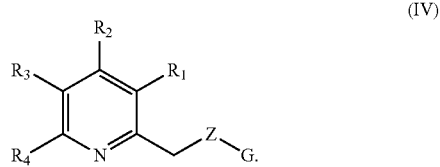

(IV)

In some embodiments, the compound is of the formula:

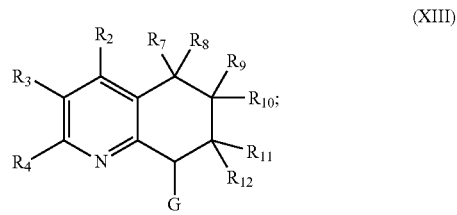

(XIII)

wherein $R_2$, $R_3$, $R_4$, and $R_7$ to $R_{12}$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two substituents selected from $R_2$, $R_3$, $R_4$, and $R_7$ to $R_{12}$, wherein the two substituents are on different carbon atoms, together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two of the remaining substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl.

In some embodiments, the present invention provides compounds having the formula:

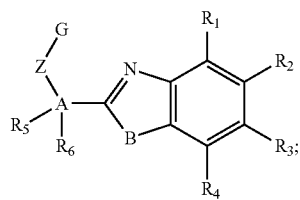

(V)

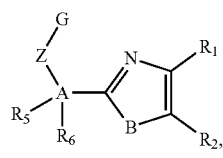

(VI)

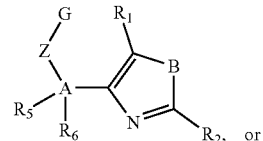

(VII)

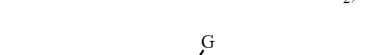

(VIII)

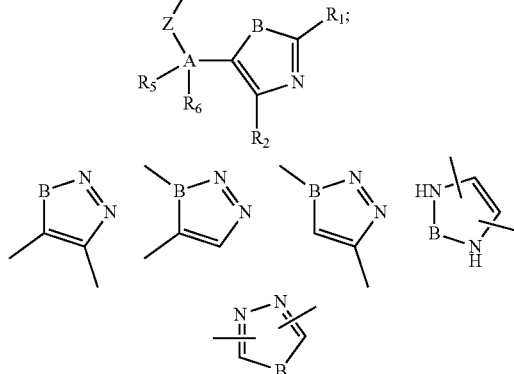

wherein:

R$_1$, R$_2$, R$_3$, and R$_4$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two substituents selected from R$_1$, R$_2$, R$_3$, and R$_4$ together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining two substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, or the remaining two substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

at least one substituent selected from R$_1$, R$_2$, R$_3$, R$_4$, R$_5$, and R$_6$ comprises X-L-, wherein:

X is selected from a reporter molecule, a carrier molecule, a solid phase, or a therapeutic molecule; and L is a group selected from alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, having a chain length of 0-20 atoms;

A is a carbon, and R$_5$ and R$_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or A, R5, and R6 are absent;

B is selected from O, S, and NR$_7$, wherein R$_7$ is selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl Z is a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments, the present invention provides compounds having the formula:

wherein:

A is a carbon, or A, R$_5$, and R$_6$ are absent;

R$_1$, R$_2$, R$_5$, and R$_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two substituents selected from R$_1$, R$_2$, R$_5$, and R$_6$, wherein the two substituents are on different carbon atoms, together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; at least one substituent selected from R$_1$, R$_2$, R$_5$, and R$_6$ comprises X-L-, wherein:

X is selected from a reporter molecule, a carrier molecule, a solid phase, or a therapeutic molecule; and L is a group selected from alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, having a chain length of 0-20 atoms;

B is selected from O, S, and NR$_3$, wherein R$_3$ is selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

Z is a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments, when a compound is of Formula (VI), $R_1$, $R_2$, $R_5$, and $R_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or $R_1$ and $R_2$ together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and $R_5$ and $R_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl.

In some embodiments, the present invention provides compounds having the formula:

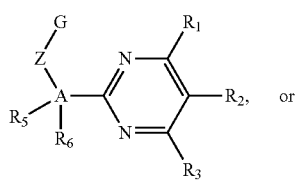
(IX)

or

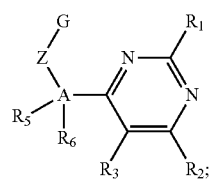
(X)

wherein:

A is a carbon, or A, $R_5$, and $R_6$ are absent;

$R_1$, $R_2$, $R_3$, $R_5$, and $R_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two substituents selected from $R_1$, $R_2$, $R_3$, $R_5$, and $R_6$, wherein the two substituents are on different carbon atoms, together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

at least one substituent selected from $R_1$, $R_2$, $R_3$, $R_5$, and $R_6$ comprises X-L-, wherein:

X is selected from a reporter molecule, a carrier molecule, a solid phase, or a therapeutic molecule; and L is a group selected from alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, having a chain length of 0-20 atoms;

Z is a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments, the present invention provides compounds having the formula:

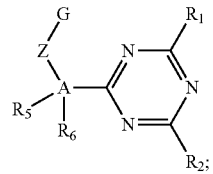
(XI)

wherein:

A is a carbon, or A, $R_5$, and $R_6$ are absent;

$R_1$, $R_2$, $R_5$, and $R_6$ are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; at least one substituent selected from $R_1$, $R_2$, $R_5$, and $R_6$ comprises X-L-, wherein:

X is selected from a reporter molecule, a carrier molecule, a solid phase, or a therapeutic molecule; and L is a group selected from alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, having a chain length of 0-20 atoms;

Z is a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments, the present invention provides compounds having the formula:

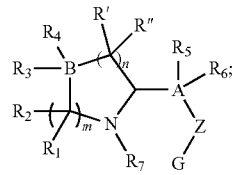
(XII)

wherein:

A is a carbon, or A, $R_5$, and $R_6$ are absent;

m and n is an integer between 4 and 8;

$R_7$ is selected from hydrogen, alkyl, heteroalkyl, substituted alkyl, and substituted heteroalkyl;

$R_1$, $R_2$, $R_3$, $R_4$, $R_5$, $R_6$, each R', and each R" are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two substituents selected from $R_1$, $R_2$, $R_3$, $R_4$, $R_5$, $R_6$, an R', and an R", wherein the two substituents are on different carbon atoms, together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and all of the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl; or two of the remaining substituents also together form a fused moiety selected from cycloalkyl, heterocycloalkyl, substituted cycloalkyl, substituted heterocycloalkyl, aryl, heteroaryl, substituted aryl, arylalkyl, substituted arylalkyl, and substituted heteroaryl, and the remaining substituents are independently selected from hydrogen, halogen, alkyl, heteroalkyl, cycloalkyl, heterocycloalkyl, substituted alkyl, substituted heteroalkyl, substituted cycloalkyl, substituted heterocycloalkyl, alkoxy, substituted alkoxy, aryl, heteroaryl, substituted aryl, arylalkyl, substituted arylalkyl, and substituted heteroaryl;

at least one substituent selected from $R_1$, $R_2$, $R_3$, $R_4$, $R_5$, $R_6$, an R', and an R" comprises X-L-, wherein:

X is selected from a reporter molecule, a carrier molecule, a solid phase, or a therapeutic molecule; and L is a group selected from alkyl, heteroalkyl, cycloalkyl, heterocycloalkyl, alkoxy, substituted alkoxy, substituted alkyl, substituted heteroalkyl, substituted cycloalkyl, substituted heterocycloalkyl, aryl, heteroaryl, substituted aryl, arylalkyl, substituted arylalkyl, and substituted heteroaryl, having a chain length of 0-20 atoms;

Z is a straight- or branched-chain alkyl or heteroalkyl having a chain length of 1-10 atoms, or is absent; and G is a chemical handle selected from an azide-reactive group, an alkyne-reactive group, and a phosphine-reactive group.

In some embodiments of compounds of Formulas (I) to (XIII), one of the R substituents comprises X-L-, and the remaining R substituents are each H. In some embodiments compounds of Formulas (I) to (XIII), L is an alkyl group having a chain length of 0 to 15 atoms, 0 to 10 atoms, or 0 to 5 atoms. In some embodiments compounds of Formulas (I) to (XIII), L is —NH—(CH$_2$)$_n$—NH—C(O)—, wherein n is 1 to 12. In some embodiments, n is 1 to 10, 1 to 8, or 1 to 5.

In some embodiments compounds of Formulas (I) to (XIII), G is an azide or a terminal alkyne. In some embodiments, when a compound of any one of Formulas (I) to (XIII) is to be used in a click reaction, G is an azide or terminal alkyne. In some embodiments, when a compound of any one of Formulas (I) to (XIII) is to be used in a 1,3-dipolar cycloaddition with an activated alkyne, G is an azide. In some embodiments, when a compound of any one of Formulas (I) to (XIII) is to be used in a Staudinger ligation, G is an azide.

In some embodiments, the reporter molecule comprises a chromophore, fluorophore, fluorescent protein, phosphorescent dye, tandem dye, particle, hapten, enzyme, or radioisotope. In some embodiments, the fluorophore is a xanthene, coumarin, cyanine, pyrene, oxazine, borapolyazaindacene, or carbopyranine. In some embodiments, the enzyme is horseradish peroxidase, alkaline phosphatase, beta-galactosidase, or beta-lactamase. In some embodiments, the particle is a semiconductor nanocrystal.

In some embodiments, the carrier molecule is an amino acid, peptide, protein, polysaccharide, nucleoside, nucleotide, oligonucleotide, nucleic acid, hapten, psoralen, drug, hormone, lipid, lipid assembly, tyramine, synthetic polymer, polymeric microparticle, biological cell, cellular component, ion chelating moiety, enzymatic substrate, or virus. In some embodiments, the carrier molecule is an antibody, antibody fragment, antigen, avidin, streptavidin, biotin, dextran, IgG binding protein, fluorescent protein, agarose, or non-biological microparticle.

In some embodiments, the solid support is an aerogel, hydrogel, resin, bead, biochip, microfluidic chip, silicon chip, multi-well plate, membrane, conducting metal, non-conducting metal, glass, or magnetic support. In some embodiments, the solid support is a silica gel, polymeric membrane, particle, derivatized plastic film, glass bead, cotton, plastic bead, alumina gel, polysaccharide, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene, nylon, latex bead, magnetic bead, paramagnetic bead, superparamagnetic bead, or starch.

In some embodiments, the therapeutic molecule is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, or analogs or homologs thereof. In some embodiments, the therapeutic molecule is an antimetabolite, alkylating agent, anthracycline, antibiotic, or anti-mitotic agent. In some embodiments, the therapeutic molecule is abrin, ricin A, pseudomonas exotoxin, diphtheria toxin, tumor necrosis factor, γ-interferon, α-interferon, nerve growth factor, platelet derived growth factor, tissue plasminogen activator, interleukin-1, interleukin-2, interleukin-6, granulocyte macrophage colony stimulating factor, or granulocyte colony stimulating factor.

Figure 1B:
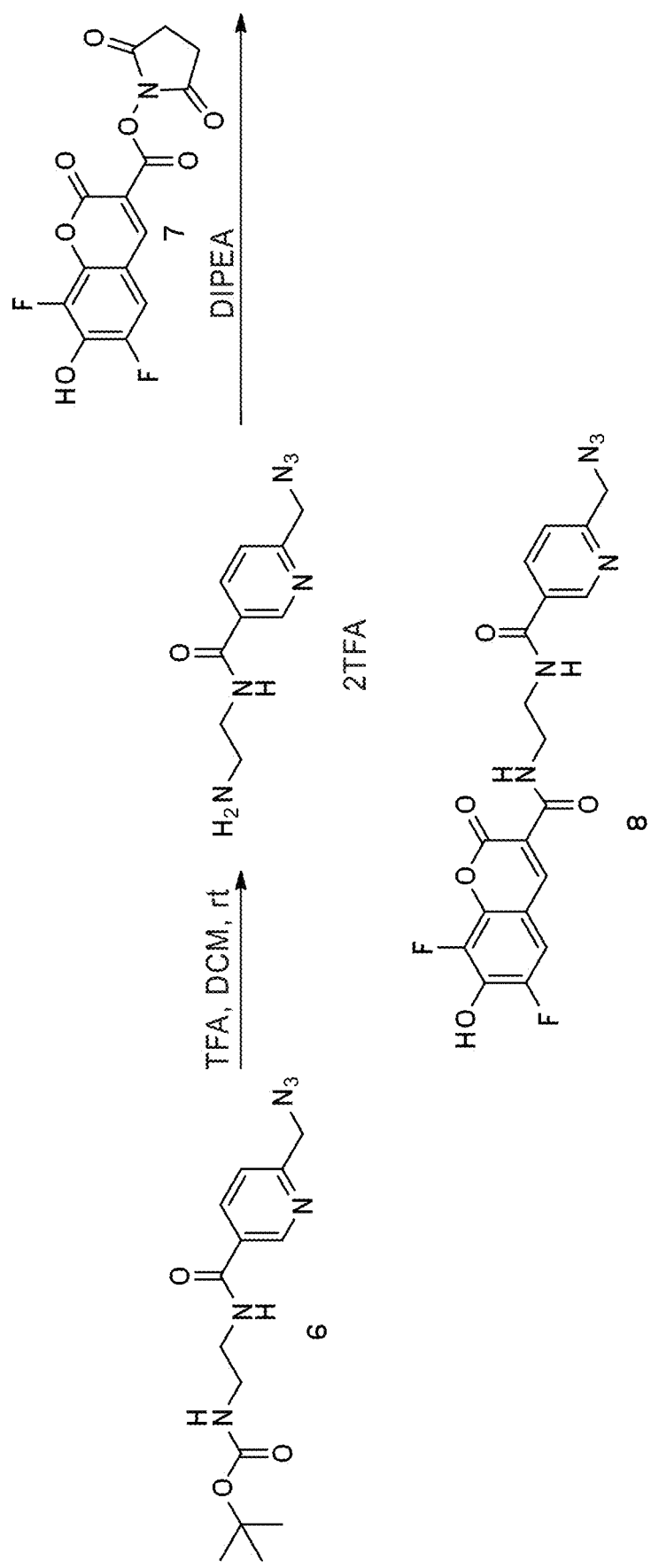
Figure 2:
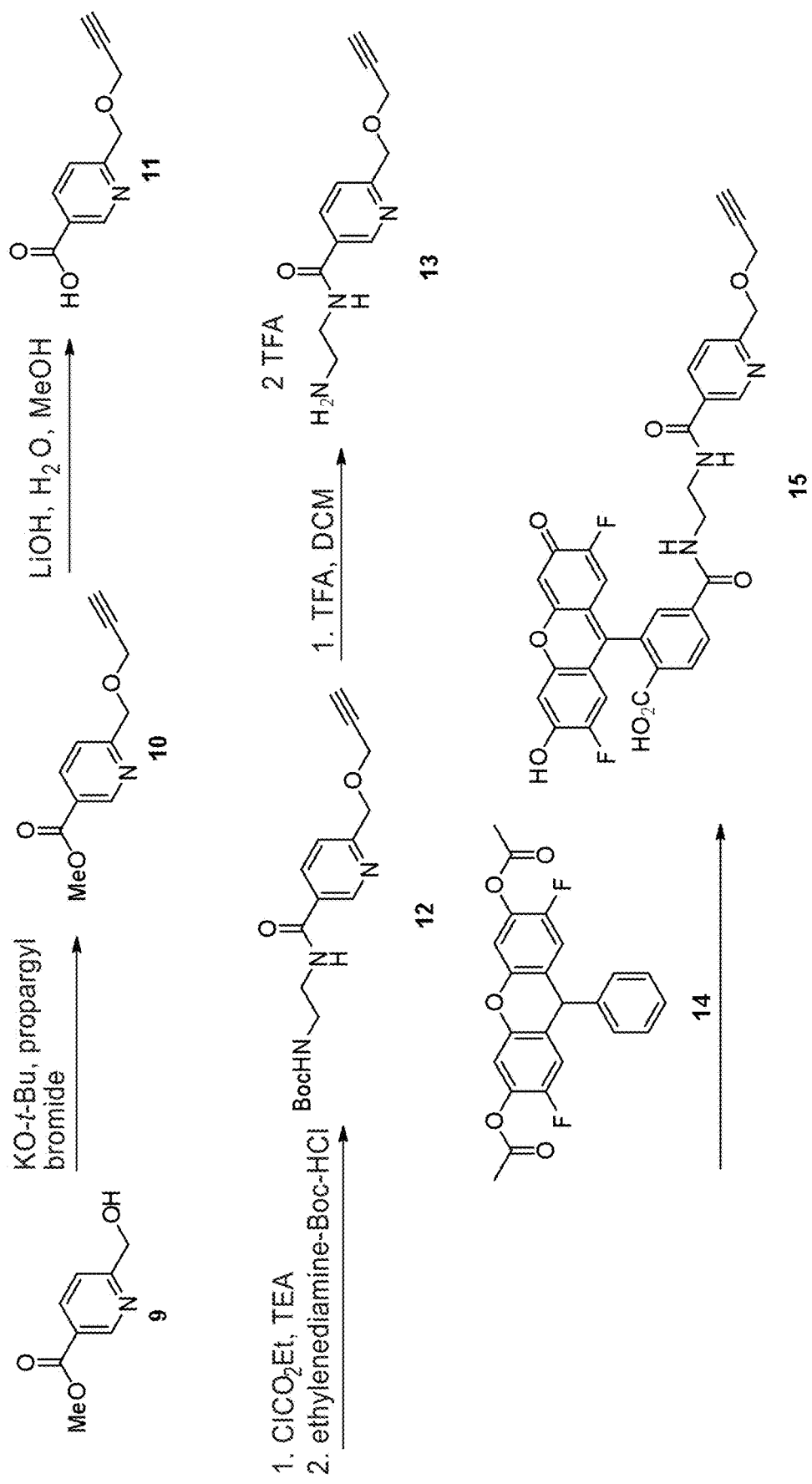
FIG. 2 shows a reaction scheme for the synthesis of tert-butyl (2-(6-((prop-2-yn-1-yloxy)methyl)nicotinamido) ethyl)carbamate (12), and fluorescent labeling of compound (12), as described in Example 1.

The compounds of the present invention may be made, for example, using the exemplary reaction schemes shown in FIG. 1 and FIG. 2, and described in Example 1.

Reporter Molecules

In some embodiments, a compound of any one of Formulas (I) to (XIII) comprises a reporter molecule. The reporter molecules used in the methods and compositions provided herein include any directly or indirectly detectable reporter molecule that can be covalently attached as a substituent of a compound of any one of Formulas (I) to (XIII).

Reporter molecules used in the methods and compositions described herein include, but are not limited to, chromophores, fluorophores, fluorescent proteins, phosphorescent dyes, tandem dyes, particles, haptens, enzymes, and radioisotopes. In some embodiments, a reporter molecule is a fluorophore, a fluorescent protein, a hapten, or an enzyme.

A fluorophore is any chemical moiety that exhibits an absorption maximum at wavelengths greater than 280 nm, and retains its spectral properties when covalently attached to a biomolecule following reaction of a compound of any one of Formulas (I) to (XIII) comprising the fluorophore with the modified biomolecule. Fluorophores include, without limitation, pyrenes; anthracenes; naphthalenes; acridines; stilbenes; indoles and benzindoles; oxazoles and benzoxazoles; thiazoles and benzothiazoles; 4-amino-7-nitrobenz-2-oxa-1,3-diazoles (NBD); cyanines; carbocyanines; carbostyryls; porphyrina; salicylates; anthranilates; azulenes; perylenes; pyridines; quinolines; borapolyazaindacenes; xanthenes (including, but not limited to, fluoresceins (such as benzo- or dibenzofluoresceins, seminaphthofluoresceins, or naphthofluoresceins), rhodols (such as eminaphthorhodafluors), and rhodamine); oxazines and benzoxazines (including, but not limited to, resorufins, aminooxazinones, diaminooxazines, and their benzo-substituted analogs); carbazines; phenalenones; coumarins; benzofurans; benzphenalenones; carbopyranines, semiconductor nanocrystals; and derivatives of any of the above.

In some embodiments, a reporter molecule is selected from a xanthene (including, but not limited to, sulfonated xanthenes, fluorinated xanthenes, rhodol, rhodamine, fluorescein and derivatives thereof), coumarin (including, but not limited to, sulfonated coumarin and fluorinated coumarin), cyanine (including, but not limited to, sulfonated cyanine), pyrene, oxazine, borapolyazaindacene, carbopyranine, and semiconductor nanocrystal.

In some embodiments, a reporter molecule is a xanthene that is bound as a substituent of a compound of any one of Formulas (I) to (XIII) via a single covalent bond at the 9-position of the xanthene. In some embodiments, the xanthene is selected from 3H-xanthen-6-ol-3-one attached through the 9-position, 6-amino-3H-xanthen-3-one attached through the 9-position, and 6-amino-3H-xanthen-3-imine attached through the 9-position.

One skilled in the art can select a fluorophore to be included as a substituent of a compound of any one of Formulas (I) to (XIII) according to the particular application. Physical properties of a fluorophore that can be used for detection of modified biomolecules include, but are not limited to, spectral characteristics (absorption, emission, and stokes shift), fluorescence intensity, lifetime, polarization and photo-bleaching rate, and combinations thereof. In various embodiments, one or more of the physical properties can be used to distinguish one fluorophore from another, and thereby allow for multiplexed analysis. In some embodiments, the fluorophore has an absorption maximum at wavelengths greater than 480 nm, at wavelengths between 488 nm to 514 nm (particularly suitable for excitation by the output of the argon-ion laser excitation source), or at wavelengths near 546 nm (particularly suitable for excitation by a mercury arc lamp).

Many of fluorophores can also function as chromophores and thus the described fluorophores may also be used as chromophore reporter molecules in the methods and compositions described herein.

In some embodiments, a reporter molecule is an enzyme. In some embodiments, an enzyme is a desirable label because it can amplify the detectable signal, thus increasing assay sensitivity. In some embodiments, the enzyme itself is not directly detectable, but its activity can be used to create a detectable signal when the enzyme is contacted with an appropriate substrate, such that the converted substrate produces, for example, a fluorescent, colorimetric, or luminescent signal. Various substrates are known in the art, some of which are described in the Molecular Probes Handbook, supra.

In some embodiments, when an enzyme reporter molecule is an oxidoreductase such as, by way of example only, horseradish peroxidase, suitable substrates include, but are not limited to, 3,3'-diaminobenzidine (DAB) or 3-amino-9-ethylcarbazole (AEC), 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol, 4-hydroxy-3-methoxyphenylacetic acid, reduced phenoxazines and reduced benzothiazines, including Amplex® Red reagent and its variants (U.S. Pat. No. 4,384,042), Amplex UltraRed and its variants (WO05/042504), reduced dihydroxanthenes, including dihydrofluoresceins and dihydrorhodamines, including dihydrorhodamine 123. Peroxidase substrates that may be used with the enzymatic reporter molecules described herein also include, but are not limited to, tyramides (U.S. Pat. Nos. 5,196,306; 5,583,001 and 5,731,158), which can be intrinsically detectable before action of the enzyme but are "fixed in place" by the action of a peroxidase in the process described as tyramide signal amplification (TSA). In various embodiments, such substrates may be used, for example, to label targets in samples that are cells, tissues or arrays for their subsequent detection by microscopy, flow cytometry, optical scanning and fluorometry.

In some embodiments, when an enzyme reporter molecule is a phosphatase enzyme such as, by way of example only, an acid phosphatases or an alkaline phosphatase, suitable substrates include, but are not limited to, 5-bromo-6-chloro-3-indolyl phosphate (BCIP), 6-chloro-3-indolyl phosphate, 5-bromo-6-chloro-3-indolyl phosphate, p-nitrophenyl phosphate, and o-nitrophenyl phosphate. Nonlimiting fluorogenic substrates include, but are not limited to, 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), ELF 97, ELF 39, and related phosphates (U.S. Pat. Nos. 5,316,906 and 5,443,986).

In some embodiments, when an enzyme reporter molecule is a glycosidase such as, by way of example only, a beta-galactosidase, beta-glucuronidase, or beta-glucosidase, suitable substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG), p-nitrophenyl beta-D-galactopyranoside, resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside, and fluorinated coumarin beta-D-galactopyranosides.

Enzyme reporter molecules also include, but are not limited to, hydrolases such as cholinesterases and peptidases, oxidases such as glucose oxidase and cytochrome oxidases, and reductases, for which suitable substrates are known. Additional nonlimiting exemplary enzyme reporter molecules include luciferases and aequorins. In addition, the chemiluminescence-producing substrates for phosphatases, glycosidases and oxidases such as those containing stable dioxetanes, luminol, isoluminol and acridinium esters can also be used with the enzyme reporter molecules described herein.

In some embodiments, a reporter molecule is a hapten. Nonlimiting exemplary haptens include hormones, naturally occurring and synthetic drugs, pollutants, allergens, affector molecules, growth factors, chemokines, cytokines, lymphokines, amino acids, peptides, chemical intermediates, nucleotides, biotin and the like. In some embodiments, a hapten is not directly detectable, but it can bind to another molecule that is detectable. As a nonlimiting example, a hapten may be an antigen that can be bound by an antibody specific to that antigen, wherein the antibody comprises a detectable label, or wherein the antibody can be bound by a secondary antibody comprising a detectable label.

In some embodiments, a reporter molecule is a fluorescent protein. Nonlimiting exemplary fluorescent proteins include green fluorescent protein (GFP) and the phycobiliproteins and derivatives thereof. In some embodiments, a fluorescent protein is used in conjunction with a fluorophore in order to obtain a larger stokes shift from the fluorescent protein's absorption spectra. In some embodiments, the fluorescent protein and fluorophore function as an energy transfer pair, wherein the fluorescent protein emits at the wavelength at which the fluorophore absorbs and the fluorophore then emits at a wavelength farther from the fluorescent protein's emission wavelength than could have been obtained with only the fluorescent protein. In some such embodiments, a compound of any one of Formulas (I) to (XIII) comprises a fluorescent protein as one substituent and a fluorophore as another substituent. In some embodiments, a compound of any one of Formulas (I) to (XIII) comprises both the fluorescent protein and the fluorophore as a single substituent, wherein the fluorescent protein and the fluorophore are connected to one another by a linker. Nonlimiting exemplary fluorescent protein/fluorophore pairs include phycobiliproteins and sulforhodamine fluorophores, sulfonated cyanine fluorophores, or sulfonated xanthene fluorophores. In some embodiments, the fluorophore functions as the energy donor and the fluorescent protein as the energy acceptor. Nonlimiting exemplary radioisotopes that may be used as reporter molecules include For example, the compounds may be radiolabeled with radioactive isotopes, such as for example tritium ($^3$H), iodine-125 ($^{125}$I) or carbon-14 ($^{14}$C), sulfur-35 ($^{35}$S), etc. All isotopic variations of the compounds of the present invention, whether radioactive or not, are intended to be encompassed within the scope of the present invention.

Methods of attaching reporter molecules as substituents of compounds of Formulas (I) to (XIII) are known in the art. Nonlimiting exemplary methods include the methods shown in FIGS. 1 and 2, in which a reporter molecule comprising an N-hydroxysuccinimidyl (NHS) ester is reacted with a precursor of a compound of any one of Formulas (I) to (XIII) bearing a primary amine on at least one substituent. SDP esters, TFP, PFP, carbamates, thiocarbamates and maleimides may also be used in place of NHS esters.

Carrier Molecules

In some embodiments, a compound of any one of Formulas (I) to (XIII) comprises a carrier molecule as a substituent.

Carrier molecules include, but are not limited to, antigens, steroids, vitamins, drugs, haptens, metabolites, toxins, environmental pollutants, amino acids, peptides, proteins, nucleic acids, nucleic acid polymers, carbohydrates, lipids, and polymers. In some embodiments, a carrier molecule comprises an amino acid, a peptide, a protein, an antibody or fragment thereof, an antigen, avidin, streptavidin, biotin, a dextran, an IgG binding protein (such as protein A or protein G), agarose, a polysaccharide, a nucleoside, a nucleotide, an oligonucleotide, a nucleic acid, a hapten, a psoralen, a drug, a hormone, a lipid, a lipid assembly, a synthetic polymer, a non-biological microparticle (such as a polymeric microparticle), an ion chelating moiety, an enzymatic substrate, a biological cell, a cellular component, a virus, or combinations thereof.

In some embodiments, when the carrier molecule is an enzymatic substrate, the enzymatic substrate is selected from an amino acid, a peptide, a sugar, an alcohol, alkanoic acid, 4-guanidinobenzoic acid, a nucleic acid, a lipid, sulfate, phosphate, —CH$_2$OCO-alkyl, and combinations thereof. In certain embodiments, such enzyme substrates can be cleaved by enzymes selected from peptidases, phosphatases, glycosidases, dealkylases, esterases, guanidinobenzotases, sulfatases, lipases, peroxidases, histone deacetylases, exonucleases, reductases, endoglycoceramidases and endonucleases.

In some embodiments, when the carrier molecule comprises an amino acid, a peptide, or protein, the carrier molecule is selected from a neuropeptide, a cytokine, a toxin, a protease substrate, and a protein kinase substrate. In some embodiments, a carrier is a peptide that functions as an organelle localization peptide, that is, a peptide that serves to target the conjugated compound for localization within a particular cellular substructure by cellular transport mechanisms, including, but not limited to, a nuclear localization signal sequence.

In some embodiments, a carrier molecule is a protein selected from an enzyme, an antibody, a lectin, a glycoprotein, a histone, an albumin, a lipoprotein, protein A, protein G, a phycobiliprotein or other fluorescent protein, a hormone, a toxin, and a growth factor. In some embodiments, a carrier molecule is a protein selected from an antibody, an antibody fragment, avidin, streptavidin, a toxin, a lectin, or a growth factor. In some embodiments, a carrier molecule comprises a hapten such as, for example, biotin, digoxigenin, or a fluorophore.

In some embodiments, a carrier molecule comprises a nucleic acid base, nucleoside, nucleotide or a nucleic acid polymer, a peptide nucleic acid (PNA), or a locked nucleic acid (LNA), single- or multi-stranded, natural or synthetic DNA or RNA oligonucleotide, or DNA/RNA hybrid, optionally containing an additional linker or spacer for attachment of a fluorophore or other ligand. In some embodiments, a nucleic acid carrier molecule (including, but not limited to, LNA, PNA, DNA, and RNA) comprises fewer than 50 nucleotides, or fewer than 25 nucleotides.

In some embodiments, a carrier molecule comprises a carbohydrate or polyol, including a polysaccharide, such as dextran, FICOLL, heparin, glycogen, amylopectin, mannan, inulin, starch, agarose and cellulose, or a polymer such as a poly(ethylene glycol). In some embodiments, a carrier molecule comprises dextran, agarose, or FICOLL.

In some embodiments, a carrier molecule comprises a lipid including, but not limited to, glycolipids, phospholipids, and sphingolipids. In some embodiments, such lipids contain 6-25 carbons. In some embodiments, a carrier molecule includes a lipid vesicle, such as a liposome, or is a lipoprotein. Some lipophilic substituents are useful, in some embodiments, for facilitating transport of a conjugated molecule into cells or cellular organelles.

In some embodiments, a carrier molecule is a cell, cellular fragment, or subcellular particle, including virus particles, bacterial particles, virus components, biological cells (such as animal cells, plant cells, bacteria, or yeast), or cellular components. Non-limiting examples of such cellular components include lysosomes, endosomes, cytoplasm, nuclei, histones, mitochondria, Golgi apparatus, endoplasmic reticulum and vacuoles.

In some embodiments, a carrier molecule comprises a specific binding pair member. In some such embodiments, the presence of the carrier molecule, and therefore the biomolecule to which it is conjugated through a compound of any one of Formulas (I) to (XIII), can be detected using a complementary specific binding pair member comprising a detectable label. Nonlimiting exemplary binding pairs are set forth in Table 2.

TABLE 2

Exemplary Specific Binding Pairs

| Antigen | Antibody |
| --- | --- |
| Biotin | avidin (or streptavidin or anti-biotin) |
| IgG* | protein A or protein G |
| Drug | drug receptor |
| Folate | folate binding protein |
| Toxin | toxin receptor |
| Carbohydrate | lectin or carbohydrate receptor |
| Peptide | peptide receptor |
| Protein | protein receptor |
| enzyme substrate | Enzyme |
| DNA (RNA) | cDNA (cRNA)† |
| Hormone | hormone receptor |
| Ion | Chelator |

*IgG is an immunoglobulin
†cDNA and cRNA are the complementary strands used for hybridization In some embodiments, a carrier molecule is an antibody-binding moiety, such as, but not limited to, anti-Fc, an anti-Fc isotype, anti-J chain, anti-kappa light chain, anti-lambda light chain, or a single-chain fragment variable protein, an anti-Fc Fab fragment; or a non-antibody peptide or protein, such as, for example but not limited to, soluble Fc receptor, protein G, protein A, protein L, lectins, or a fragment thereof.

Methods of attaching carrier molecules as substituents of compounds of Formulas (I) to (XIII) are known in the art. Nonlimiting exemplary methods include as examples amides, thioamides, ethers, thioethers, carbamates, thiocarbamates, sulfhydryl groups, amino groups, etc.

Solid Supports

In some embodiments, a compound of any one of Formulas (I) to (XIII) comprises a solid support as a substituent.

A large number of solid supports are known in the art and can be used, in some embodiments, as a substituent of a compound of any one of Formulas (I) to (XIII). Nonlimiting exemplary solid supports include solid and semi-solid matrixes, such as aerogels and hydrogels, resins, beads, biochips (including thin film coated biochips), microfluidic chip, a silicon chip, multi-well plates (also referred to as microtiter plates or microplates), membranes, conducting and nonconducting metals, glass (including microscope slides) and magnetic supports. Other nonlimiting examples of solid supports include silica gels, polymeric membranes, particles, derivatized plastic films, derivatized glass, derivatized silica, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In some embodiments, the solid supports used in the methods and compositions described herein are substantially insoluble in liquid phases.

In some embodiments, a solid support may comprise a reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, azide, alkyne, or phosphine, wherein such functional groups are used to covalently attach the solid support to a precursor of a compound of any one of Formulas (I) to (XIII).

A suitable solid phase support used in the methods and compositions described herein, can be selected on the basis of desired use. By way of example only, where amide bond formation is desirable to attach the precursor of a compound of any one of Formulas (I) to (XIII) to the solid support, resins generally useful in peptide synthesis may be employed, such as polystyrene, POLYHIPE™ resin, polyamide resin, polystyrene resin grafted with polyethylene glycol, polydimethyl-acrylamide resin, or PEGA beads. In some embodiments, precursors to compounds of Formulas (I) to (XIII) are deposited onto a solid support in an array format. In some such deposition is accomplished by direct surface contact between the support surface and a delivery mechanism, such as a pin or a capillary, or by ink jet technologies which utilize piezoelectric and other forms of propulsion to transfer liquids from miniature nozzles to solid surfaces.

Modified Biomolecules

The modification of biomolecules to incorporate chemical handles allows chemical attachment of another moiety (such as a reporter molecule or solid support) through a subsequent click reaction. In some embodiments, the chemical handle of the modified biomolecule is selected from azide, alkyne (such as a terminal alkyne or an activated alkyne), and phosphine. In some embodiments, a biomolecule is modified in vivo, for example, using cellular biosynthetic pathways, such as, for example, glycosylation of proteins, DNA replication, or transcription of RNA. In some embodiments, a biomolecule is modified in vivo by contacting a cell with a reagent that modifies a particular biomolecule or class of biomolecules. In some embodiments, a biomolecule is modified in vitro using a reagent that modifies a biomolecule.

Various methods and reagents for modifying biomolecules in vivo are known in the art. For example, in some embodiments, glycoproteins may be modified in vivo by contacting a cell with non-native glycans that comprise chemical handles. The non-native glycans are used by the cell to glycosylate glycoproteins, resulting in covalent attachment of chemical handles to such glycoproteins. Nonlimiting exemplary non-native glycans that may be used to modify glycoproteins with chemical handles include tetraacetylated N-azidoacetylglucosamine, tetraacetylated N-azidoacetylgalactosamine, tetraacetylated N-azidoacetylmannosamine, and tetraacetylfucose alkyne.

In some embodiments, a protein may be modified by incorporating non-native amino acids comprising chemical handles. Such modification may occur in vivo, during protein synthesis, or in an in vitro protein translation system. Nonlimiting exemplary non-native amino acids that may be used to modify proteins with chemical handles include, but are not limited to, 4-azido-L-phenylalanine, L-azidohomoalanine, and L-homopropargylglycine.

In some embodiments, a prenylated protein may be modified, for example, by contacting a cell with a farnesyl alcohol azide or a geranylgeranyl alcohol azide.

In some embodiments, a protein may be modified during fatty acid acylation of the protein, for example, by contacting a cell with a non-native fatty acid comprising a chemical handle. Nonlimiting exemplary non-native fatty acids that may be used to modify proteins with chemical handles include, but are not limited to, palmitic acid azide, myristic acid azide, and the fatty acid analogs described, e.g., in International Application No. PCT/US10/61768.

In some embodiments, DNA may be modified in vivo or in vitro using various non-native nucleoside triphosphates that comprise chemical handles. In some embodiments, the DNA is modified during replication through incorporation of a non-native nucleoside by DNA polymerase. In some embodiments, the DNA is modified during apoptosis through incorporation of a non-native nucleoside by terminal nucleotidyl transferase (TdT). Nonlimiting exemplary such non-native nucleoside triphosphates include C-8-alkyne-dUTP and/or C8-alkyne-dCTP. Following incorporation, the DNA comprises one or more covalently attached alkyne groups. In some embodiments, DNA may be modified during chemical DNA synthesis using, for example, phophoramidites comprising chemical handles.

In some embodiments, RNA may be modified in vivo or in vitro using various non-native nucleoside triphosphates that comprise chemical handles. In some embodiments, the RNA is modified during replication through incorporation of a non-native nucleoside by RNA polymerase. Nonlimiting exemplary such non-native nucleoside triphosphates include C-8-alkyne-UTP and/or C8-alkyne-CTP. Following incorporation, the RNA comprises one or more covalently attached alkyne groups. In some embodiments, RNA may be modified during chemical RNA synthesis using, for example, phophoramidites comprising chemical handles.

In some embodiments, a biomolecule may be modified in vitro using a reagent that covalently attaches a chemical handle through a particular group on the biomolecule. For example, in some embodiments, a biomolecule that comprises a primary amine (—$NH_2$) may be modified using a reagent such as NHS-azide, NHS-phosphine, and sulfo-NHS-phosphine, SDP-azide, TFP-azide, PFP-azide, carbamate-azide, thiocarbamate-azide and maleimide-azide may also be used in place of NHS-azides.

Copper Ion Sources

In some embodiments, a click reaction comprises a copper ion source that provides Cu(I) ions. In some embodiments, a copper ion source provides Cu(I) ions in the presence of a reducing agent. In some such embodiments, a copper ion source provides Cu(II) ions, which are reduced to Cu(I) ions in the presence of a reducing agent. Nonlimiting exemplary copper ion sources that produce Cu(I) ions include CuBr, CuI, tetrakis(acetonitrile)Cu(I) hexafluorophosphate, tetrakis(acetonitrile)Cu(I) tetrafluoroborate, tetrakis(acetonitrile)Cu(I) triflate, CuCN, Cu(I) butanethiolate, Cu(I) thiophenolate, Cu(I) triflate. In some embodiments, a copper ion source that produces Cu(I) ions is included in a click reaction at a concentration between 0.01 mM and 10 mM, between 0.01 mM and 5 mM, between 0.05 mM and 5 mM, between 0.1 mM and 5 mM, between 0.5 mM and 5 mM, between 0.5 mM and 4 mM, or between 0.5 mM and 3 mM. Nonlimiting exemplary copper ion sources that produce Cu(II) ions include Cu(NO$_3$)$_2$ Cu(OAc)$_2$ or CuSO$_4$, metallic Cu and metallic Cu with sonication. In some embodiments, a copper ion source that produces Cu(II) ions is included in a click reaction at a concentration between 0.01 mM and 10 mM, between 0.01 mM and 5 mM, between 0.05 mM and 5 mM, between 0.1 mM and 5 mM, between 0.5 mM and 5 mM, between 0.5 mM and 4 mM, or between 0.5 mM and 3 mM.

In some embodiments, a copper ion source is copper-containing metal, such as copper wire.

Nonlimiting exemplary reducing agents that may be used to reduce Cu(II) ions to Cu(I) ions include ascorbate, tris(2-carboxyethyl) phosphine (TCEP), NADH, NADPH, thiosulfate, metallic copper, hydroquinone, vitamin K$_1$, glutathione, cysteine, 2-mercaptoethanol, and dithiothreitol. Nonlimiting exemplary metals that may act as reducing agents include Al, Be, Co, Cr, Fe (including Fe$^{2+}$), Mg, Mn, Ni, Zn, Au, Ag, Hg, Cd, Zr, Ru, Fe, Co (including Co$^{2+}$), Pt, Pd, Ni, Rh, and W. In some embodiments, a reducing agent is included in a click reaction at a concentration 1 micromolar to 5 molar.

In some embodiments, a reducing agent is an applied electric potential. In this case, a ligand such as TBTA, THPTA, benxzimidazole, BCS, etc is used employed and an electric potential of −30 to −300 mV is applied in a two compartment cell using a combination of working and reference electrodes. Standard buffers can be used (HEPES, Tris, etc) and the electric potential may be applied during the course of the reaction. See *ChemBioChem* 2008, 9, 1481-1486. for further details and experimental information.

Copper Ion Chelators

Without limitation to any specific mechanism, it is known that copper can promote the cleavage of biomolecules, such as proteins and nucleic acids. The addition of a copper chelator in a click reaction may reduce the detrimental effects of copper, thereby preserves the structural integrity of biomolecules.

In some embodiments, a click reaction comprises a copper chelator. In some embodiments, a copper chelator stabilizes Cu(I) ions against oxidation, precipitation, and/or disproportionation. By including a copper chelator, in some embodiments, a lower concentration of copper ions can be used in a click reaction to achieve the same efficiency as would be obtained in the presence of higher concentrations of copper ions in the absence of a chelator.

Nonlimiting exemplary copper ion chelators include compounds of formula (V):

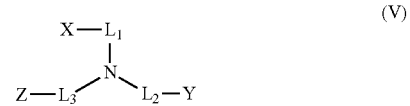

wherein X, Y, and Z each independently have the formula:

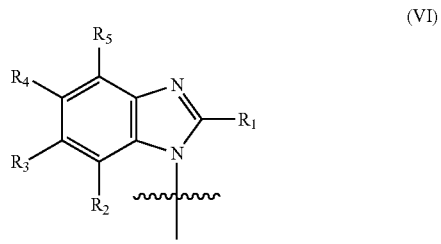

wherein:
R$_1$, R$_2$, R$_3$, R$_4$ and R$_5$ are independently selected from hydrogen, halogen, alkyl, heteroalkyl, alkoxy, cycloalkyl, heterocycloalkyl, substituted alkyl, substituted heteroalkyl, substituted alkoxy, substituted cycloalkyl, substituted heterocycloalkyl, aryl, heteroaryl, substituted aryl, arylalkyl, substituted arylalkyl, and substituted heteroaryl; and
L$_1$, L$_2$, and L$_3$ are independently selected from alkyl, heteroalkyl, substituted alkyl, and substituted heteroalkyl, having a chain length of 1-5 atoms.

In some embodiments, $R_1$, $R_2$, $R_3$, $R_4$ and $R_5$ for at least one substituent selected from X, Y, and Z are each H. In some embodiments, $L_1$, $L_2$ and $L_3$ are each alkyl groups having a chain length of 1-5 atoms. In some embodiments, $L_1$, $L_2$ and $L_3$ are each —$CH_2CH_2$—.

Nonlimiting exemplary copper ion chelators also include 1,10 phenanthroline-containing copper (I) chelators, such as, for example, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). Nonlimiting exemplary chelators also include tris-(hydroxypropyltriazolylmethyl) amine (THPTA; see, e.g., Jentzsch et al., *Inorganic Chemistry*, 48(2): 9593-9595 (2009)) and the Cu(I) chelators described in U.S. Publication No. US2010/0197871, the disclosure of which is incorporated herein by reference. Nonlimiting exemplary chelators also include N-(2-acetamido)iminodiacetic acid (ADA), pyridine-2,6-dicarboxylic acid (PDA), S-carboxymethyl-L-cysteine (SCMC), trientine, tetra-ethylenepolyamine (TEPA), N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), and derivatives thereof. In some embodiments, histidine is used as a chelator. In some embodiments, glutathione is used as a chelator and a reducing agent.

In some embodiments, a copper chelator, such as a compound of formula (V), is included in a click reaction at molar ratio of 1:1, 2:1, 3:1, 4:1, 5:1, 6:1, 7:1, 8:1, 9:1, 10:1, or greater than 10:1, relative to the concentration of copper in the click reaction. That is, in some embodiments, if copper is included in a click reaction at a concentration of 2 mM, a copper chelator, such as a compound of formula (V), may be included in the click reaction at a concentration of 2 mM (1:1), 4 mM (2:1), 6 mM (3:1), etc. In some embodiments, the concentration of a copper chelator, such as a compound of formula (V), in a click reaction is between 1 μM and 100 mM, between 10 μM and 10 mM, between 50 μM and 10 mM, or between 1 mM and 10 mM.

Compositions

In some embodiments, compositions are provided. In some embodiments, a composition comprises a compound of any one of Formulas (I) to (XIII). In some embodiments, a composition comprises a compound of any one of Formulas (I) to (XIII) and a modified biomolecule. In some such embodiments, the compound of any one of Formulas (I) to (XIII) comprises an azide and the biomolecule comprises an alkyne, such as a terminal alkyne or an activated alkyne, or a phosphine, such as a triarylphosphine. In some embodiments, the compound of any one of Formulas (I) to (XIII) comprises an alkyne and the biomolecule comprises an azide.

In some embodiments, a composition comprises a first compound of any one of Formulas (I) to (XIII) and a second compound of any one of Formulas (I) to (XIII), wherein the first and second compounds of Formulas (I) to (XIII) are distinguishable from one another. For example, in some embodiments, the first compound of any one of Formulas (I) to (XIII) comprises a first reporter molecule and the second compound of any one of Formulas (I) to (XIII) comprises a second reporter molecule, wherein the first and second reporter molecules are detectably different. In some embodiments, the first compound of any one of Formulas (I) to (XIII) comprises an alkyne and the second compound of any one of Formulas (I) to (XIII) comprises an azide. In some such embodiments, the composition comprises a first biomolecule comprising an alkyne reactive group and a second biomolecule comprising an azide reactive group. In some embodiments, a composition comprise three, four, five, or more compounds of Formulas (I) to (XIII). In some such embodiments, the compounds of Formulas (I) to (XIII) in a composition can each be independently detected. That is, in some embodiments, two or more of the compounds comprise detectably different reporter molecules and/or can be separated from one another prior to detection, etc.

In some embodiments, a composition further comprises a copper ion source and/or a reducing agent and/or a copper ion chelator. In some such embodiments, the copper ion chelator is a compound of formula (V).

Various buffering agents can be included in the compositions described herein, including inorganic and organic buffering agents. In some embodiments buffering agent is a zwitterionic buffering agent. Exemplary buffering agents include phosphate (such as, for example, in phosphate buffered saline (PBS)), succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl] amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl) amino-methane (Tris), TRIS-Acetate-EDTA (TAE), glycine, bis[2-hydroxyethyl]iminotris[hydroxymethyl]methane (BisTris), and combinations thereof. In some embodiments, a composition further comprises ethylene diamine tetraacetic acid (EDTA).

The concentration of such buffering agents in a composition, in some embodiments, is between 0.1 mM and 1 M, between 10 mM and 1 M, between 20 mM and 500 mM, between 50 mM and 300 mM, between 0.1 mM and 50 mM, and between 0.5 mM and 20 mM.

One skilled in the art can select a suitable composition pH according to the intended application. In order to retain the structural integrity of biomolecules, in some embodiments, the pH is maintained in a physiological range, such as, for example, between about 6.5 and 8. In some embodiments, a composition has a pH of between 5 and 9 at 25° C., between 6 and 8.5 at 25° C., between 6 and 8 at 25° C., between 6.5 and 8 at 25° C., or between 6.5 and 7.5 at 25° C.

In some embodiments, a composition comprises one or more non-ionic detergents. Non-limiting examples of such non-ionic detergents include polyoxyalkylene diols, ethers of fatty alcohols (such as alcohol ethoxylates), alkyl phenol ethoxylates, ethylene oxide/propylene oxide block copolymers, polyoxyethylene ester of a fatty acids, alkyl phenol surfactants, polyoxyethylene mercaptan analogs of alcohol ethoxylates, polyoxyethylene adducts of alkyl amines, polyoxyethylene alkyl amides, sorbitan esters, and alcohol phenol ethoxylate. Non-limiting examples of sorbitan esters include polyoxyethylene(20) sorbitan monolaurate (TWEEN20), polyoxyethylene(20) sorbitan monopalmitate (TWEEN40), polyoxyethylene(20) sorbitan monostearate (TWEEN60) and polyoxyethylene(20) sorbitan monooleate (TWEEN 80). In some embodiments, the concentration of such non-ionic detergents in a composition is between 0.005 and 0.5%, between 0.01 and 0.4%, between 0.01 and 0.3%, between 0.01 and 0.2%, or between 0.01 and 0.2%.

Conjugation of Modified Biomolecules

In various embodiments, the modified biomolecules described herein may be linked to at least one moiety selected from a reporter molecule, a carrier molecule, a solid phase, and a therapeutic molecule, by conjugating the modified biomolecule to a compound of any one of Formulas (I) to (XIII) using a click reaction, a 1,3-dipolar cycloaddition reaction, or Staudinger ligation reaction. In some embodiments, the reaction is carried out at room temperature in aqueous solution.

In some embodiments, a click reaction is carried out in the presence of copper, such as Cu(I) ions. In some embodiments, a click reaction is carried out in the presence of a reducing agent. In some embodiments, the click reaction is carried out in the presence of a copper chelator. In some embodiments, the resulting conjugated product is stable in an aqueous environment for sufficient time to allow manipulation, quantification, and/or detection of the biomolecule.

In some embodiments, the modified biomolecule comprises an azide moiety. In some such embodiments, the compound of any one of Formulas (I) to (XIII) comprises a terminal alkyne at substituent G. In some embodiments, the modified biomolecule comprises an alkyne moiety, such as a terminal alkyne or an activated alkyne. In some such embodiments, the compound of any one of Formulas (I) to (XIII) comprises an azide at substituent G. In some embodiments, the modified biomolecule comprises a phosphine moiety, such as a triarylphosphine. In some such embodiments, the compound of any one of Formulas (I) to (XIII) comprises an azide at substituent G.

In some embodiments, the click reaction, 1,3-dipolar cycloaddition reaction, or Staudinger ligation reaction is carried out in a cell, in a cell lysate, in a solution comprising an isolated modified biomolecule, or with a modified biomolecule immobilized on a solid support.

In some embodiments, a modified biomolecule comprises more than one type of chemical handle. As a nonlimiting example, in some embodiments, a modified biomolecule comprises an azide and an alkyne, such as a terminal alkyne or an activated alkyne. In some such embodiments, the modified biomolecule may be conjugated to a compound of any one of Formulas (I) to (XIII) comprising a terminal alkyne and/or a compound of any one of Formulas (I) to (XIII) comprising an azide, using click chemistry. In some embodiments, the modified biomolecule may be conjugated to a compound of any one of Formulas (I) to (XIII) comprising an azide using click chemistry, and may be conjugated to another compound that comprises a phosphine using a Staudinger ligation or comprises an alkyne, such as a terminal alkyne or activated alkyne, using a 1,3-bipolar cycloaddition. Alternatively, in some embodiments, the modified biomolecule may be conjugated to a compound of any one of Formulas (I) to (XIII) comprising a terminal alkyne, and may be conjugated to another compound that comprises an azide, both using click chemistry. Numerous combinations of chemical handles and conjugating reagents are possible, and can be selected according to the intended application by one skilled in the art.

In some embodiments, a method comprises two or more conjugation reactions. In some such embodiments, two or more conjugation reactions occur using the same reaction chemistry (i.e., two or more occur using click chemistry, 1,3-dipolar cycloaddition, or Staudinger ligation). As a nonlimiting example, a first modified biomolecule comprises an azide and a second modified biomolecule comprises an alkyne. Both modified biomolecules may be conjugated using click chemistry, either simultaneously or sequentially. In some such embodiments, the modified biomolecules are contacted with a first compound of any one of Formulas (I) to (XIII) comprising an alkyne and a second compound of any one of Formulas (I) to (XIII) comprising an azide. The first biomolecule comprising the azide will be conjugated to the first compound of any one of Formulas (I) to (XIII) comprising an alkyne, and the second biomolecule comprising the alkyne will be conjugated to the second compound of any one of Formulas (I) to (XIII) comprising an azide. In some embodiments, in order to reduce the occurrence of the first biomolecule conjugating to the second biomolecule, the concentration of the compounds of Formulas (I) to (XIII) can be controlled appropriately (e.g., such that they are in excess with respect to the concentration of the biomolecules) and/or the biomolecules can be spatially distinct (e.g., in different cellular compartments).

In some embodiments, two or more conjugation reactions occur using different reaction chemistry. As a nonlimiting example, a first modified biomolecule comprises an azide and a second modified biomolecule comprises a phosphine. The first biomolecule may be conjugated to a first compound of any one of Formulas (I) to (XIII) comprising an alkyne using click chemistry, and the second biomolecule may be conjugated to a second compound of any one of Formulas (I) to (XIII) comprising an azide using Staudinger ligation. The click reaction and the Staudinger ligation may be carried out either simultaneously or sequentially. In some embodiments, in order to reduce the occurrence of the first biomolecule conjugating to the second biomolecule, the concentration of the compounds of Formulas (I) to (XIII) can be controlled appropriately (e.g., such that they are in excess with respect to the concentration of the biomolecules) and/or the biomolecules can be spatially distinct (e.g., in different cellular compartments).

Conjugation in a Cell

In some embodiments, methods of conjugating a modified biomolecule to a compound of any one of Formulas (I) to (XIII) in a cell are provided. In some such embodiments, the conjugated biomolecule is separated from the cell following conjugation. In some embodiments, the conjugated biomolecule is identified, detected, and/or quantified in the cellular environment following conjugation (such as, for example, in the live cell, or in a cell that has been fixed and/or permeabilized prior to identification, detection and/or quantification of the biomolecule).

In some embodiments, a method of conjugating a modified biomolecule to a compound of any one of Formulas (I) to (XIII) in a cell comprises contacting a cell comprising a modified biomolecule with a compound of any one of Formulas (I) to (XIII) under conditions allowing the compound of any one of Formulas (I) to (XIII) to come into contact with the modified biomolecule. In some embodiments, if the modified biomolecule is located on the surface of the cell, contacting the cell with a composition comprising the compound of any one of Formulas (I) to (XIII) allows conjugation of the modified biomolecule. In some embodiments, when the modified biomolecule is located inside the cell, the cell may be contacted with a composition comprising the compound of any one of Formulas (I) to (XIII) with or without prior fixing and/or permeabilization of the cell. In some embodiments, for example when the conjugation occurs via click reaction, the cell may also be contacted with a copper ion source, a reducing agent, and/or a copper ion chelator. Additional components, such as buffers, detergents, salts, and the like, can also be included in the conjugation reaction. One skilled in the art can select suitable additional components depending on the application.

The conjugation can be performed under aerobic or anaerobic conditions, such as under nitrogen or argon gas, and can be performed for any suitable length of time, such as, for example, from five minutes to six hours, from 10 minutes to 3 hours, from 20 minutes to 3 hours, or from 30 minutes to 2 hours. The reaction can be performed at a wide range of temperatures, for example, between 4° C. and 50° C., between 10° C. and 40° C., or between 15° C. and 30° C.

Cells may be fixed using any method, including, but not limited to treatment with 4% formaldehyde or methanol.

Cells may be permeabilized by any method, including but not limited to treatment with NP-40 buffer or 0.1% Triton buffer.

In some embodiments, a cell comprising more than one modified biomolecule is contacted with more than one compound of any one of Formulas (I) to (XIII), wherein the compounds of Formulas (I) to (XIII) are detectably different. In some such embodiments, the cell is contacted with two or more compounds of Formulas (I) to (XIII) simultaneously or sequentially. Nonlimiting exemplary chemical handles that may be used in such multiplex reactions are described above.

Following conjugation, the conjugated biomolecules may be separated and/or detected according to methods known in the art. Exemplary such methods are discussed herein.

In some embodiments, a method of comprises:
(a) contacting a cell comprising a modified biomolecule with a compound of any one of Formulas (I) to (XIII) under conditions allowing conjugation of the modified biomolecule to the compound of formula compound of any one of Formulas (I) to (XIII) to form a conjugated biomolecule; and
(b) detecting the conjugated biomolecule.
In some embodiments, the modified biomolecule comprises an azide and the compound of any one of Formulas (I) to (XIII) comprises a terminal alkyne. In some embodiments, the modified biomolecule comprises a terminal alkyne, an activated alkyne, or a phosphine, and the compound of any one of Formulas (I) to (XIII) comprises an azide. In some embodiments, the method comprises separating the conjugated biomolecule, before or after (b). In some embodiments, the method comprises fixing the cell before (a). In some embodiments, the compound of any one of Formulas (I) to (XIII) comprises a reporter molecule. In some embodiments, the compound of any one of Formulas (I) to (XIII) comprises a fluorophore. In some embodiments, detecting comprises illuminating the conjugated biomolecule with an appropriate wavelength of light, such that the reporter molecule emits light, and observing the emitted light.

Conjugation in Solution

In some embodiments, methods of conjugating a modified biomolecule to a compound of any one of Formulas (I) to (XIII) in solution are provided. Such solutions include, but are not limited to, cell lysates, solutions of isolated biomolecules (in which the biomolecules are separated from at least some of the components of cells in which the biomolecules are ordinarily found), cell supernatants, liquid biological samples (described below), and the like.

In some embodiments, a method of conjugating a modified biomolecule to a compound of any one of Formulas (I) to (XIII) in solution comprises contacting the modified biomolecule with a compound of any one of Formulas (I) to (XIII) under conditions allowing the compound of any one of Formulas (I) to (XIII) to react with the modified biomolecule via a click reaction, a 1,3-dipolar cycloaddition, or a Staudinger ligation. In some embodiments, for example when the conjugation occurs via click reaction, a copper ion source, a reducing agent, and/or a copper ion chelator may also be included in the solution. Additional components, such as buffers, detergents, salts, and the like, can also be included in the conjugation reaction. One skilled in the art can select suitable additional components depending on the application.

In some embodiments, more than one modified biomolecule is present in solution. In some such embodiments, more than one compound of any one of Formulas (I) to (XIII) is also added to the solution and conjugated to the more that one modified biomolecules. In some embodiments, two or more compounds of Formulas (I) to (XIII) are added to the solution sequentially or simultaneously. In some embodiments, the compounds of Formulas (I) to (XIII) are detectably different. Nonlimiting exemplary chemical handles that may be used in such multiplex reactions are described above.

The conjugation can be performed under aerobic or anaerobic conditions, such as under nitrogen or argon gas, and can be performed for any suitable length of time, such as, for example, from five minutes to six hours, from 10 minutes to 3 hours, from 20 minutes to 3 hours, or from 30 minutes to 2 hours. The reaction can be performed at a wide range of temperatures, for example, between 4° C. and 50° C., between 10° C. and 40° C., or between 15° C. and 30° C.

Following conjugation, the conjugated biomolecules may be separated and/or detected according to methods known in the art. Exemplary such methods are discussed herein.

In some embodiments, a method of comprises:
(c) contacting a modified biomolecule with a compound of any one of Formulas (I) to (XIII) under conditions allowing conjugation of the modified biomolecule to the compound of formula compound of any one of Formulas (I) to (XIII) to form a conjugated biomolecule; and
(d) detecting the conjugated biomolecule.
In some embodiments, the modified biomolecule comprises an azide and the compound of any one of Formulas (I) to (XIII) comprises a terminal alkyne. In some embodiments, the modified biomolecule comprises a terminal alkyne, an activated alkyne, or a phosphine, and the compound of any one of Formulas (I) to (XIII) comprises an azide. In some embodiments, the method comprises separating the conjugated biomolecule. In some embodiments, the compound of any one of Formulas (I) to (XIII) comprises a reporter molecule. In some embodiments, the compound of any one of Formulas (I) to (XIII) comprises a fluorophore. In some embodiments, detecting comprises illuminating the conjugated biomolecule with an appropriate wavelength of light, such that the reporter molecule emits light, and observing the emitted light.

Conjugation on a Solid Support

In some embodiments, methods of conjugating a modified biomolecule to a compound of any one of Formulas (I) to (XIII) on a solid support are provided. Nonlimiting exemplary such solid supports include the various solid supports discussed herein, including, but not limited to, solid and semi-solid matrixes, such as glass, slides, arrays, silica particles, polymeric particles, microtiter plates and polymeric gels. In some embodiments, the compound of any one of Formulas (I) to (XIII) comprises a solid support as a substituent. In some embodiments, the modified biomolecule is bound to a solid support.

The modified biomolecule may be bound to a solid support through any means. For example, in some embodiments, the modified biomolecule may have been adsorbed onto a solid support through non-covalent interactions. In some embodiments, the modified biomolecule comprises a member of a binding pair, and is bound to a solid support that comprises the other member of the binding pair. In some embodiments, the modified biomolecule has been conjugated to a solid support through a prior reaction, which may be a click reaction, 1,3-dipolar cycloaddition, a Staudinger ligation, or other type of reaction. Thus, in some embodiments, the modified biomolecule is attached to a solid support using a functional group other than the chemical handle used for a click reaction, 1,3-dipolar cycloaddition, or Staudinger ligation, whereupon the attached modified biomolecule is then conjugated to a compound of any one of Formulas (I) to (XIII) through the chemical handle in a click reaction, 1,3-dipolar cycloaddition, or Staudinger ligation. By way of example only, the modified biomolecule can be immobilized to a solid support using hydroxyl, carboxyl, amino, thiol, aldehyde, halogen, nitro, cyano, amido, urea, carbonate, carbamate, isocyanate, sulfone, sulfonate, sulfonamide or sulfoxide functional groups.

When conjugation of the biomolecule to a compound of any one of Formulas (I) to (XIII) occurs on a solid support, in some embodiments, the reaction is carried out in a similar composition as is used for solution-phase conjugation.

In some embodiments, a method of comprises:
(e) contacting a modified biomolecule with a compound of any one of Formulas (I) to (XIII) under conditions allowing conjugation of the modified biomolecule to the compound of formula compound of any one of Formulas (I) to (XIII) to form a conjugated biomolecule, wherein the modified biomolecule or the compound of any one of Formulas (I) to (XIII) is immobilized on a solid support; and
(f) detecting the conjugated biomolecule.
In some embodiments, the modified biomolecule comprises an azide and the compound of any one of Formulas (I) to (XIII) comprises a terminal alkyne. In some embodiments, the modified biomolecule comprises a terminal alkyne, an activated alkyne, or a phosphine, and the compound of any one of Formulas (I) to (XIII) comprises an azide. In some embodiments, the method comprises separating the conjugated biomolecule. In some embodiments, the compound of any one of Formulas (I) to (XIII) comprises a reporter molecule. In some embodiments, the compound of any one of Formulas (I) to (XIII) comprises a fluorophore. In some embodiments, detecting comprises illuminating the conjugated biomolecule with an appropriate wavelength of light, such that the reporter molecule emits light, and observing the emitted light.

Separation of Conjugated Biomolecules

In some embodiments, a conjugated biomolecule is separated following conjugation via a click reaction, a 1,3-dipolar cycloaddition, or a Staudinger ligation. Nonlimiting exemplary methods of separating conjugated biomolecules include sedimentation, centrifugation, magnetic attraction, chromatographic methods, and electrophoretic methods.

In some embodiments, separation of the conjugated biomolecule is facilitated by a substituent on a compound of any one of Formulas (I) to (XIII) that has been conjugated to the biomolecule. As a nonlimiting example, the compound of any one of Formulas (I) to (XIII) may comprise a member of a binding pair, which is then bound to the complementary member of the binding pair to separate the conjugated biomolecule. For example, in some embodiments, the compound of any one of Formulas (I) to (XIII) comprises biotin such that the conjugated biomolecule may be separated by binding to a streptavidin-containing solid support, such as streptavidin-coated multiwell plates or streptavidin-coated microparticles. As a further non-limiting example, the compound of any one of Formulas (I) to (XIII) may comprise a microparticle (including, for example, a magnetic microparticle) as a substituent, such that the conjugated biomolecule may be separated by centrifugation (or contact with a magnet if the microparticle is magnetic).

In some embodiments, conjugated biomolecules are separated by thin layer or column chromatography. Nonlimiting exemplary such chromatography includes size exclusion, ion exchange, and affinity chromatography. In some embodiments, conjugated biomolecules are separated using isoelectric focusing. In some embodiments, conjugated biomolecules are separated using electrophoresis. Nonlimiting exemplary electrophoresis includes gel electrophoresis (such as, for example, agarose gel electrophoresis and acrylamide gel electrophoresis), capillary electrophoresis, capillary gel electrophoresis, and slab gel electrophoresis. Gel electrophoresis can be denaturing or nondenaturing, and can include denaturing gel electrophoresis followed by nondenaturing gel electrophoresis (e.g., "2D" gels). The conjugated biomolecules may be detected at any time before, during, or after separation. In some embodiments, such as when the conjugated biomolecules are separated by gel electrophoresis, the conjugated biomolecules may be detected in the separation medium (e.g., the gel), either during or after separation.

One skilled in the art can select a suitable separation method according to the moieties conjugated to the conjugated biomolecule, the identity or type of biomolecule, and the particular application.

Detection of Conjugated Biomolecules

In some embodiments, the conjugated biomolecules are detected following conjugation. In some embodiments, a reporter molecule that is a substituent of a compound of any one of Formulas (I) to (XIII) that has been conjugated to a biomolecule is used for detection. In some embodiments, a carrier molecule that is a substituent of a compound of any one of Formulas (I) to (XIII) that has been conjugated to a biomolecule is used for detection. In some embodiments, a solid support that is a substituent of a compound of any one of Formulas (I) to (XIII) that has been conjugated to a biomolecule is used for detection. The phrase "used for detection" encompasses direct or indirect detection of the reporter molecule, carrier molecule, or solid support. The conjugated biomolecules may be detected by any method. Many methods of detection are known in the art, and some non-limiting exemplary methods will be discussed below by way of illustration only. One skilled in the art can select a suitable detection method depending on the identity and/or properties of the reporter molecule, carrier molecule, solid support, biomolecule, and any other moieties associated therewith.

Detection of conjugated biomolecules may occur at any time following conjugation, and at any time before, during, or after separation, if such separation is carried out.

In some embodiments, the moieties used for detection are any fluorophores described herein that can be used as substituents on compounds of Formulas (I) to (XIII). Nonlimiting exemplary such fluorophores include fluoresceins, rhodamines, TAMRA, Alexa dyes, SYPRO dyes, and BODIPY dyes.

In some embodiments, a method comprises multiplexed detection of modified biomolecules, for example, by conjugating the modified biomolecules to compounds of Formulas (I) to (XIII) comprising different reporter molecules. In some embodiments, the conjugation reaction can be carried out such that modified biomolecule comprising particular chemical handles are conjugated to compounds of Formulas (I) to (XIII) comprising particular reporter molecules.

By way of illustration only, as a nonlimiting example, a composition comprising a first modified biomolecule, a second modified biomolecule, and a third modified biomolecule is provided, wherein the first modified biomolecule comprises a phosphine, the second modified biomolecule comprises an azide, and the third modified biomolecule comprises a terminal alkyne. The composition is contacted with a first compound of any one of Formulas (I) to (XIII) comprising a first reporter molecule and an azide moiety in the absence of Cu(I) ions. The first compound conjugates to the first biomolecule through a Staudinger ligation. In some embodiments, unconjugated first compound is rendered inactive and/or removed from the composition. Thereafter, a second compound of any one of Formulas (I) to (XIII) comprising a second reporter molecule and a terminal alkyne, and a third compound of any one of Formulas (I) to (XIII) comprising a third reporter molecule and an azide are added to the composition in the presence of Cu(I) ions. The second compound conjugates to the second modified biomolecule and the third compound conjugates to the third modified biomolecule through a click reaction. Following conjugation, each of the three conjugated biomolecules comprises a different reporter molecule and, in some embodiments, can be detected in a multiplex detection method.

In some embodiments, in-gel fluorescence detection allows for quantitative differential analysis of biomolecules and is amenable to multiplexing with other protein gel stains. In some embodiments, utilizing fluorescent- and/or UV-excitable reporter molecules as substituents of compounds of Formulas (I) to (XIII) allows for the multiplexed detection of biomolecules (such as, for example, glycoproteins, phosphoproteins, and total proteins) in the same 1-D or 2-D gels.

In some embodiments, detection of modified biomolecules (such as, for example, proteins) can be by Western blot, in which the modified biomolecules are separated by gel electrophoresis and transferred to a blotting membrane. The modified biomolecules may be conjugated on the blotting membrane to a compound of any one of Formulas (I) to (XIII), and then detected. Alternatively, in some embodiments, modified biomolecules that have been previously conjugated to a compound of any one of Formulas (I) to (XIII) can be separated by gel electrophoresis and transferred to a blotting membrane, and then detected.

Another potential aspect of "in gel" detection is the total detection of proteins in electrophoresis gels or Western blot membranes using a "universal" click chemistry, in which phenylboronic acid-containing molecules are tethered via a linker to an azide moiety or an alkyne moiety. The phenylboronic acid stably associates with the cis-diol moieties on glycoproteins under certain conditions. Such phenylboronic acid-containing molecules can be used, in some embodiments, to modify glycoproteins with either azide or alkyne moieties after electrophoretic separation. The azide or alkyne moieties can then be used to conjugate the glycoproteins to a compound of any one of Formulas (I) to (XIII) comprising, for example, a reporter molecule, via click chemistry, activated alkyne chemistry, or Staudinger ligation. In some embodiments, the conjugated glycoproteins may then be detected, either directly or indirectly, using, for example, the reporter molecule. In some embodiments, glycoproteins of interest can then be isolated by excising portions of the gel comprising the modified glycoproteins, and the phenylboronic acid dissociated from the glycoproteins under acidic conditions, thereby releasing the conjugated compound of any one of Formulas (I) to (XIII) from the glycoprotein. In some embodiments, the glycoprotein may then be identified using, for example, mass spectrometry.

In some embodiments, when detection comprises detecting an optical response, the conjugated biomolecules may be detected at any time by illumination with a wavelength of light that results in a detectable optical response, and observation with a means for detecting the optical response. In some embodiments, such illumination is by a violet or visible wavelength emission lamp, an arc lamp, a laser, or even sunlight or ordinary room light, wherein the wavelength of such sources overlap the absorption spectrum of the moiety being detected, such as a fluorophore or chromophore. In some embodiments, such illumination is by a violet or visible wavelength emission lamp, an arc lamp, a laser, or even sunlight or ordinary room light, wherein a fluorescent compound displays intense visible absorption as well as fluorescence emission.

In some embodiments, the illumination sources include, but are not limited to, hand-held ultraviolet lamps, mercury arc lamps, xenon lamps, argon lasers, laser diodes, blue laser diodes, and YAG lasers. These illumination sources are optionally integrated into laser scanners, flow cytometer, fluorescence microplate readers, standard or mini fluorometers, or chromatographic detectors. The fluorescence emission following illumination is optionally detected by visual inspection, or by use of any of the following devices: CCD cameras, video cameras, photographic film, laser scanning devices, fluorometers, photodiodes, photodiode arrays, quantum counters, epifluorescence microscopes, scanning microscopes, flow cytometers, fluorescence microplate readers, or by means for amplifying the signal such as photomultiplier tubes.

In some embodiments, for example, when a sample is examined using a flow cytometer, a fluorescence microscope, or a fluorometer, the instrument is optionally used to distinguish and/or discriminate between multiple fluorophores having detectably different optical properties. In some embodiments, when a sample is examined using a flow cytometer, examination of the sample optionally includes isolation of particles within the sample based on the fluorescence response by using a sorting device.

In certain embodiments, fluorescence is optionally quenched using either physical or chemical quenching agents.

Samples

The end user will determine the choice of the sample and the way in which the sample is prepared. Samples that can be used with the methods and compositions described herein include, but are not limited to, any biological derived material or aqueous solution that contains a modified biomolecule. In certain embodiments, a samples also includes material in which a modified biomolecule has been added. The sample that can be used with the methods and compositions described herein can be a biological fluid including, but not limited to, whole blood, plasma, serum, nasal secretions, sputum, saliva, urine, sweat, transdermal exudates, cerebrospinal fluid, or the like. In other embodiments, the sample are biological fluids that include tissue and cell culture medium wherein modified biomolecule of interest has been secreted into the medium. Cells used in such cultures include, but are not limited to, prokaryotic cells and eukaryotic cells that include primary cultures and immortalized cell lines. Such eukaryotic cells include, without limitation, ovary cells, epithelial cells, circulating immune cells, β cells, hepatocytes, and neurons. In certain embodiments, the sample may be whole organs, tissue or cells from an animal, including but not limited to, muscle, eye, skin, gonads, lymph nodes, heart, brain, lung, liver, kidney, spleen, thymus, pancreas, solid tumors, macrophages, mammary glands, mesothelium, and the like.

Kits

In some embodiments, kits are provided, wherein the kits comprise a compound of any one of Formulas (I) to (XIII). In some embodiments, a kit further comprises a copper ion source. In some embodiments, a kit further comprises a reducing agent. In some embodiments, a kit further comprises a copper ion chelator. In some embodiments, a kit further comprises a reagent for modifying a biomolecule. Nonlimiting exemplary such copper ion sources, reducing agents, copper ion chelators, and reagents for modifying biomolecules are described herein.

In some embodiments, a kit further comprises a copper ion chelator of formula (V).

A detailed description of the invention having been provided above, the following examples are given for the purpose of illustrating the invention and shall not be construed as being a limitation on the scope of the invention or claims.

The following examples are intended to illustrate but not limit the invention.

Example 1

FIG. 1A shows an exemplary method of preparing a reagent for making a compound of any one of Formulas (I) to (XIII). The exemplary method is as follows.

General Synthetic Methods

Chemicals were purchased from Sigma-Aldrich, Alfa Aesar, TCI America, Fisher Scientific, Adesis Inc, or EMD unless specified otherwise. Analytical thin-layer chromatography was performed using 0.25 mm silica gel $60_{F254}$ plates and visualized with 254 nm UV light or with bromocresol green. $^1$H NMR spectra were recorded on a Bruker Avance 400 MHz or a Varian Inova 500 MHz spectrometer. All samples were dissolved in $CDCl_3$, $CD_3OD$, $D_2O$, or $d_6$-DMSO and chemical shifts (δ) are expressed in parts per million relative to residual solvent peak as an internal standard. Abbreviations are: s, singlet; d, doublet; t, triplet; q, quartet; m, multiplet; br, broad. Coupling constants (J) are reported in hertz (Hz). Mass spectra were recorded using electrospray ionization (ESI) on an Applied Biosystems 200 QTRAP mass spectrometer or an Agilent 1100 MSD ion trap mass spectrometer. Absorbance and fluorescence properties for selected compounds were determined on a Perkin Elmer LS50B Luminescence Spectrometer in HPLC-grade methanol.

Analytic LC-MS data were acquired using Waters 2695 Alliance HPLC coupled to a single-quadrupole Waters Micromass ZQ mass spectrometer, and an Xterra MS C18 column (2.5 μm particle size, 4.6×50 mm dimension). The elution gradient is 5-95% acetonitrile/10 mM $NH_4OAc$, pH=7 over 20 minutes. MS data were recorded simultaneously in negative and positive ionization modes. Preparative HPLC purification was performed using Waters 600 HPLC equipped with Waters 996 diode array detector, Waters 717 plus autosampler, and a Luna C18 column (Phenomenex; 5 μm particle size, 4.6 mm×250 mm dimension).

Preparation of picolyl 6-(methoxycarbonyl)nicotinic acid (2)

12.6 g of pyridine-2,5-dicarboxylic acid was suspended in 150 mL of methanol and 4.5 g of 95% sulfuric acid was slowly added. The reaction was heated to reflux for 2.5 h, cooled to 25° C. and the whole was poured into 750 mL of deionized (DI) water at room temperature. A white precipitate formed and the suspension was stirred for 20 minutes, filtered through a Buchner funnel with filter paper. The precipitate was rinsed with deionized and collected. This material was dissolved in 150 mL of dichloromethane heated to 35° C., washed once with 150 mL of saturated sodium bicarbonate solution. The two layers were separated, and 2 N HCl was added to the organic layer to until the pH was 1-2. A white precipitate formed and was filtered with a Buchner funnel fitted with filter paper. The product was rinsed with deionized water, collected, and dried under vacuum to provide 4.75 g of compound 2. TLC (80:20 ACN:$H_2O$, uv): $R_f$=0.53 (bis-methyl ester $R_f$=0.83). $^1$H NMR (400 MHz, $d_6$-DMSO): 9.12 (br s, 1H), 8.42 (t, 1H), 8.15 (t, 1H), 3.89 (s, 3H).

Preparation of 5-(2,5-dioxopyrrolidin-1-yl) 2-methyl pyridine-2,5-dicarboxylate (3)

100 mg of 2 was dissolved in 10 mL of dichloromethane at ambient temperature. N-hydoxysuccinimide (95 mg) was added, followed by 133 mg of 1-ethyl-3-(3-dimethylaminopropyl) carbodiimide) hydrochloride and the mixture stirred at room temperature for 2 hours. The mixture was then diluted with 15 mL of chloroform, followed by the addition of 15 mL of 2% HCl solution. The organic layer was successively washed once with 15 mL of DI water. The organic layer was then dried with $MgSO_4$, filtered and 3 used directly in the next step. TLC (ethyl acetate, uv): $R_f$=0.53.

Preparation of methyl 5-((2-((tert-butoxycarbonyl) amino)ethyl) carbamoyl) picolinate (4)

Compound 3 is used directly by dissolving in 15 mL of dichloromethane. 0.30 mL of N,N,-diisopropylethylamine was added at room temperature followed by 119 mg of tert-butyl (2-aminoethyl)carbamate hydrochloride was then added and the reaction was stirred for 50 minutes, at which time 30 mL of dichloromethane was added followed by 20 mL of 2 M $Na_2CO_3$. The layers were separated and the organic layer was dried with $MgSO_4$, filtered and concentrated to a residue which was taken up in 3 mL of warm methanol and loaded onto a silica gel chromatography column and eluted with ethyl acetate and methanol to provide 104 mg of 4 as a white solid. TLC (ethyl acetate, uv): $R_f$=0.32.). $^1$H NMR (400 MHz, $CDCl_3$): 9.15 (d, 1H), 8.30 (d, 1H), 8.14 (complex, 2H), 5.32 (br s, 1H), 4.00 (s, 3H), 3.56 (m, 2H), 3.41 (m, 2H), 1.39 (s, 9H).

Preparation of tert-butyl (2-(6-(hydroxymethyl)nicotinamido)ethyl) carbamate (5)

Compound 4 (2.4 g) was dissolved in 50 mL of methanol and 567 mg of $NaBH_4$ was carefully added to control gas evolution. THF (5 mL) was added the reaction was placed in a preheated bath at 65° C. The reaction was stirred at this temperature for 35 minutes, at which time 6 mL of 2 M Na$_2$CO$_3$ was added dropwise followed by 6 mL of water. The mixture was then concentrated to ⅕ original volume and 100 mL of ethyl acetate was added. The layers were separated and the organic layer was dried with MgSO$_4$, filtered and concentrated to an oil, which was taken up in dichloromethane and flashed with dichloromethane with 0.5% triethylamine and methanol to provide 0.91 g of 5 as a white solid. TLC (ethyl acetate, uv): R$_f$=0.13.). $^1$H NMR (400 MHz, d$_6$-DMSO): 8.89 (s, 1H), 8.61 (s, 1H), 8.17 (d, 1H), 7.54 (d, 1H), 6.93 (m, 1H), 5.53 (s, 1H), 4.61 (s, 2H), 3.29 (m, 2H), 3.12 (m, 2H), 2.51 (s, 2H), 1.7 (s, 9H).

Preparation of tert-butyl (2-(6-(azidomethyl)nicotinamido)ethyl) carbamate (6)

Compound 5 (132 mg) was dissolved in 5 mL of DMF. Sodium azide (218 mg) was added, followed by triphenylphosphine (129 mg) and carbon tetrabromide (189 mg) and the reaction was stirred for 1 hour at which time 10 mL of 1 M Na$_2$CO$_3$ was added followed by 30 mL of ethyl acetate. The organic layer was washed twice with 15 mL of satt'd NaHCO$_3$ solution (each), the organic layer was dried with MgSO$_4$, filtered, and concentrated to a clear oil. This material was then purified by flash chromotagraphy suing ethyl acetate as eluent. TLC (ethyl acetate, uv): R$_f$=0.30. $^1$H NMR (400 MHz, CDCl$_3$): 9.04 (d, 1H), 8.19 (dd, 1H), 7.72 (br s, 1H), 7.43 (d, 1H), 5.17 (t, 1H), 4.55 (s, 2H), 3.58 (q, 2H), 3.43 (q, 2H), 1.43 (s, 9H).

FIG. 1B shows an exemplary method of preparing a compound of any one of Formulas (I) to (XIII) from tert-butyl (2-(6-(azidomethyl)nicotinamido)ethyl) carbamate (6). The exemplary method is as follows.

Preparation of a representative azido-dye conjugated compound, 6-(azidomethyl)-N-(2-(6,8-difluoro-7-hydroxy-2-oxo-2H-chromene-3-carboxamido)ethyl)nicotinamide (8)

Compound 6 (5.2 mg) was dissolved in 1 mL of DCM, cooled to 5° C., then 1 mL of TFA was added and the mixture was stirred for 15 minutes, then allowed to warm gradually to ambient temperature. The mixture was then concentrated to an orange oil and dried under vacuum for 2 hours at which time the mixture was taken up in 0.8 mL of DMF. 0.1 mL of N,N,-diisopropylethylamine was added, followed by 4.9 mg of Pacific Blue SE (7) at ambient temperature. The mixture was stirred for 1 hour, then the reaction mixture was loaded directly onto a silica gel column and chromatographed with dichloromethane and methanol to provide a pale yellow oil. This material was then purified by preparative HPLC using a gradient of 10 mM ammonium acetate and methanol to obtain the product of >99% purity by HPLC analysis. $^1$H NMR (400 MHz, d$_3$-MeOD): 9.21 (t, 1H), 8.98 (d, 1H), 8.68 (d, 1H), 8.26 (d, 1H), 7.57 (d, 1H), 7.26 (dd, 1H), 4.58 (s, 2H), 3.67-3.64 (m, 4H).

Preparation of QSYp Azide

QSY picolyl azide ("QSYp Azide") having the structure:

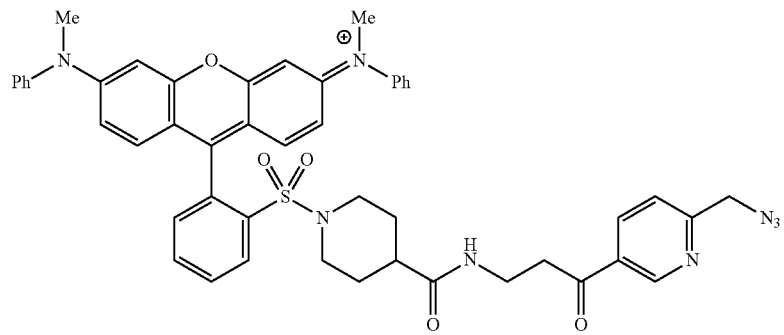

was prepared substantially as described above for compound (8), except QSY-SE (Life Technologies catalog # Q-10193):

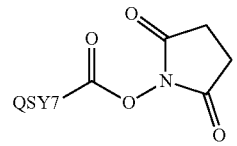

was used in place of Pacific Blue SE (7). Other labeled azide compounds, such as AF488-pAzide, AF647-pAzide, and biotin-PEG-pAzide, where PEG is one or more repeating units of polyethylene glycol. These compounds can be made using a substantially similar method as with compound 8. Selected examples of compounds synthesized in this manner include the following structures:

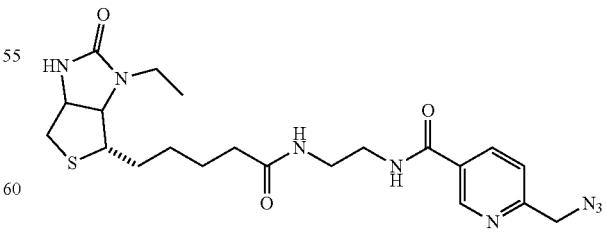

N-Ethyl biotin picolyl azide: MS (ESI): MH+=475.3, 473.3 (negative mode).

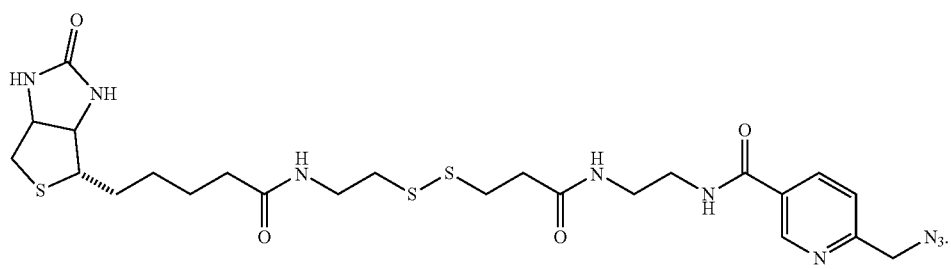
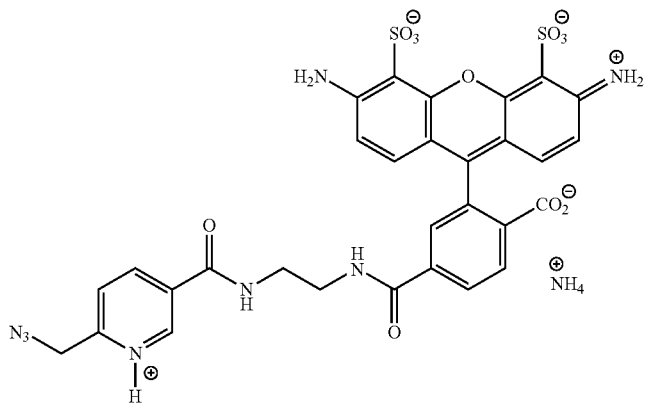
AF 488-picolyl azide: LCMS (ESI): Xterra C8, 50 mm×2.1 mm at 0.2 mL/min 40-100% ACN/10 mM NH₄OAc, pH=7 over 20 minutes. $T_r$=2.1 mM, MH+=737.05.
TAMRA picolyl azide:
AF 647-picolyl azide: LCMS (ESI): Xterra C8, 50 mm×2.1 mm at 0.2 mL/min. 40-100% ACN/10 mM NH₄OAc, pH=7 over 20 minutes. $T_r$=2.1 min, MH+=737.05.
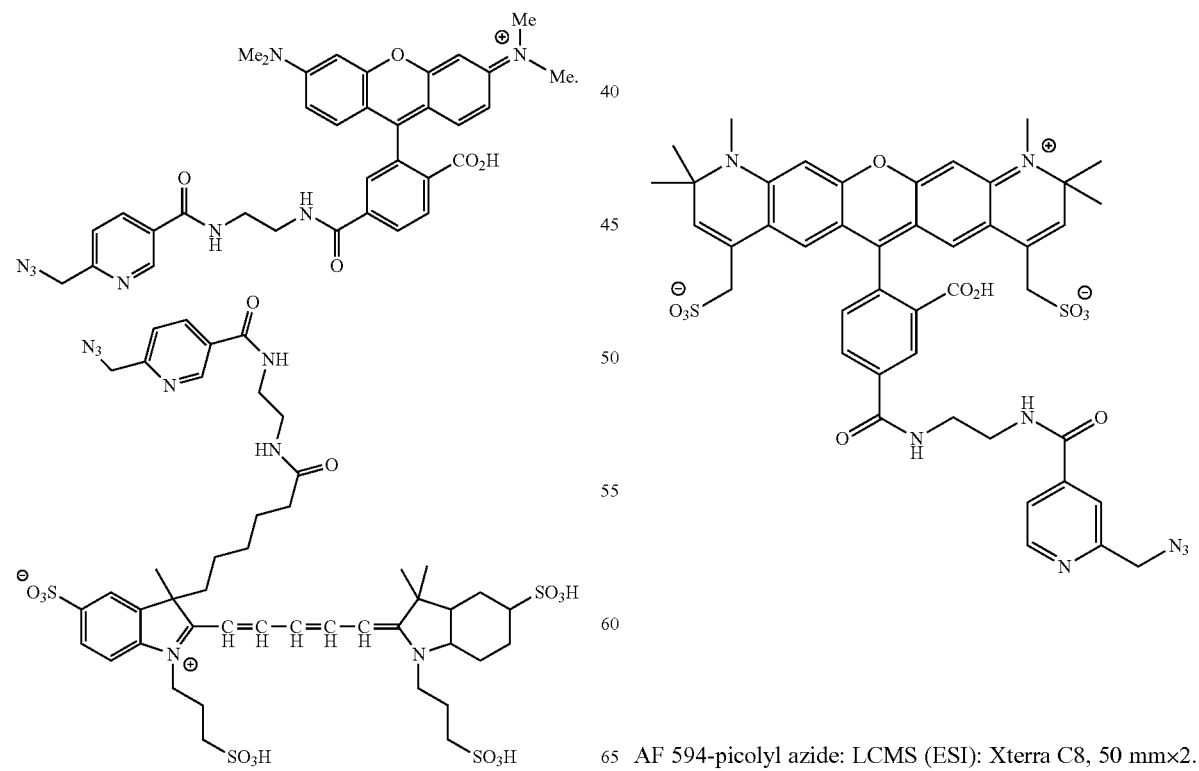
AF 594-picolyl azide: LCMS (ESI): Xterra C8, 50 mm×2.1 mm at 0.2 mL/min 0-60% ACN/10 mM NH₄OAc, pH=7 over 20 minutes. $T_r$=2.1 min, MH+=925.3.

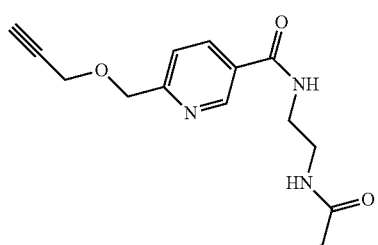

AF 555-picolyl alkyne (this compound was prepared in analogy to compound 15. AF 488-picolyl azide: LCMS (ESI): Xterra C8, 50 mm×2.1 mm at 0.2 mL/min 40-100% ACN/10 mM NH$_4$OAc, pH=7 over 20 minutes. T$_r$=6.17 min, MH+=1048.39.

FIG. 2 shows an exemplary method of preparing a compound of any one of Formulas (I) to (XIII). The exemplary method is as follows.

Preparation of 6-((prop-2-yn-1-yloxy)methyl)nicotinic acid (10)

Methyl 6-(hydroxymethyl)nicotinate (9, 303 mg) was dissolved in THF. 0.28 mL of a 9 M solution of propargyl bromide in toluene was added to the reaction vessel at ambient temperature. After 12 hours, the reaction mixture was diluted with 50 mL of Et$_2$O and washed once with 30 mL of a saturated solution of sodium bicarbonate. The organic layer was dried with MgSO$_4$, filtered, and concentrated to a residue, which was chromatographed on a silica gel column with ethyl acetate and hexanes to obtain an oil. TLC (ethyl acetate, uv): R$_f$=0.64. $^1$H NMR (400 MHz, CDCl$_3$): 9.16 (d, 1H), 8.32 (dd, 1H), 7.57 (d, 1H), 4.80 (s, 2H), 4.33 (dd, 2H), 3.96 (s, 3H), 2.50 (t, 1H).

Preparation of 6-((prop-2-yn-1-yloxy)methyl)nicotinic acid (11)

Compound 10 (18 mg) was dissolved in 0.5 mL of methanol. LiOH (0.131 mL of a 2 M aqueous solution) was added to the mixture at ambient temperature and the reaction was stirred for 30 minutes at which time the reaction mixture was directly applied to a silica gel column and chromatographed with dichloromethane (DCM) and methanol to provide 11 as a light yellow oil. TLC (ethyl acetate, uv): R$_f$=0.10. $^1$H NMR (400 MHz, CDCl$_3$): 9.21 (s, 1H), 8.36 (d, 2H), 7.48 (s, 1H), 4.80 (s, 2H), 4.31 (s, 2H), 2.49 (s, 1H).

Preparation of tert-butyl (2-(6-((prop-2-yn-1-yloxy)methyl)nicotinamido) ethyl)carbamate (12)

Compound 11 (11 mg) was dissolved in 2 mL of DCM. 0.12 mL of triethylamine was added at ambient temperature followed by 27 µL ethylchloroformate and the mixture was stirred for 2 hours, at which time the mixture was cooled to −15° C. and 57 mg of tert-butyl(2-aminoethyl)carbamate hydrochloride was added and the mixture was stirred for 12 hours. The mixture was then applied directly to silica gel column and chromatographed with hexanes and ethyl acetate to furnish 12 as a white powder. TLC (ethyl acetate, uv): R$_f$=0.43. $^1$H NMR (400 MHz, CDCl$_3$): 9.02 (s, 1H), 8.17 (dd, 1H), 7.60 (br s, 1H), 7.54 (d, 1H), 5.07 (br s, 1H), 4.79 (s, 2H), 4.32 (d, 2H), 3.58 (q, 2H), 3.44 (m, 2H), 2.50 (t, 1H), 2.06 (s, 1H), 1.44 (s, 9H).

Preparation of Compound 15

Compound 12 (3.5 mg) was dissolved in 0.3 mL of DCM and 0.5 mL of trifluoroacetic acid was added at 0-5° C. After 1.4 hours, the solvent was removed and the sample placed under vacuum for 3 hours. Compound 14 (4.9 mg) was then added, followed by 0.60 ml of DCM, and finally 0.10 mL of N,N,-diisopropylethylamine After 2 hours, the reaction mixture was concentrated directly under vacuum and 0.30 mL of methanol and 0.20 mL of a solution of 8% triethylamine in water was added. The reaction was stirred for 1 hour. 0.20 mL of a solution of 8% triethylamine in water was then added and the reaction was stirred for 30 minutes, then concentrated to a residue. This material was purified by HPLC using a gradient of 10 mM NH$_4$OAc/MeOH. The fractions containing product were collected and concentrated, taken up in water and lyophilized to provide 15 as a red powder. Analytical HPLC: Luna C18 250 mm×4.6 mm, 5 µm column at 1.0 mL/min with 10 mM NH$_4$OAc/Methanol gradient of 5-95% over 30 minutes. T$_R$=20.8 minutes, >99% pure at 254 nm and 490 nm. $^1$H NMR (400 MHz, D$_2$O): 8.46 (s, 1H), 7.83 (dd, 2H), 7.74 (dd, 1H), 7.26 (s, 1H), 7.08 (d, 1H), 6.60 (dd, 4H), 4.42 (s, 2H), 4.12 (d, 2H), 3.54 (m, 4H), 2.80 (m, 1H), [amide NH's exchanged with D$_2$O].

Example 2

In order to compare the click reaction rates using a picolyl azide reactant, to a similar reactant that lacks a pyridyl group, Cu(I)-catalzyed azide-alkyne cycloaddition reactions were carried out between Oregon Green® 488 ("OG") alkyne (Life Technologies, Carlsbad, Calif.) and either QSY® Azide having the structure:

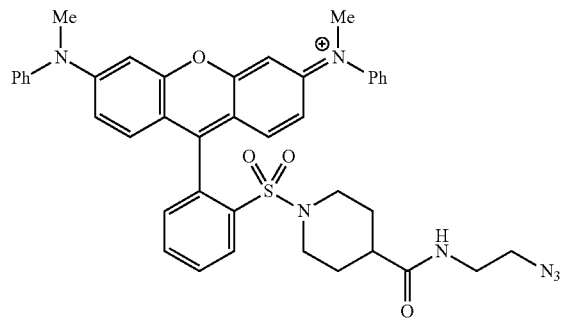 [SMILES: CN(c1ccccc1)c1ccc2c(-c3ccccc3S(=O)(=O)N3CCC(C(=O)NCCN=[N+]=[N-])CC3)c3cc/c(=[N+](/C)c4ccccc4)cc-3oc2c1]

or QSY® picolyl azide ("QSYp Azide;" see Example 1) having the structure:

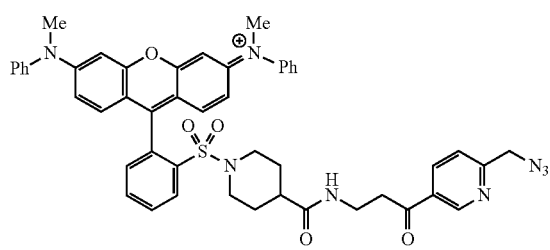 [SMILES: CN(c1ccccc1)c1ccc2c(-c3ccccc3S(=O)(=O)N3CCC(C(=O)NCCC(=O)c4ccc(CN=[N+]=[N-])nc4)CC3)c3cc/c(=[N+](/C)c4ccccc4)cc-3oc2c1]

Each reaction contained 10 µM OG alkyne, 40 µM of QSY Azide or QSYp Azide, 5 mM sodium ascorbate, and various concentrations of $CuSO_4$ were added in a buffer containing 100 mM Tris, pH 8, and 25% 1,2 propane diol. QSY acts as a quencher of OG. Thus, the click reaction brings the dyes in close proximity, resulting in quenching of the OG fluorescent signal.

Figure 3A:
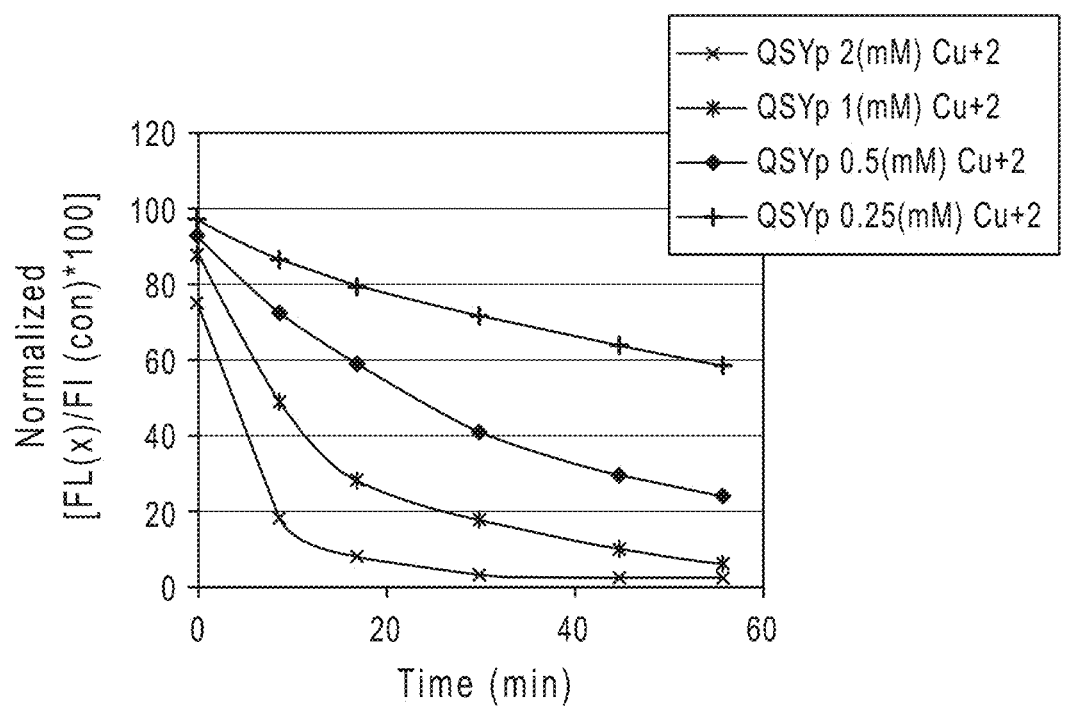
FIG. 3 shows rates of click reactions between reagents (A) QSY pAzide and Oregon Green® alkyne, and (B) QSY Azide and Oregon Green® alkyne, at various concentrations of Cu, as described in Example 2.
Figure 3B:
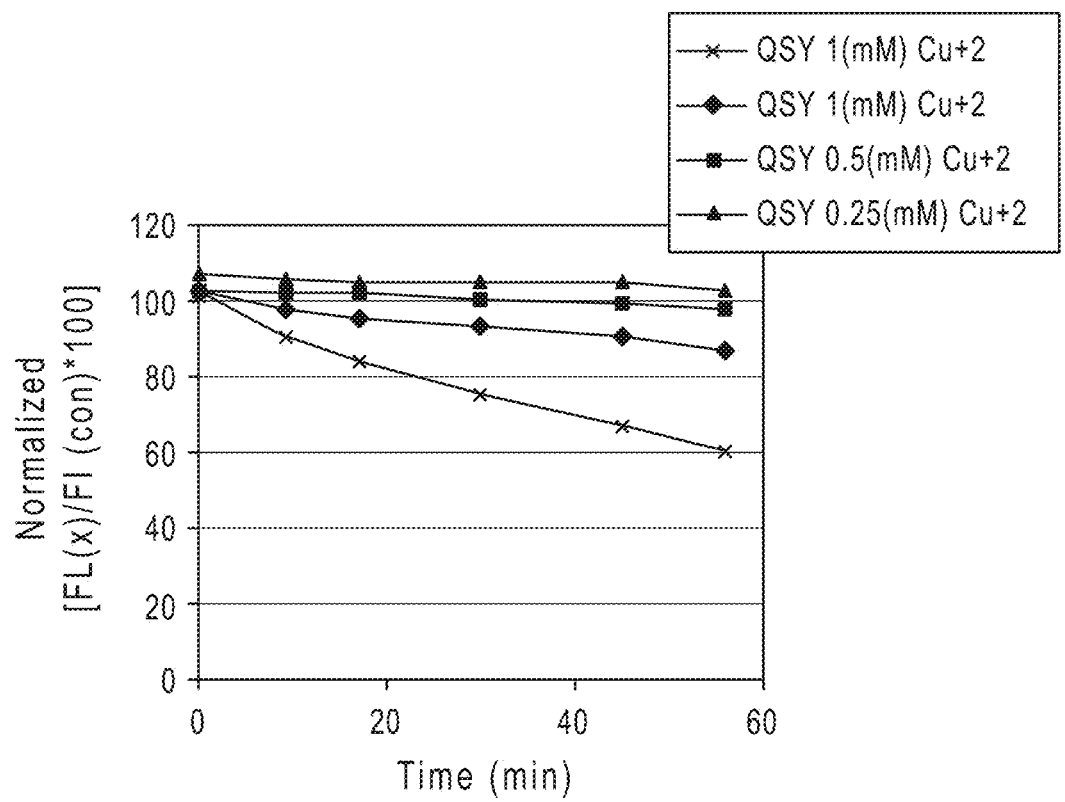

As shown in FIG. 3, click reaction rates using picolyl reagent QSY pAzide (A) were faster than click reaction rates using reagent QSY Azide (B) at all Cu concentrations tested. Thus, the presence of the picolyl moiety increased the rate of the click reaction in that experiment.

Next, the effect of a Cu(I)-stabilizing copper chelators on the click reactions between OG alkyne and QSY pAzide or QSY Azide was determined. In this experiment, reactions were carried out for 30 minutes in the presence of sodium ascorbate and 2 mM, 1 mM, 0.5 mM, or 0.25 mM $Cu^{2+}$; or in the presence of sodium ascorbate and 0.25 mM, 0.125 mM, 0.0625 mM, or 0.03125 mM $Cu^{2+}$ and THPTA having the structure:

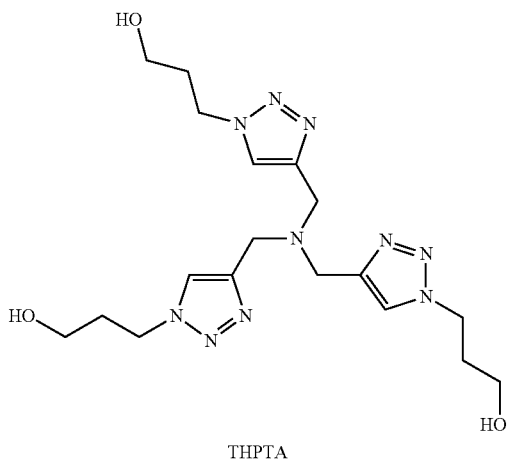 [SMILES: OCCCn1cc(CN(Cc2cn(CCCO)nn2)Cc2cn(CCCO)nn2)nn1 ; "THPTA"]

THPTA at a molar ratio of THPTA:Cu of 0:1 to 8:1.

Figure 4:
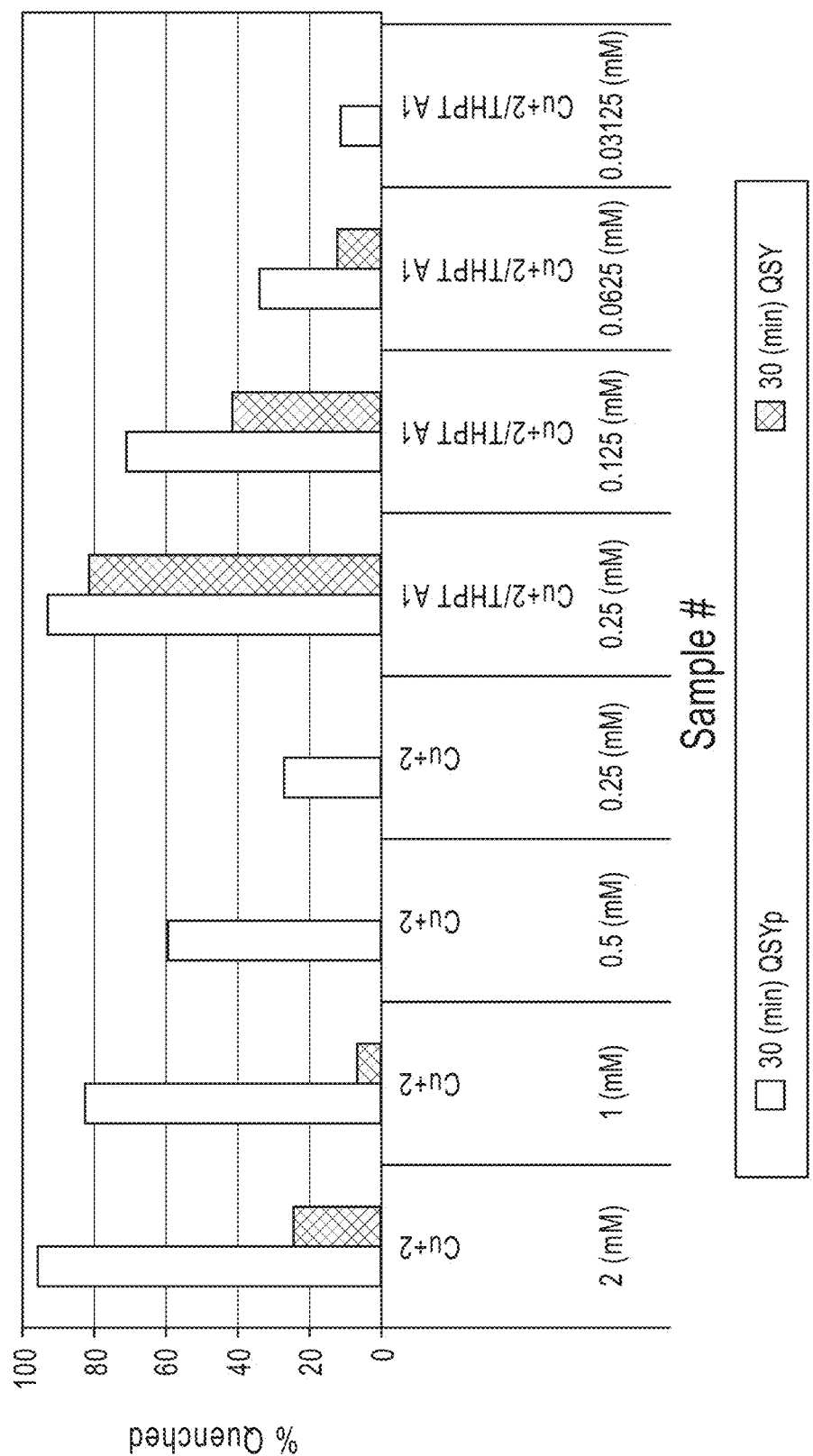
FIG. 4 shows the effect of increasing concentrations of $Cu^{2+}$, and increasing concentrations of $Cu^{2+}$ in the presence of copper chelator THPTA on the click reaction between Oregon Green® alkyne and QSY Azide or QSY pAzide, as described in Example 2.

The results are shown in FIG. 4. As shown in that figure, at higher concentrations of $Cu^{2+}$ and in the absence of THPTA, very little click reaction takes place between OG alkyne and QSY Azide in 30 minutes. In contrast, greater than 50% of the OG alkyne is quenched in 30 minutes when QSY pAzide is used as a reactant, in the presence of at least 0.5 mM $Cu^{2+}$. The presence of THPTA markedly increases the extent of the click reaction in 30 minutes for both QSY pAzide and QSY Azide (compare, for example, 0.25 mM $Cu^{2+}$ in the presence and absence of THPTA). Thus, THPTA not only reduces the requirement for $Cu^{2+}$ ions, which can be detrimental to biological systems, it greatly increases the reaction rate for both picolyl and non-picolyl click reactants.

Example 3

In order to determine whether picolyl azides showed similar enhancement in click reaction rates, various alkynes were used in the following click reaction:

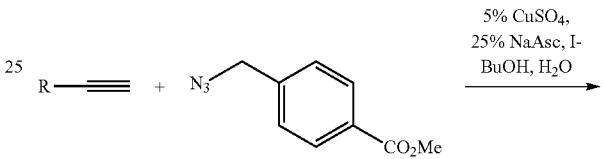

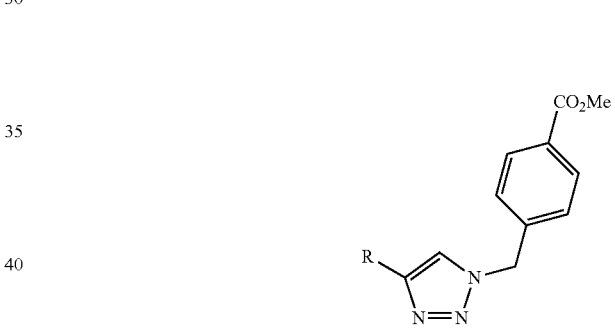

The time to completion of the reaction was determined by taking aliquots of the reaction mixture at time points and applying sample to thin-layer chromatggraphy (TLC) plates. The TLC plates were then developed using mixtures of organic solvents. Reaction progress was estimated by the intensity of spots corresponding to starting material and product. Reaction times are estimated.

The results of that experiment are shown below

| R | | | | |
|---|---|---|---|---|
| Time to completion | >2 h | 10-16 min | 10-16 min | No reaction |

In that experiment, use of the picolyl alkyne reactants resulted in much shorter reaction times than the non-picolyl alkynes under the same reaction conditions.

Example 4

A fluorogenic click assay for determining the relative rate of click reactions was used to test various azide compounds in a procedure adapted from Zhou and Fahrni, *J. Am. Chem. Soc.*, 2004, 126, 8862-8863:

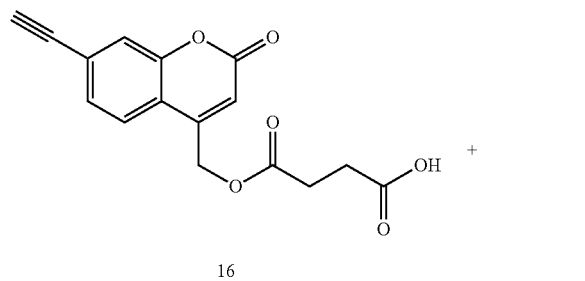

16

Ex = 325 nm
Em = 388 nm
QY = 0.014

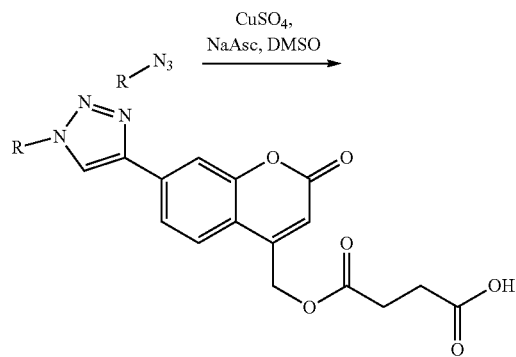

17

Ex = 328 nm
Em = 415 nm
QY = 0.25

General reactions conditions: 20 μM azide, 40 μM 7-ethynyl coumarin 16, and 4 mM sodium ascorbate in 100 μM Tris buffer at pH 7.4 with 25% v/v 1,2-propanediol at 25±1° C. Reactions were initiated by the addition of CuSO4: 125 μM. Coumarin fluorescence was recorded on a Molecular Devices SpectraMax M5 microplate reader with excitation at 320 nm and emission detection at 430 nm with a cutoff at 420 nm. The turn-on fluorescence of coumarin triazole was correlated to its concentration using a calibration curve made from known concentrations (1.25-40 μM) of the triazole adduct between 2-picolyl azide and 7-ethynylcoumarin 16. Fluorescence measurements were taken for at least 30 min at 30 sec intervals. Measurements for each azide were performed in triplicates or more. Error was determined from the standard deviation from data sets at each time point. Background fluorescence was subtracted from all data for normalization.

Coumarin-alkyne 16 was prepared and characterized as previously described in Zhou and Fahrni, *J. Am. Chem. Soc.*, 2004, 126, 8862-8863.

The various organic azide compounds used were synthesized as described below.

Benzyl azide (as shown below) is commercially available:

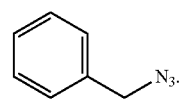

Synthesis of 2-azidomethylpyrdine (2-picolyl azide)

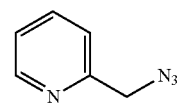

This compound was prepared and characterized according to a published literature procedure of Brotherton, W. S.; Michaels, H. A.; Simmons, J. T.; Clark, R. J.; Dalai, N. S.; Zhu, L. *Organic Letters* 2009, 11, 4954 4957.

Synthesis of 4-azidomethylbenzoic acid

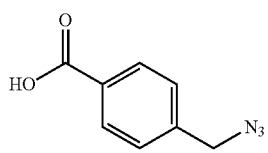 [SMILES: [N-]=[N+]=NCc1ccc(C(=O)O)cc1]

This compound was prepared and characterized as described in Zhou and Fahrni, *J. Am. Chem. Soc.*, 2004, 126, 8862-8863.

Synthesis of 4-azidomethylnicotinic acid

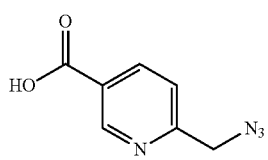

at a molar ratio of THPTA:Cu of 0:1 to 8:1. Methyl 5-(azidomethyl)nicotinate (114 mg, 0.59 mmol) was dissolved in methanol (2.5 mL). A 1.0 M solution of LiOH in water (1.78 mL, 1.78 mmol) was then added and the mixture was stirred for 25 minutes, at which time acetic acid (60 μL) was added and the mixture was loaded directly onto a silica gel column equilibrated with ethyl acetate+1% acetic acid and chromatographed with ethyl acetate+1% acetic acid to 4% acetonitrile/ethyl acetate+1% acetic acid to provide 101 mg (96%) of this compound as a yellow solid. Rf=0.35 (ethyl acetate+1% acetic acid, 254 nm UV). $^1$H NMR (400 MHz, 1:1 CDCl$_3$:CD$_3$OD): 9.75 (dd, J=2.0, 0.4 Hz, 1H), 8.98 (dd, J=8.0. 2.0 Hz, 1H), 8.12 (d, J=8.0 Hz, 1H), 5.35 (s, 1H), 5.18 (s, 2H). MS (ESI−): 177 (M$^+$, 100%; 133.0 (60%).

Synthesis of methyl-5-(azidomethyl)nicotinate

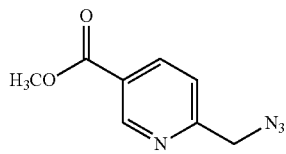 [SMILES: COC(=O)c1ccc(CN=[N+]=[N-])nc1]

This compound was prepared and characterized as described in Khilevich, A., Liu, B., Mayhugh, D. R., Schekeryantz, J. M., and Zhang, D. Imidazolecarboxamide derivatives as mGluR2 receptor potentiators and their preparation, pharmaceutical compositions and use in the treatment of depression. WO2010/009062. Jan. 21, 2010.

Synthesis of 2-azidomethyl-4-methoxypyridine

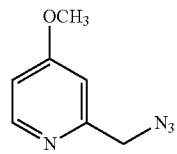 [SMILES: COc1ccnc(CN=[N+]=[N-])c1]

2-Hydroxymethyl-4-methoxypyridine (278 mg, 2.0 mmol) was dissolved in tetrahydrofuran (15 mL) in a 50 mL round-bottomed flask under argon. The flask was cooled to 0-5° C. with an ice/water bath for 10 minutes at which time, powdered KOH (157 mg, 2.8 mmol) was added followed by para-toluenesulfonyl chloride (pTsCl). The reaction was stirred for 12 hours, at which time diethyl ether (30 mL) was added. The mixture was transferred to a separatory funnel, and a saturated solution of NaHCO$_3$ (40 mL) was added. The organic layer was dried with MgSO$_4$, filtered, and concentrated to a residue, which was chromatographed on a silica gel column with a 10% to 50% gradient of ethyl acetate/hexanes. Rf=0.69 (ethyl acetate, 254 nm UV). This material was then dissolved in N,N-dimethylformamide (5 mL), and sodium azide (266 mg, 4.09 mmol) was added and the reaction was stirred at ambient temperature for 16 hours, at which time the reaction mixture was diluted with diethyl ether (30 mL) and washed with a saturated solution of NaHCO$_3$ (3×30 mL), then with brine (25 mL), dried with MgSO$_4$, filtered and concentrated in vacuo. The resulting residue was chromatographed over silica gel with a 15% to 50% gradient of ethyl acetate/hexanes to furnish 100 mg (30% yield) of this compound as a light yellow oil. Rf=0.68 (ethyl acetate, 254 nm UV). $^1$H NMR (400 MHz, CDCl$_3$): 8.34 (d, J=5.6 Hz, 1H,), 6.81 (d, J=2.4 Hz 1H), 4.39 (s, 2H), 3.81 (s, 3H).

Synthesis of 2-azidomethyl-4-chloropyridine

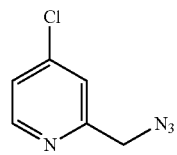 [SMILES: [N-]=[N+]=NCc1cc(Cl)ccn1]

2-azidomethyl-4-chloropyridine was prepared and characterized as described in Jung, F. H., Cephalosporin derivatives. EP Patent No. 0127992. Dec. 12, 1984.

Synthesis of tert-Butyl (6-azidomethylpyridin-3-yl)carbamate

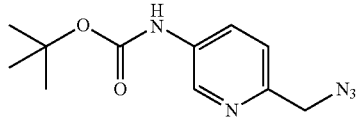 [SMILES: CC(C)(C)OC(=O)Nc1ccc(CN=[N+]=[N-])nc1]

tert-Butyl (6-(hydroxymethyl)pyridin-3-yl)carbamate (24 mg, 0.107 mmol) was dissolved in DMF (2 mL) and sodium azide (35 mg, 0.54 mmol) was added followed by the simultaneous addition of carbon tetrabromide (179 mg, 0.54 mmol) and triphenylphosphine (142 mg, 0.54 mol). The mixture was stirred for 2 hours at ambient temperature, then diluted in ethyl acetate (20 mL) and saturated NaHCO$_3$ solution (20 mL). The layers were separated, and the organic layer was dried with MgSO$_4$, filtered, and concentrated to a yellow oil, which was chromatographed (15-90% ethyl acetate/hexanes on silica gel) to afford this compound as a film 16.8 mg (63%). Rf=0.92 (ethyl acetate, 254 nm UV). MS (ESI+): 250.0 (M+H+, 100%; 194.0, 25%).

Synthesis of 5-carbomethoxy nicotinic acid

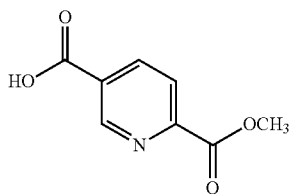 [SMILES: COC(=O)c1ccc(C(=O)O)cn1]

This compound was prepared and characterized as described in Luk, K-C., So, S-S., Zhang, J., and Zhang, Z. Preparation of oxindoles as inhibitors of MDM2-p53 interaction for the treatment of cancer. WO2006136606. Dec. 28, 2006.

Synthesis of 5-(2,5-dioxopyrrolidin-1-yl) 2-methyl pyridine-2,5-dicarboxylate

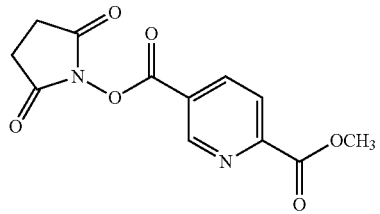 [SMILES: COC(=O)c1ccc(C(=O)ON2C(=O)CCC2=O)cn1]

5-carbomethoxy nicotinic acid (100 mg, 0.55 mmol) was dissolved in dichloromethane (10 mL) at ambient temperature. N-Hydroxysuccinimide (NHS; 95 mg, 0.83 mmol) was added, followed by 1-ethyl-3-(3-dimethylaminopropyl)carbodiimide) hydrochloride (133 mg, 0.69 mol) and the mixture stirred at ambient temperature for 2 hours. The mixture was then diluted with chloroform (15 mL), followed by the addition of 2% HCl solution (15 mL). The organic layer was washed with water (15 mL), dried with MgSO₄, and filtered. This compound was used directly in the next step without further purification. Rf=0.53 (ethyl acetate, 254 nm UV).

Synthesis of methyl 5-(2-(tert-butoxycarbonylamino)ethyl) carbamoyl picolinate

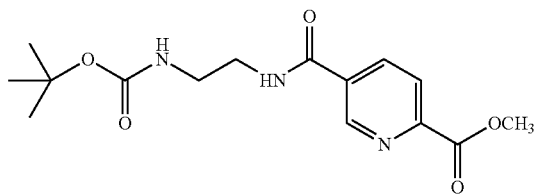 [SMILES: COC(=O)c1ccc(C(=O)NCCNC(=O)OC(C)(C)C)cn1]

5-(2,5-dioxopyrrolidin-1-yl) 2-methyl pyridine-2,5-dicarboxylate (155 mg, 0.55 mmol) was dissolved in dichloromethane (15 mL). N,N-diisopropylethylamine (0.30 mL, 1.65 mmol) was added at ambient temperature followed by tert-butyl (2 aminoethyl) carbamate hydrochloride (119 mg, 0.61 mmol). The reaction was stirred for 50 minutes, then diluted with dichloromethane (30 mL) and 2 M Na₂CO₃ solution (20 mL). The layers were separated and the organic layer was dried with MgSO₄, filtered and concentrated in vacuo. The residue was dissolved in warm methanol (3 mL), loaded onto a silica gel chromatography column and eluted with ethyl acetate then 95:5 ethyl acetate:methanol to provide 104 mg (58%) of this compound as a white solid. Rf=0.32 (ethyl acetate, 254 nm UV). $^1$H NMR (400 MHz, CDCl₃): 9.15 (d, J=2 Hz, 1H), 8.30 (d, J=1.6 Hz, 1H), 8.14 (complex, 2H), 5.32 (br s, 1H), 4.00 (s, 3H), 3.56 (m, 2H), 3.41 (m, 2H), 1.39 (s, 9H).

Synthesis tert-butyl (2-(6-(hydroxymethyl)nicotinamido)ethyl) carbamate

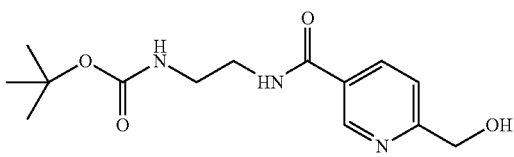 [SMILES: CC(C)(C)OC(=O)NCCNC(=O)c1ccc(CO)nc1]

NaBH₄ (55 mg, 1.46 mmol) was added slowly to methyl 5-(2-(tert-butoxycarbonylamino)ethyl) carbamoyl picolinate (157 mg, 0.49 mmol) dissolved in methanol (3 mL). THF (10 mL) was added and the reaction flask was placed in an oil bath preheated to 65° C. The reaction was stirred at 65° C. for 15 minutes, at which time 2 M Na₂CO₃ solution (6 mL) was added over 10 minutes followed by water (6 mL). The mixture was then concentrated to ⅕ of its original volume and chromatographed directly with 0.5% triethylamine and ethyl acetate/methanol to provide this compound (132 mg, 91%) as a white solid. Rf=0.10 (ethyl acetate, 254 nm UV). $^1$H NMR (400 MHz, d6-DMSO): 8.89 (s, 1H), 8.61 (s, 1H), 8.18 (d, J=8.0 Hz, 1H), 7.55 (d, J=8.0 Hz, 1H), 6.93 (m, 1H), 5.53 (br s, 1H), 4.61 (s, 2H), 3.29 (m, 2H), 3.12 (d, J=6.0 Hz, 2H), 2.51 (s, 2H), 1.7 (s, 9H).

Synthesis of tert-butyl (2-(6-(azidomethyl)nicotinamido)ethyl) carbamate

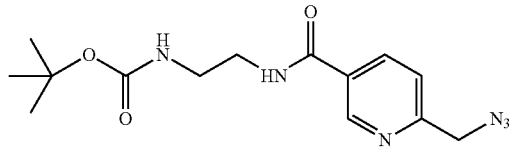 [SMILES: CC(C)(C)OC(=O)NCCNC(=O)c1ccc(CN=[N+]=[N-])nc1]

tert-butyl (2-(6-(hydroxymethyl)nicotinamido)ethyl) carbamate (132 mg, 0.45 mmol) was dissolved in DMF (5 mL). Sodium azide (218 mg, 3.36 mmol) was added, followed by triphenylphosphine (129 mg, 0.492 mmol) and carbon tetrabromide (189 mg, 185 mg, 0.56 mmol). The reaction was stirred for 1 hour at ambient temperature, at which time 2 M Na₂CO₃ solution (10 mL) was added followed by ethyl acetate (30 mL). The organic layer was washed with saturated NaHCO₃ solution (2×15 mL), dried with MgSO₄, filtered, and concentrated in vacuo. The resulting clear oil was purified by silica gel chromotagraphy using ethyl acetate as eluent to furnish this compound as a white solid. Rf=0.30 (ethyl acetate, 254 nm UV). $^1$H NMR (400 MHz, CDCl₃): 9.04 (d, J=1.6 Hz, 1H), 8.19 (dd, J=8.1, 2.3 Hz, 1H), 7.72 (br s, 1H), 7.43 (d, J=8.1 Hz, 1H), 5.17 (t, J=8.1 Hz, 5.8 Hz, 1H), 4.55 (s, 2H), 3.58 (q, J=4.9 Hz, 2H), 3.43 (q, J=5.9 Hz, 2H), 1.43 (s, 9H). LCMS (ESI+): 296.50 (MH+, 100%), 240.38 (86%); T$_R$=8.8 min.

Synthesis of tert-butyl 2-(2-(hydroxymethyl)pyridin-4 ylamino) ethylcarbamate

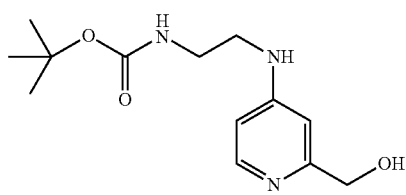 [SMILES: CC(C)(C)OC(=O)NCCNc1ccnc(CO)c1]

To a 40 mL pressure tube equipped with a stir bar was added 4-chloro-2-pyridylmethanol (0.25 g, 1.74 mmol), N,N-diisopropylethylamine (1.52 mL, 8.71 mmol), and toluene (0.925 mL; 8.71 mmol) was added tert-butyl (2-aminoethyl)carbamate (0.55 g, 3.50 mmol). The vessel was purged with argon and then placed in an oil bath pre-heated to 125° C. The temperature of the oil bath was increased to 140° C. over 30 minutes. After 2 hours, TLC (conditions below) indicated near complete consumption of the starting material. The reaction was cooled to ambient temperature and the toluene layer was decanted. Methanol (15 mL) was added and the mixture was heated to ca. 40° C. for 5 minutes to break up the solid residual. After concentrating the mixture down to ⅕ of its original volume, CHCl₃ (5 mL) was added and the residue was loaded onto a 5 cm×15 cm silica gel column equilibrated with dichloromethane (DCM)+0.5% triethylamine Flash chromatography with DCM to DCM/10% Methanol with 0.5% triethylamine provided an inseparable mixture of the compound and starting tert-butyl (2-aminoethyl)carbamate (1:1.4 molar ratio). Rf=0.38 (15% MeOH/DCM+0.1% TEA, 254 nm UV). This mixture was used in the next step without further purification. $^1$H NMR (400 MHz, CD$_3$OD): (9) 7.93 (d, J=5.6 Hz, 1H), 6.75 (d, J=2.4 z, 1H), 6.48 (dd, J=6.0, 2.4 Hz, 1H), 4.54 (s, 2H), 3.66 (s, 1H), 3.26 (m, 4H), 1.46 (s, 9H); (tert-butyl 2-aminoethylcarbamate) 3.33 (m, 2H), 3.12 (t, J=6.4 Hz, 2H), 2.71 (t, J=6.4 Hz, 2H), 1.44 (s, 9H).

Synthesis of tert-butyl 2-(2-(azidomethyl)pyridin-4-ylamino) ethylcarbamate

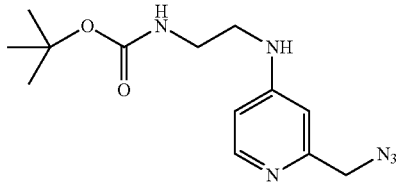 [SMILES: CC(C)(C)OC(=O)NCCNc1ccnc(CN=[N+]=[N-])c1]

The mixture of tert-butyl 2-(2-(hydroxymethyl)pyridin-4-ylamino) ethylcarbamate and tert-butyl (2-aminoethyl)carbamate was dissolved in DMF (3.5 mL) in a 20 mL screw top vial. Sodium azide (91 mg, 1.40 mmol) was added followed by the simultaneous addition of triphenylphosphine (370 mg, 1.40 mmol) and carbon tetrabromide (470 mg, 1.40 mmol) at ambient temperature. After 1 hour, additional sodium azide 91 mg (1.40 mmol) was added followed by the simultaneous addition of triphenylphosphine (370 mg, 1.40 mmol) and carbon tetrabromide (470 mg, 1.40 mmol). The reaction was stirred for another hour and concentrated under a stream of nitrogen to remove the solvent. The resulting residue was chromatographed with 1% to 10% MeOH/CHCl$_3$ to provide this compound as a white solid (75 mg, 27% over 2 steps). Rf=0.22 (5% MeOH/DCM+0.1% TEA, 254 nm UV). $^1$H NMR (400 MHz, CD$_3$OD): 8.00 (d, J=6.4 Hz, 1H), 6.71 (d, J=1.6 Hz, 1H), 6.63 (dd, J=6.0, 2.0 Hz, 1H), 4.38 (s, 2H), 3.33 (m, 2H; overlaps with residual MeOH), 3.25 (m, 2H), 1.96 (s, 2H), 1.44 (s, 9H). MS (ESI+): 293.3 (M+H+).

Synthesis of 2-azidoethylpyridine

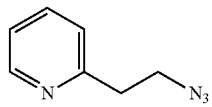 [SMILES: [N-]=[N+]=NCCc1ccccn1]

2-azidoethylpyridine was prepared and characterized as described by Brotherton, W. S.; Michaels, H. A.; Simmons, J. T.; Clark, R. J.; Dalai, N. S.; Zhu, L. *Organic Letters* 2009, 11, 4954 4957.

Synthesis of 3-azido-1-(pyridin-2-yl)propan-1-one

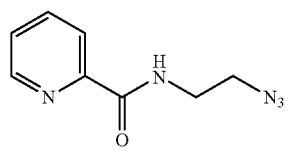 [SMILES: [N-]=[N+]=NCCNC(=O)c1ccccn1]

2-picolinic acid (74 mg, 0.60 mmol) was dissolved in anhydrous dichloromethane (4 mL) under Argon. Triethylamine (0.84 mL, 6.0 mmol) was then added followed by ethyl chloroformate (86 µL, 0.90 mmol). The reaction mixture was stirred for 30 minutes at ambient temperature, at which time 2-azidoethlamine hydrochloride (11 mg, 0.90 mmol) was added. After further stirring at ambient temperature for 12 hours, the solvent was removed in vacuo and the resulting residue was taken up in ethyl acetate, loaded onto a preparatory TLC plate, and developed using 4:1 hexanes: ethyl acetate solvent system. The product-containing band was collected and rinsed with 10:1 chloroform:methanol, filtered, and concentrated to a yellow oil (25 mg, 22%). Rf=0.64 (ethyl acetate, u.v.). $^1$H NMR (400 MHz, CDCl$_3$): 8.76 (d, J=4 Hz, 1H), 8.14 (d, J=8 Hz, 1H), 7.83 (dd, J=7.6, 6.4 Hz, 1H), 7.47 (m, 1H), 4.49 (dd, J=7.2, 6.8 Hz, 2H), 3.95 (s, 1H), 1.45 (t, J=7.2 Hz, 3H).

Synthesis of 2-Azidomethylquinoline

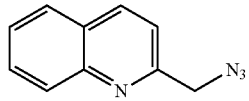 [SMILES: [N-]=[N+]=NCc1ccc2ccccc2n1]

2-Azidomethylquinoline was prepared and characterized as described by Brotherton, W. S.; Michaels, H. A.; Simmons, J. T.; Clark, R. J.; Dalai, N. S.; Zhu, L. *Organic Letters* 2009, 11, 4954 4957.

Synthesis of 6-bromomethyl-2,2'-bipyridine

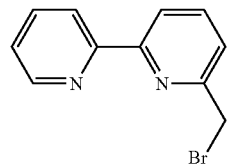 [SMILES: BrCc1cccc(-c2ccccn2)n1]

6-bromomethyl-2,2'-bipyridine was prepared and characterized as described by Murashima, T.; Tsukiyama, S.; Fujii, S.; Hayata, K.; Sakai, H.; Miyazawa, T.; Yamada, T. *Organic & Biomolecular Chemistry* 2005, 3, 4060-4064.

Synthesis of 6-Azidomethyl-2,2'-bipyridine

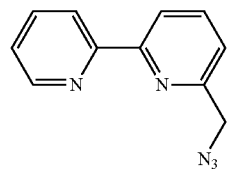 [SMILES: [N-]=[N+]=NCc1cccc(-c2ccccn2)n1]

To the solution of 6-bromomethyl-2,2'-bipyridine (75 mg, 0.30 mmol) in DMF (2 mL) was added sodium azide (59 mg, 0.90 mmol). The reaction mixture was stirred for 2 hours, then diluted with diethyl ether (20 mL) and saturated NaHCO$_3$ solution (15 mL). The layers were separated and the organic layer was further washed with saturated NaHCO$_3$ solution (2×15 mL), dried with MgSO$_4$, filtered, and concentrated to an oil. LC-MS (ESI+): 221.39 (MH+, 44%); TR=17.4 min.

Synthesis of 2-azidomethylbenzimidazole

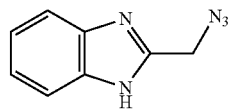 [SMILES: [N-]=[N+]=NCc1nc2ccccc2[nH]1]

2-azidomethylbenzimidazole was prepared and characterized as described by Hideg, K.; Hankovszky, H. O. *Synthesis-Stuttgart* 1978, 313-315.

Synthesis of 5-(6-(Azidomethyl)nicotinamido)pentanoic acid

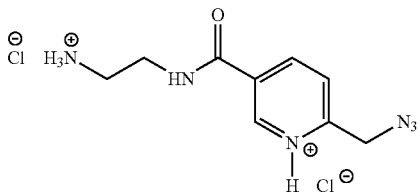 [SMILES: [Cl-] ; [N-]=[N+]=NCc1ccc(C(=O)NCC[NH3+])c[nH+]1 ; [Cl-]]

To a solution of 6-azidomethylnicotinic acid (30 mg, 0.168 mmol) in anhydrous DMF (500 μL) was added disuccinimidyl carbonate (DSC; 65 mg, 0.253 mmol) and triethylamine (TEA; 120 μL, 0.840 mmol). The reaction was allowed to proceed for 3 hours at ambient temperature. The reaction mixture was diluted with chloroform and water. Layers were separated, and the aqueous layer was extracted with chloroform three times. The combined organic layer was washed with brine, dried over MgSO$_4$, and concentrated in vacuo. The residual mixture was purified by silica chromatography (1:1 hexanes:ethyl acetate) to afford the succinimidyl ester of 6-azidomethylnicotinic acid. Rf=0.67 in 9:1 chloroform:methanol.

To a solution of 5-azidomethylnicotinic acid succinimidyl ester (15 mg, 0.055 mmol) in anhydrous DMF (500 μL) was added 5-aminovaleric acid (32 mg, 0.273 mmol) and TEA (38 μL, 0.273 mmol). The reaction proceeded for 12 hours at ambient temperature. TEA and DMF were then removed in vacuo, and the resulting residue was dry-loaded in 9:1 chloroform:methanol onto a silica column, and purified using 9:1 chloroform:methanol as eluent. Rf=0.19 in 9:1 chloroform:methanol. $^1$H NMR (D$_2$O, 500 MHz): 8.83 (s, 1H), 8.18 (d, 1H, J=8.5 Hz), 7.59 (d, 1H, J=8 Hz), 4.62 (s, 2H), 3.42 (m, 2H), 2.32 (m, 2H), 1.65 (m, 4H).

Synthesis of ALEXA FLUOR-647 (AF-647)-picolyl azide conjugate

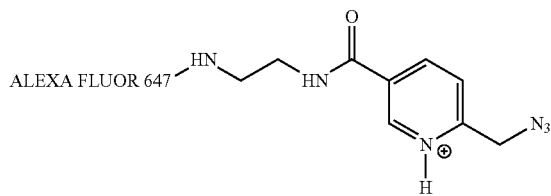

To a solution of 8-(2-aminoethyl)-6-(azidomethyl)nicotinamide (5.5 mg, 0.019 mmol) in DMF (0.95 mL) was added DIPEA (100 μL) and ALEXA FLUOR 647 succinimidyl ester (ALEXA FLUOR 647-SE; 20 mg, 0.016 mmol). After stirring at ambient temperature for 10 hours, the reaction mixture was concentrated and directly purified by preparative HPLC using a 30 minute gradient of 5-95% 10 mM NH4OAc/MeOH at a 1 mL/min flow rate. Fractions containing the product were combined and concentrated in vacuo. The residual was then dissolved in water (10 mL), flash-frozen, then lyophilized to yield 13.6 mg of ALEXA FLUOR-647-picolyl azide as a bright blue powder (83%). Tr=20.8 min at 647 nm. MS (ESI+): 1061.3 (M+H$^+$; 2%), 531.2, 6%); (ESI-): 1060.3 (Zwitterion, 17%), 540.3 (52%), 529.3 (M$^{2-}$. 100%). HPLC: >99% purity at 254 nm and 644 nm.

Synthetic Preparation of Fluorogenic Assay Reagents

To prepare the triazole adduct between 16 and, for example, 2-azidomethylpyridine, 16 (20 mg, 0.073 mmol) was dissolved in DMSO (4 mL). 2-azidomethylpyridine (20 mg, 0.15 mmol) was added followed by a 0.50 M solution of sodium ascorbate in water (59 μL, 0.029 mmol), and a 0.25 M copper(II) sulfate solution in water (30 μL, 0.007 mmol). The reaction was stirred for 1 hour and the solvent removed in vacuo. The crude reaction mixture was taken up in methanol and loaded directly onto a preparative TLC plate (0.25 mm thickness) and the plate was developed with 95:5 acetonitrile:H2O. The product-containing silica was collected and sonicated in chloroform (30 mL) for 3 minutes and filtered. The filtrate was concentrated to deliver 8.9 mg of II (30% yield) as a tan solid. Rf=0.80 (97:3 acetonitrile:H2O). $^1$H NMR (400 MHz, CDCl$_3$): 12.27 (br s, 1H), 8.58 (dd, J=4.8, 4.0 Hz, 1H), 7.92-7.82 (m, 3H), 7.44-7.35 (m, 3H), 5.81 (s, 1H), 5.44 (s, 1H), 4.51 (s, 2H), 3.37 (s, 4H), 2.71 (J=7.6, 6.0 Hz, 1H), 2.57 (t, J=7.6, 6.0 Hz, 1H). Excitation maxima=325 nm, emission maxima=415 nm (100 mM Tris buffer with 25% 1,2-propanediol). LC-MS (ESI+): 435.48 (MH+, 100%), 407.49 (65%); TR=8.4 min FIG. 5B shows the results of certain click reactions in the presence of 31 μM Cu and THPTA at a ratio of 4:1 (THPTA:Cu).

Various azides (R—N$_3$), including those shown below:

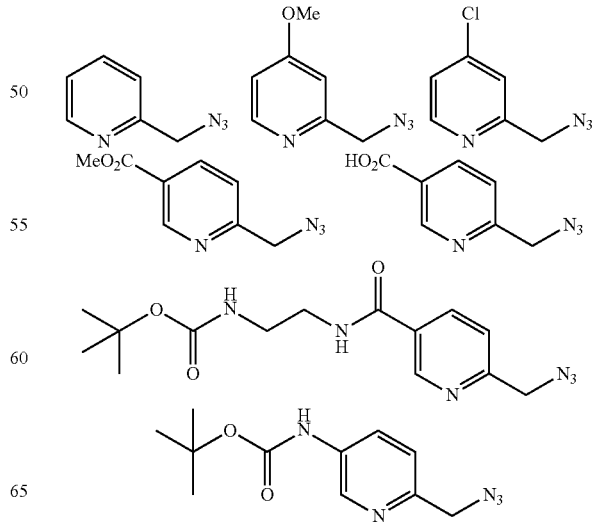

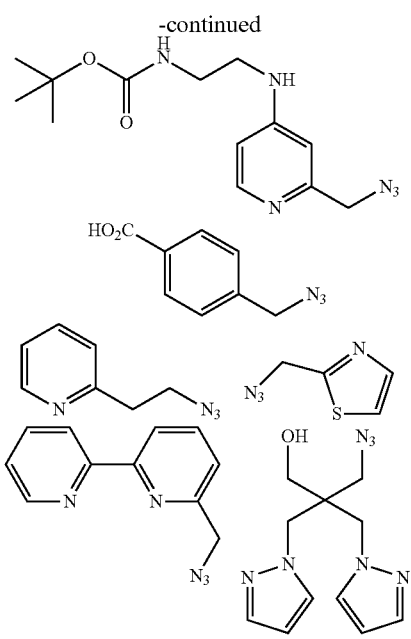

were reacted with 16.

Stock solutions of 16 and the azide compounds were prepared in 100 mM Tris buffer containing 25% 1,2-propanediol, unless otherwise noted. Data were recorded on a SpectraMax M5 instrument with excitation performed at 320 nm and emission detection at 430 nm, with a cutoff at 420 nm. The instrument was set to kinetic mode. 96-well plates were used in the top-read mode for fluorescence measurement. The total volume in each well was 200 µL. $CuSO_4$/water solutions were always added last to the plate to initiate reaction and measurements were taken at least every minute for 60 minutes. When THPTA was included in the reaction, the THPTA:Cu ratio was 4:1. A fixed ratio of 16:1 sodium ascorbate:Cu was also employed. Reagent concentrations in the stock and final solutions were as follows:

| Component | Initial concentration | Final concentration |
|---|---|---|
| 16 | 100 µM | 40 µM |
| azides | 100 µM | 20 µM |

The results of that experiment are shown in FIG. 5.

Figure 5A:
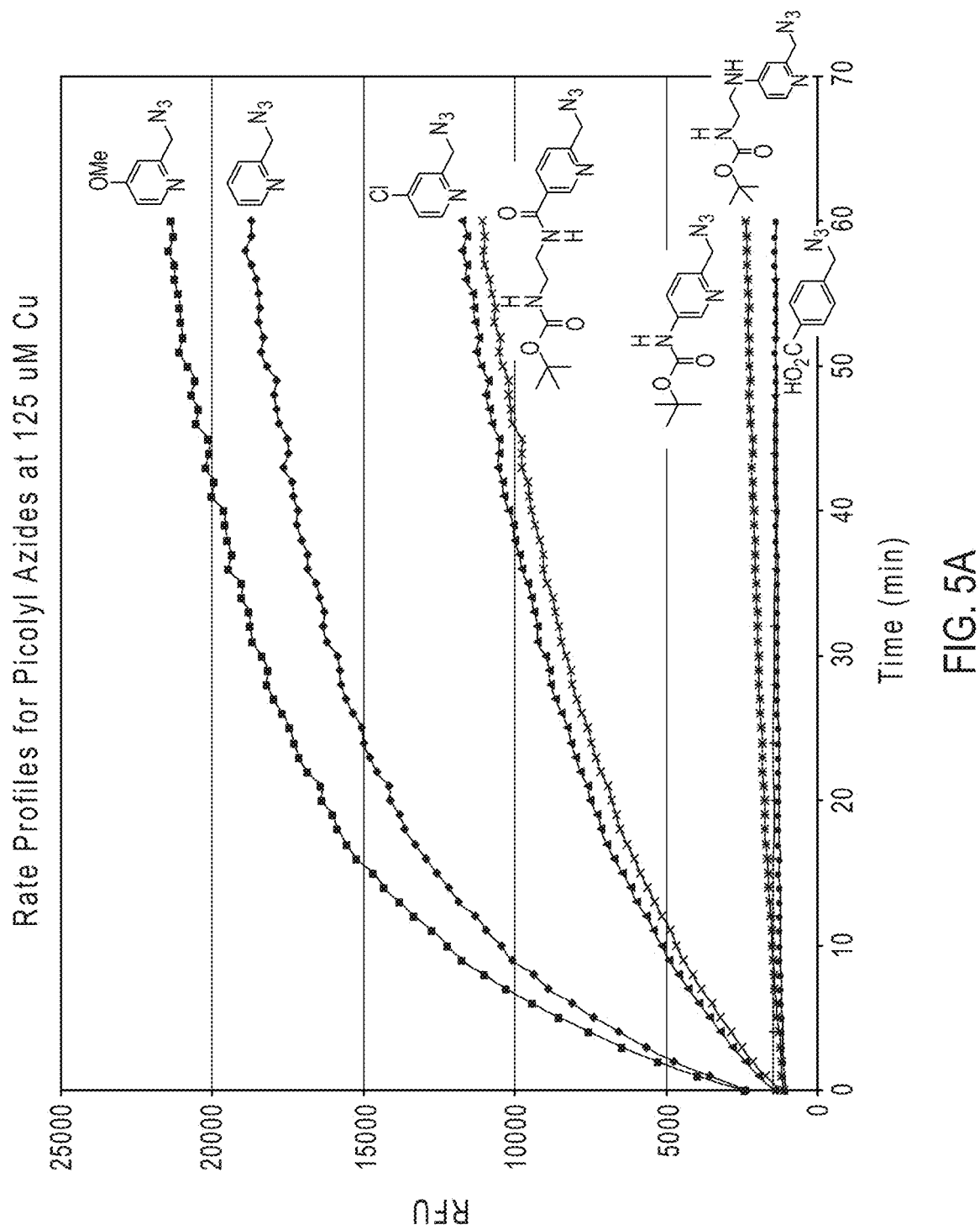
FIG. 5 shows shows the results of click reactions between a coumarin-alkyne (16) and various azides in the presence of (A) 125 µM Cu, or (B) 31 µM Cu, with or without THPTA at a ratio of 4:1 (THPTA:Cu), as described in Example 4.
Figure 5B:
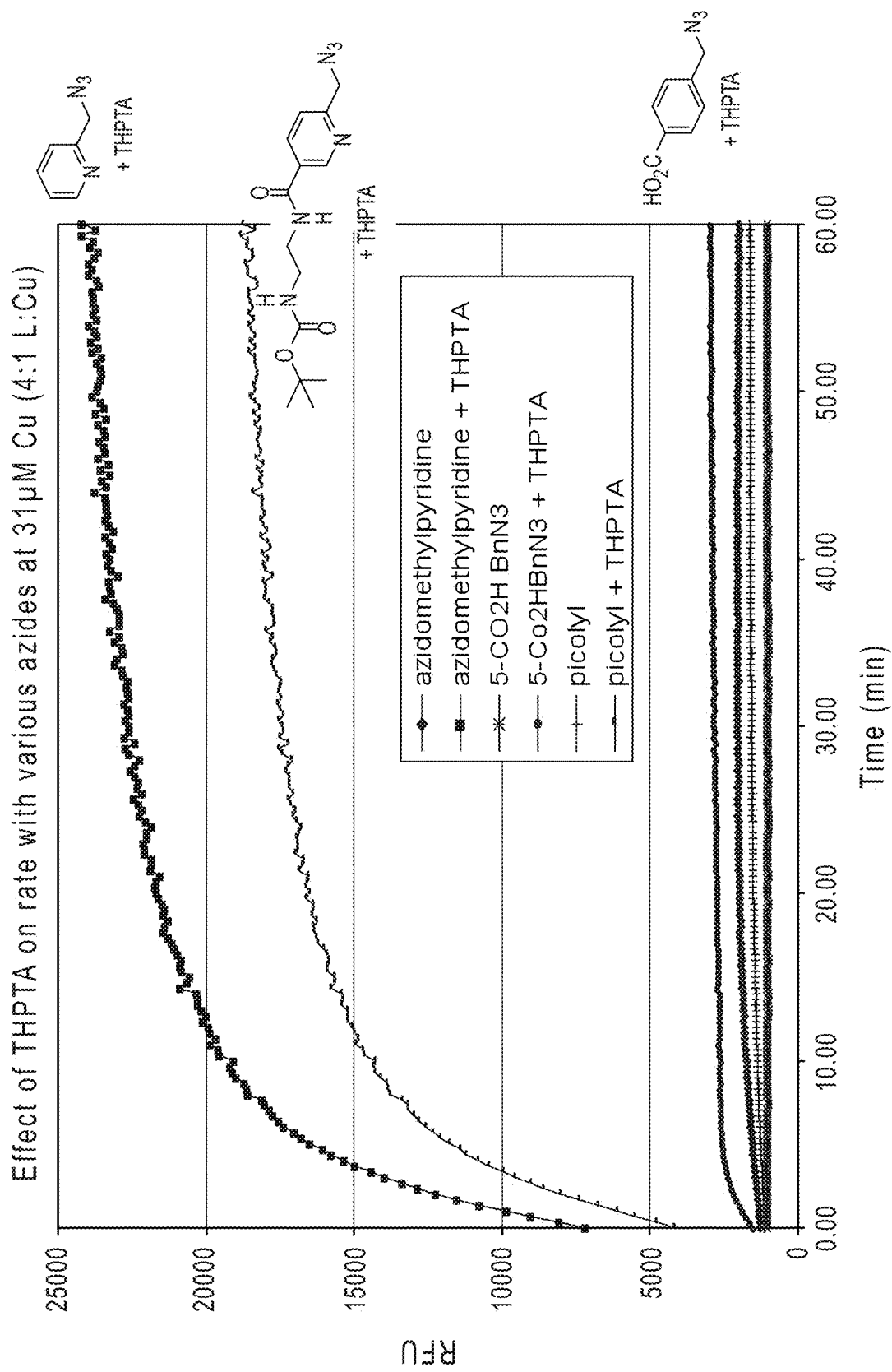

FIG. 5A shows the results of certain click reactions in the presence of 125 µM Cu. From FIG. 5A, it can be seen that 6-(azidomethyl)nicotinic acid undergoes click reactions much faster than 4-(azidomethyl)benzoic acid. This is believed to be due to the heteroatom of 6-(azidomethyl) nicotinic, which coordinates to Cu ions and in turn accelerates the rate of reaction.

FIG. 5B shows the additive effect that ligands such as THPTA have when added to the reaction of picolyl azides. Click reactions are faster when a combination of epically groups and ligands are used. Even when 4-azidomethylbenzoic acid is reacted with an alkyn in the presence of THPTA, the Click reaction is much slower than when a picolyl azide is used with our without a ligand such as THPTA.

A summary of azide heterocyclic structures and their copper(I) catalyzed azide-alkyne cycloaddition reaction conversions after 5 min and 30 min reaction times is shown below. Concentrations used were 20 µM azide, 40 µM 7-ethynyl coumarin, 125 µM CuSO4, and 4 mM sodium ascorbate. Reactions were performed in 100 µM Tris pH 7.4 with 25% v/v 1,2 propanediol at 25° C.

| Azide Structure | Conversion (%) after 5 min | Conversion (%) after 30 min |
|---|---|---|
| benzyl azide | <1 | <1 |
| 2-(azidomethyl)pyridine | 35 | 80 |
| 4-(azidomethyl)benzoic acid | <1 | 1.4 |
| 6-(azidomethyl)nicotinic acid | 19 | 49 |
| methyl 6-(azidomethyl)nicotinate | 9.4 | 22 |

-continued

| Azide Structure | Conversion (%) after 5 min | Conversion (%) after 30 min |
|---|---|---|
| 4-methoxy-2-(azidomethyl)pyridine | 41 | 94 |
| 4-chloro-2-(azidomethyl)pyridine | 14 | 40 |
| tert-butyl (6-(azidomethyl)pyridin-3-yl)carbamate | 2.6 | 5.5 |
| N-(2-(3,3-dimethylbutanamido)ethyl)-6-(azidomethyl)nicotinamide | 14 | 37 |
| tert-butyl (2-((2-(azidomethyl)pyridin-4-yl)amino)ethyl)carbamate | 1.8 | 2.7 |
| 2-(2-azidoethyl)pyridine | 12 | 24 |
| N-(2-azidoethyl)picolinamide | <1 | <1 |
| 2-(azidomethyl)quinoline | 7.8 | 20 |
| 6-(azidomethyl)-2,2'-bipyridine | <1 | <1 |

-continued

| Azide Structure | Conversion (%) after 5 min | Conversion (%) after 30 min |
|---|---|---|
| 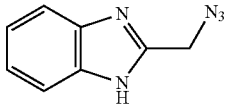 [SMILES: [N-]=[N+]=NCc1nc2ccccc2[nH]1] | <1 | <1 |

Several trends are apparent.

First, 2-picolyl azide and 6-(azidomethyl)nicotinic acid are much faster reactants than their carbocyclic analogues, benzyl azide and 4-(azidomethyl)benzoic acid, giving >35-fold and >19-fold improvements in initial CuAAC rates under these conditions.

Second, among the picolyl azide structures, an azide with an electron donating group gives a faster rate than one with electron withdrawing groups, presumably because the former enhances the chelating strength of pyridyl nitrogen. An exception is the picolyl azide with an alkyamino substituent, which gives little conversion after 30 min.

A third observation is that azido compounds with other copper-coordinating motifs generally did not have as strong an accelerative effect as 2-picolyl azide. 2-azidoethylpyridine, which contains an additional methylene spacer between the pyridyl ring and the azido group (to give a six-membered chelate ring), gave at least ~3-fold less product after 5 min than picolyl azide. 6-azidomethyl-2,2'-bipyridine and 2-(azidomethyl)benzimidazole each did not give any product after 30 min, despite being strong copper chelators.

Example 5

The stability of GFP in the presence of various concentrations of Cu(II), Cu(II) plus sodium ascorbate (to produce Cu(I)), and Cu(II) plus sodium ascorbate and THPTA, was determined as follows.

Figure 6A:
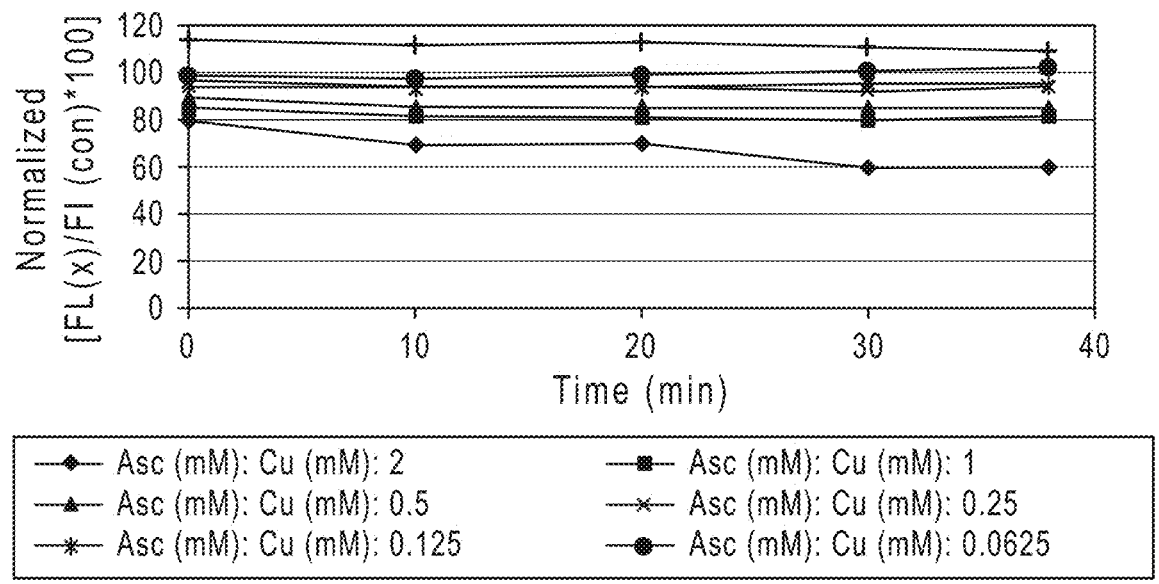
FIG. 6 shows the stability of GFP in the presence of (A) various concentrations of Cu(II), and (B) various concentrations of Cu(II) with sodium ascorbate, as described in Example 5.

GFP (5 nM) was incubated in 100 mM Tris buffer with 25% 1,2-propanediol at 25° C. in the presence of 2 mM, 1 mM, 0.5 mM, 0.25 mM, 0.125 mM, or 0.0625 mM CuSO$_4$. No ascorbate was included in the incubation mixtures. GFP fluorescence was then measured at various time intervals. As shown in FIG. 6A, at the highest concentration of CuSO$_4$, 2 mM, the GFP signal was 60% of maximum after 30 minutes in that experiment. GFP was found to be essentially stable at <0.5 mM Cu(II).

Figure 6B:
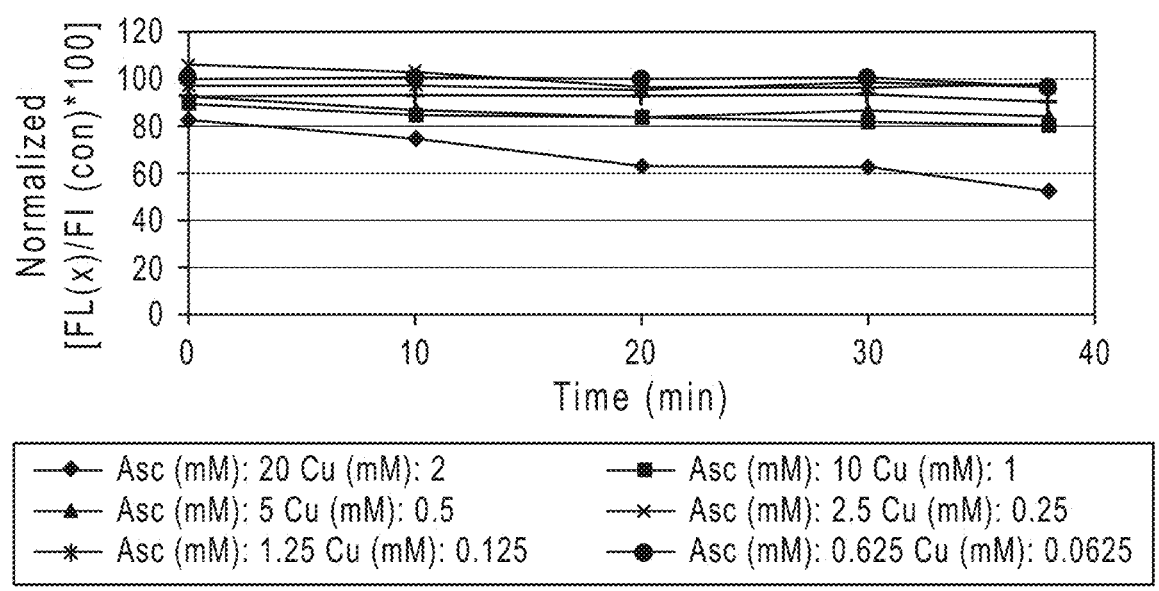

In the next experiment, 5 nM GFP was incubated in 100 mM Tris buffer with 25% 1,2-propanediol at 25° C. in the presence of 2 mM, 1 mM, 0.5 mM, 0.25 mM, 0.125 mM, or 0.0625 mM CuSO$_4$. In each mixture, sodium ascorbate was included at a concentration 10-fold greater than the Cu(II) concentration (i.e., for 1 mM Cu(II), 10 mM sodium ascorbate was included). GFP fluorescence was then measured at various time intervals. As shown in FIG. 6B, at the highest concentration of Cu(II) and sodium ascorbate (2 mM Cu(II) plus 20 mM sodium ascorbate), the GFP signal was 53% of maximum after 38 minutes in that experiment. GFP was found to be essentially stable at <0.25 mM Cu(II) plus 2.5 mM sodium ascorbate.

Figure 7A:
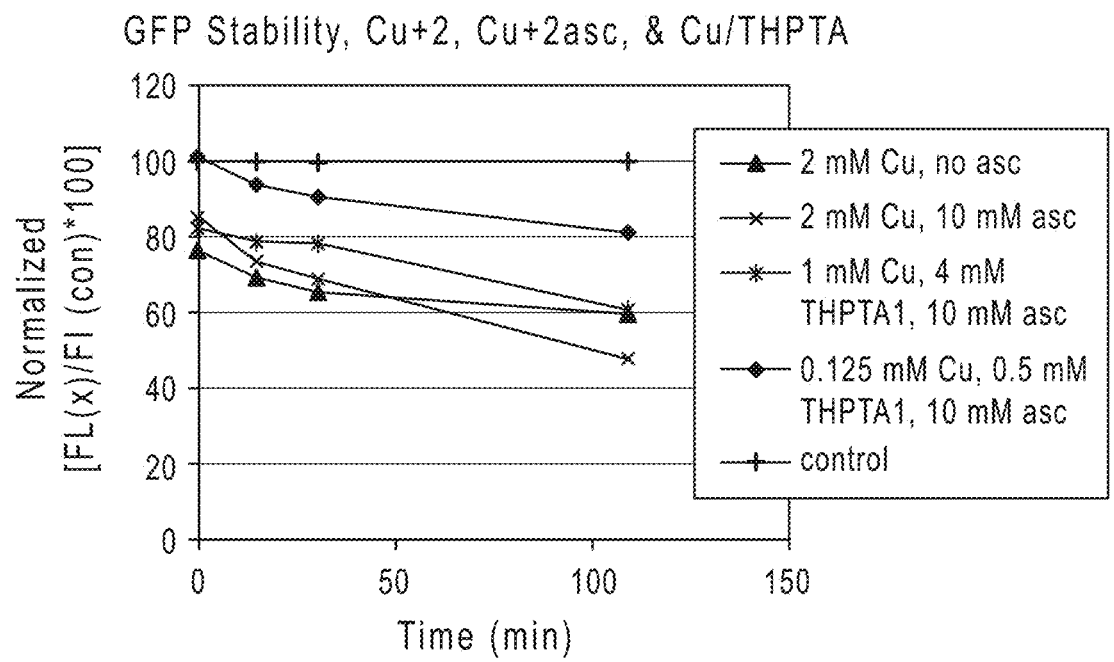
FIG. 7 shows (A) the stability of GFP in the presence of Cu(II), with or without ascorbate, and with or without THPTA, and (B) the rate of a click reaction between Oregon Green® alkyne and QSY azide under the same concentrations shown in (A), as described in Example 5.

Finally, GFP stability was determined in the presence of Cu(II), with and without sodium ascorbate, and with or without THPTA. In this experiment, 5 nM GFP was incubated in 100 mM Tris buffer with 25% 1,2-propanediol at 25° C. in the presence of (i) 2 mM Cu(II); (ii) 1 mM Cu(II), 10 mM sodium ascorbate; (iii) 1 mM Cu(II), 4 mM THPTA, 10 mM sodium ascorbate; or (iv) 0.125 mM Cu(II), 0.5 mM THPTA, and 10 mM sodium ascorbate. In this experiment, the mixtures were incubated for 30 minutes typically. As shown in FIG. 7A, the GFP signal gradually declined under all of the tested conditions in that experiment. The mixtures comprising THPTA and lower concentrations of Cu(II) showed less degradation of the GFP signal, compared to the mixtures with Cu(II) alone or Cu(II) plus ascorbate.

Figure 7B:
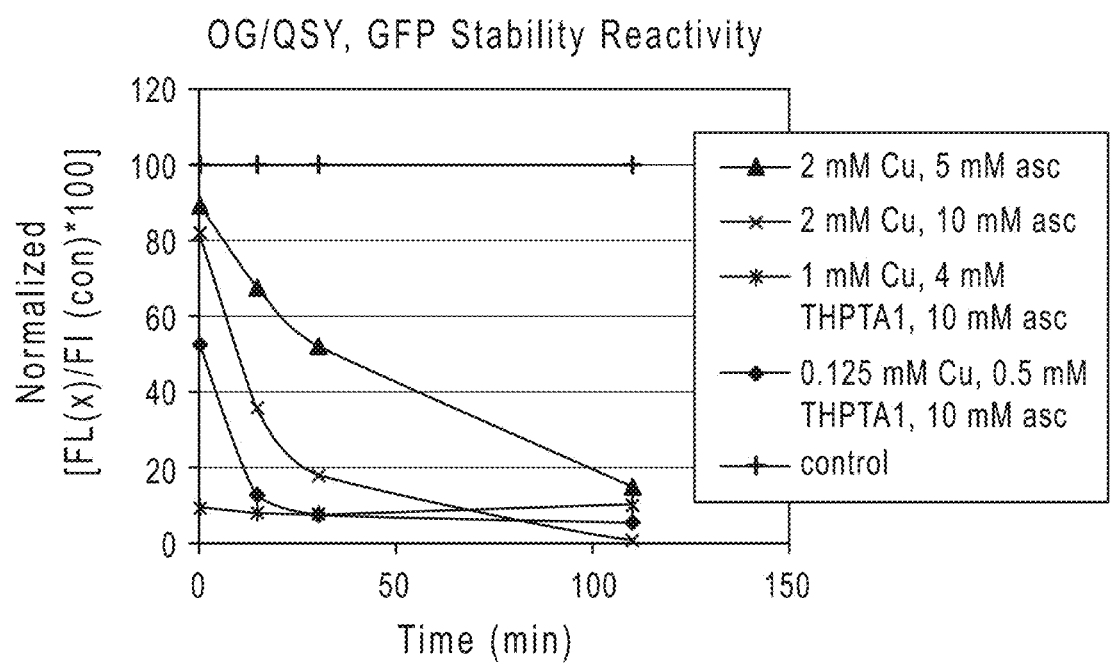
Figure 8:
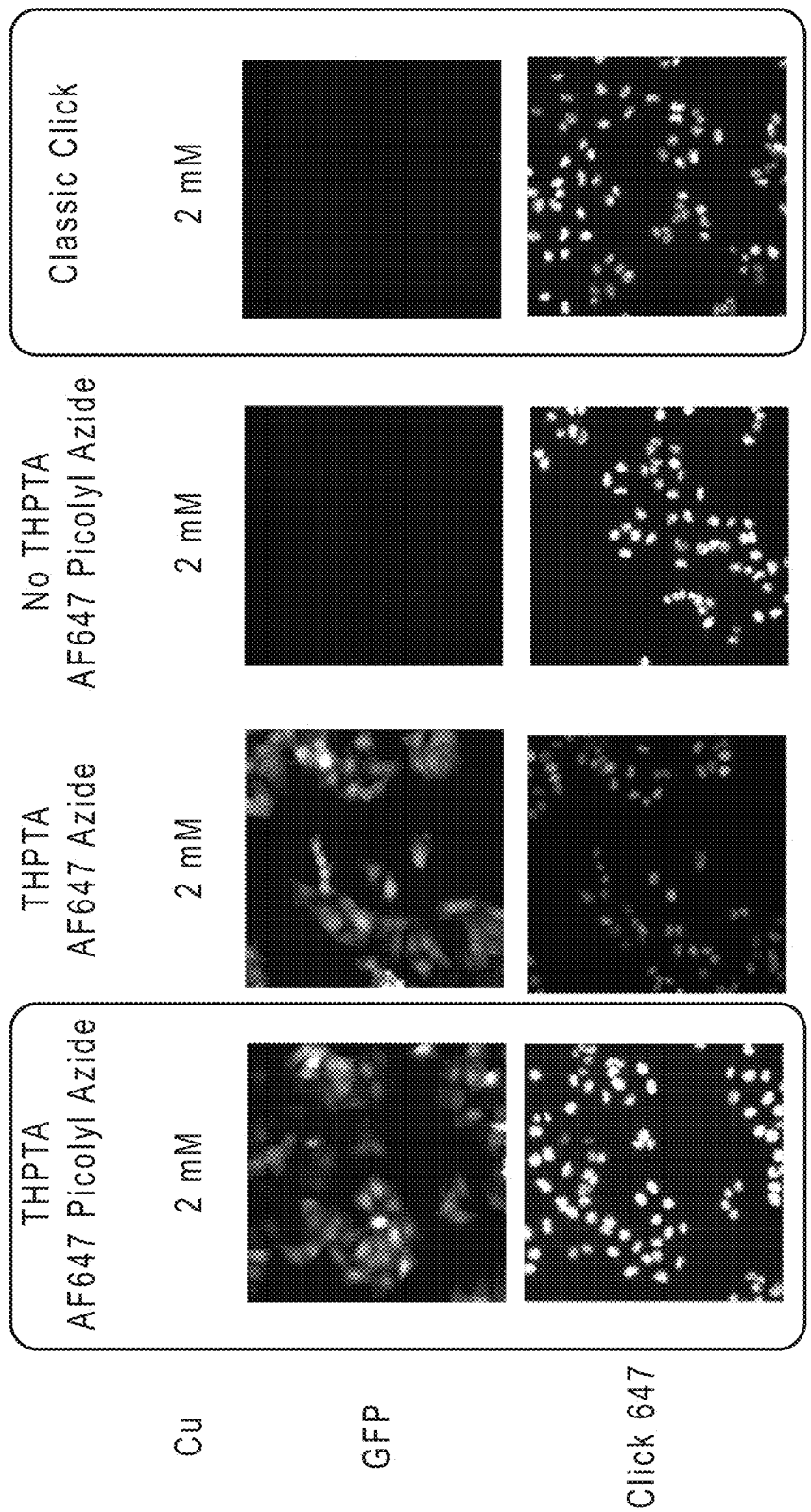
FIG. 8 shows Click Labeling of RNA with EU in presence of GPF with AF647-picolyl azide or AF647 azide with or without THPTA as ligand as described in Example 6.
Figure 9:
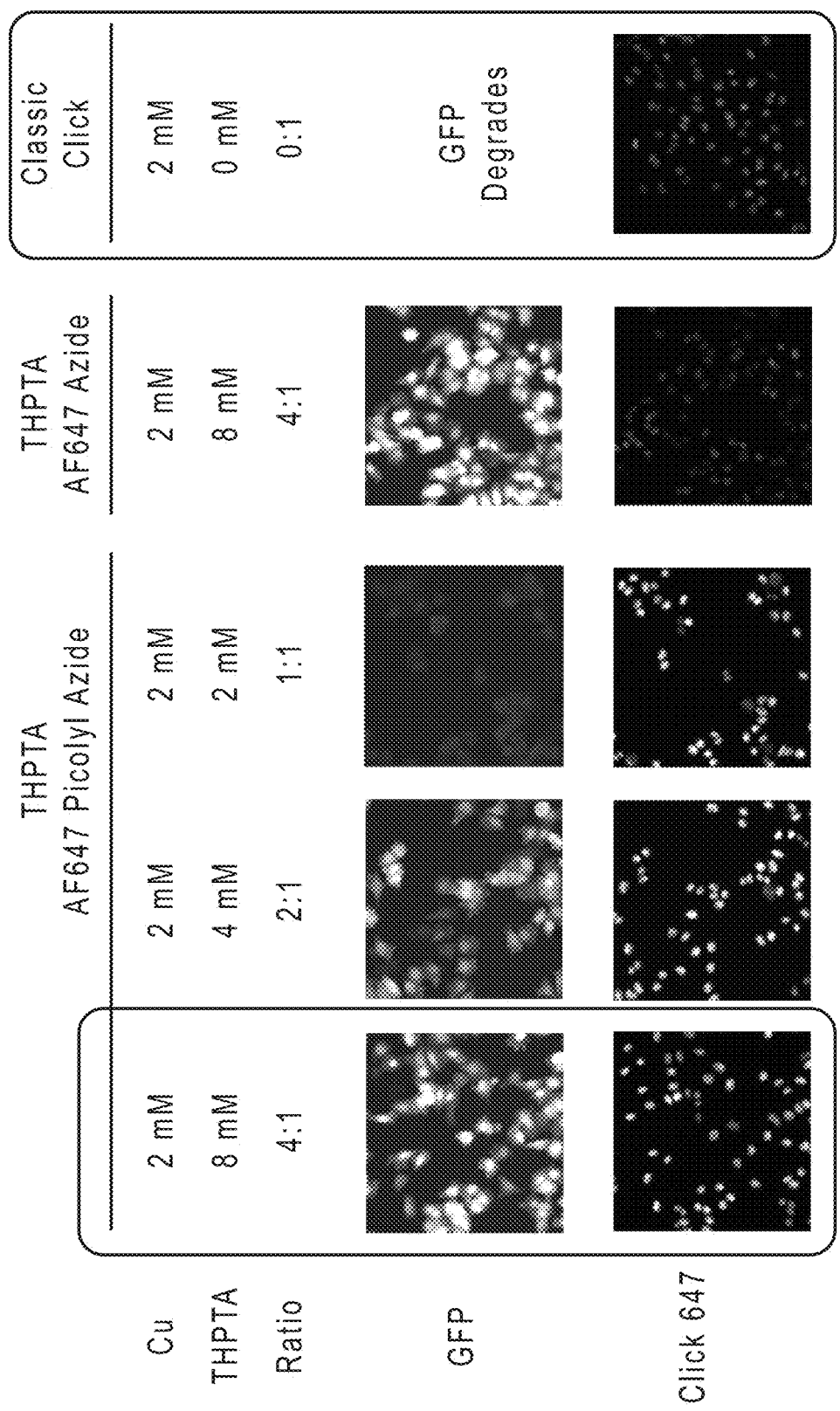
FIG. 9 shows Click Labeling of RNA with EU in presence of GPF with AF647-picolyl azide or AF647 azide with THPTA as ligand with various molar ratio of Cu:THPTA. as described in Example 6.
Figure 10:
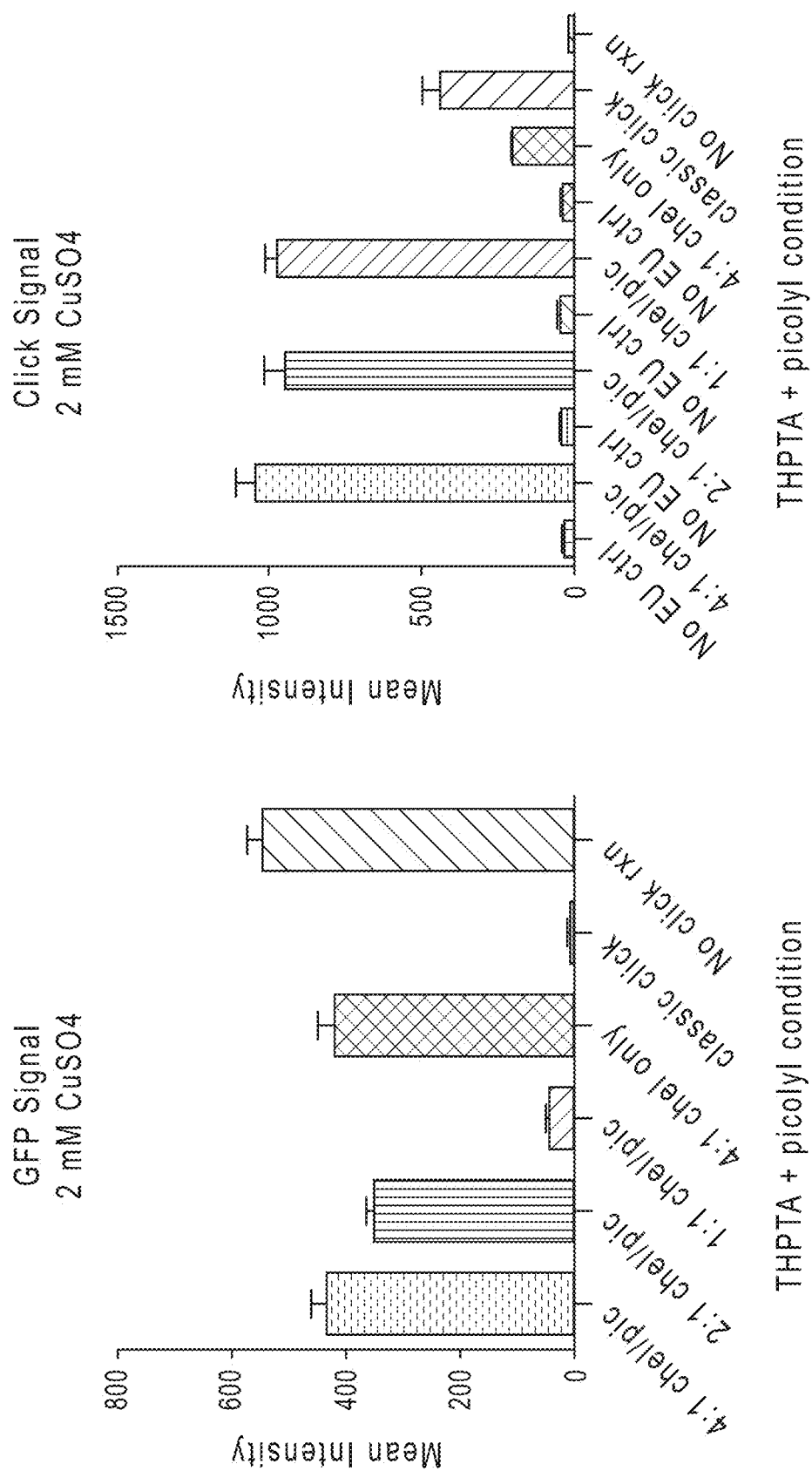
FIG. 10 shows Graphical representation of GFP stability and progression of click reaction at 2 mM copper as described in Example 6.
Figure 11:
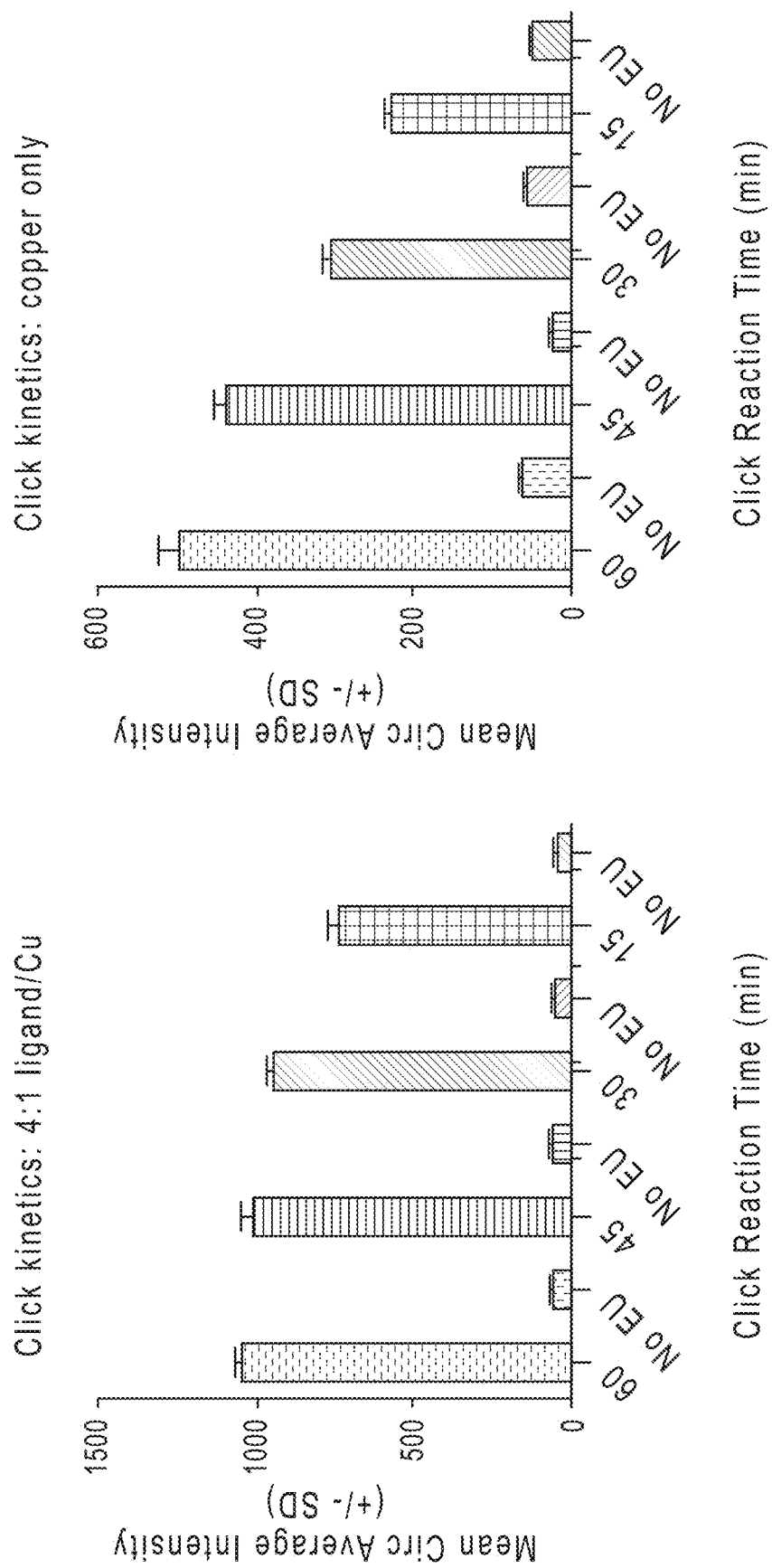
FIG. 11 shows Graphical representation of click reaction rate with or without THPTA at different molar ratios of Cu:THPTA as described in Example 6
Figure 12:
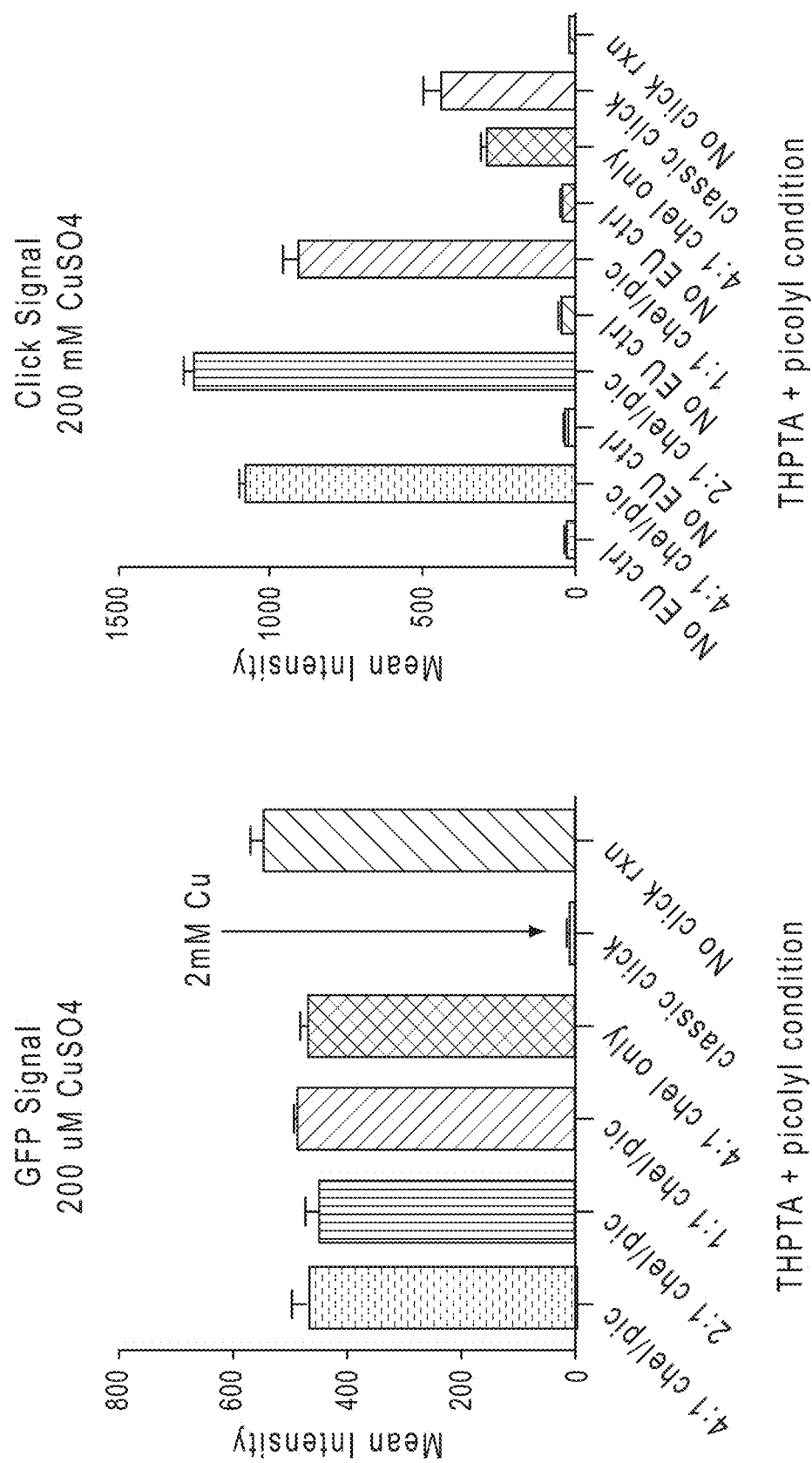
FIG. 12 shows Graphical representation of GFP stability and progression of click reaction at 200 µM copper
Figure 13:
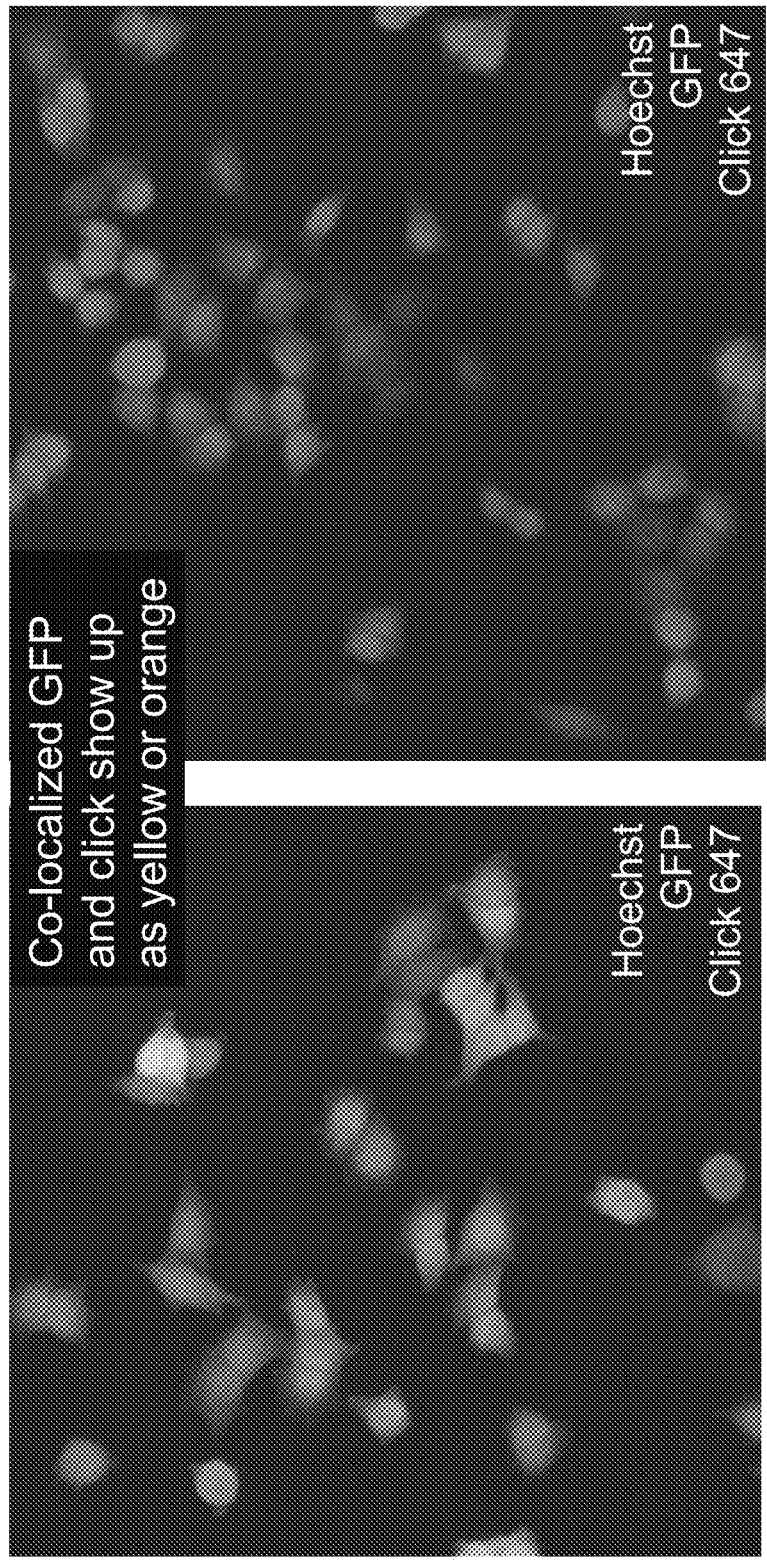
FIG. 13 shows Click Labeling of HPG with AF647-picolyl azide or AF647 azide in presence of GPF with THPTA as described in Example 7.
Figure 14:
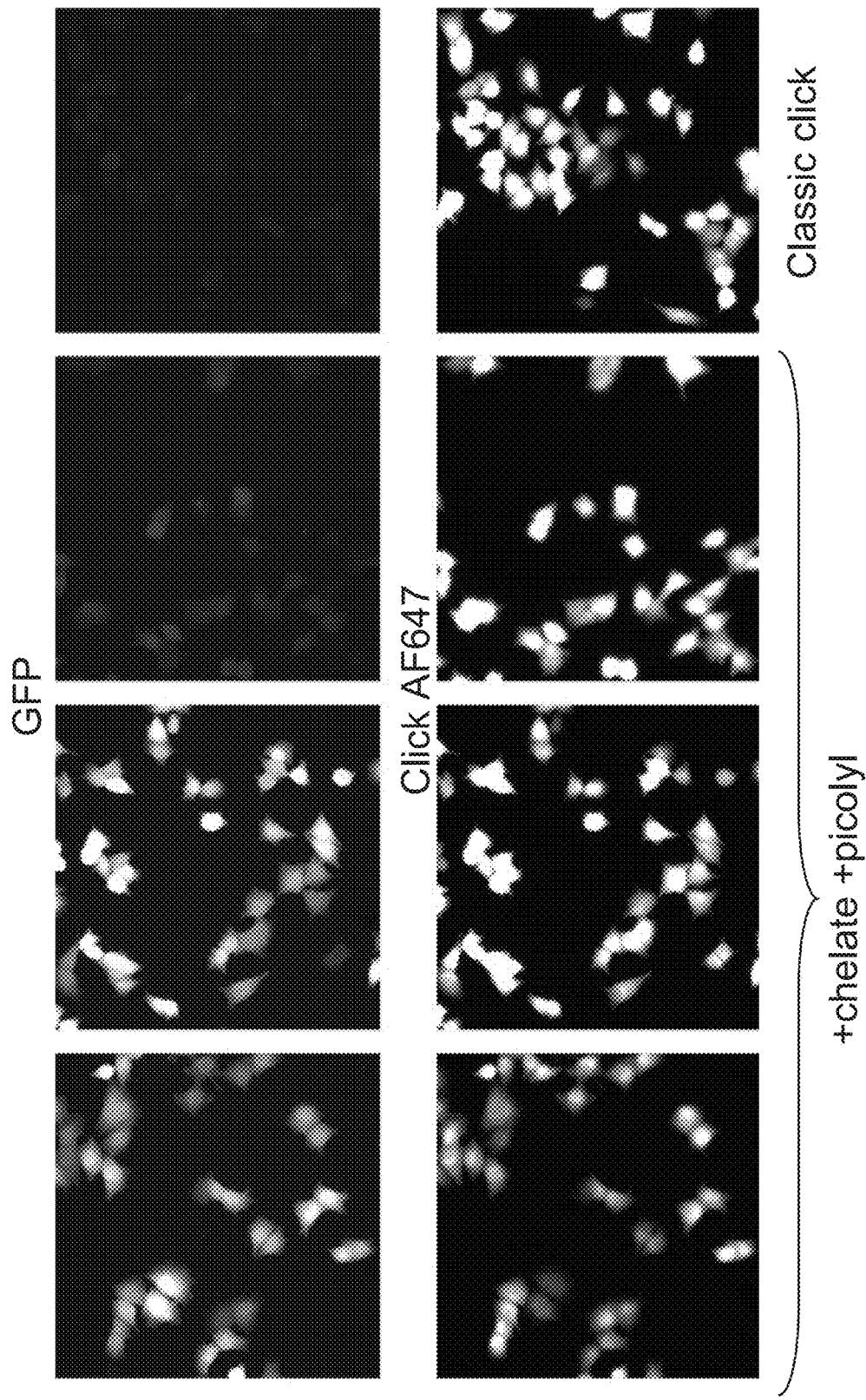
FIG. 14 shows click Labeling of HPG with AF647-picolyl azide or AF647 azide in presence of GPF with THPTA as ligand with various molar ratio of Cu:THPTA as described in Example 7.
Figure 15:
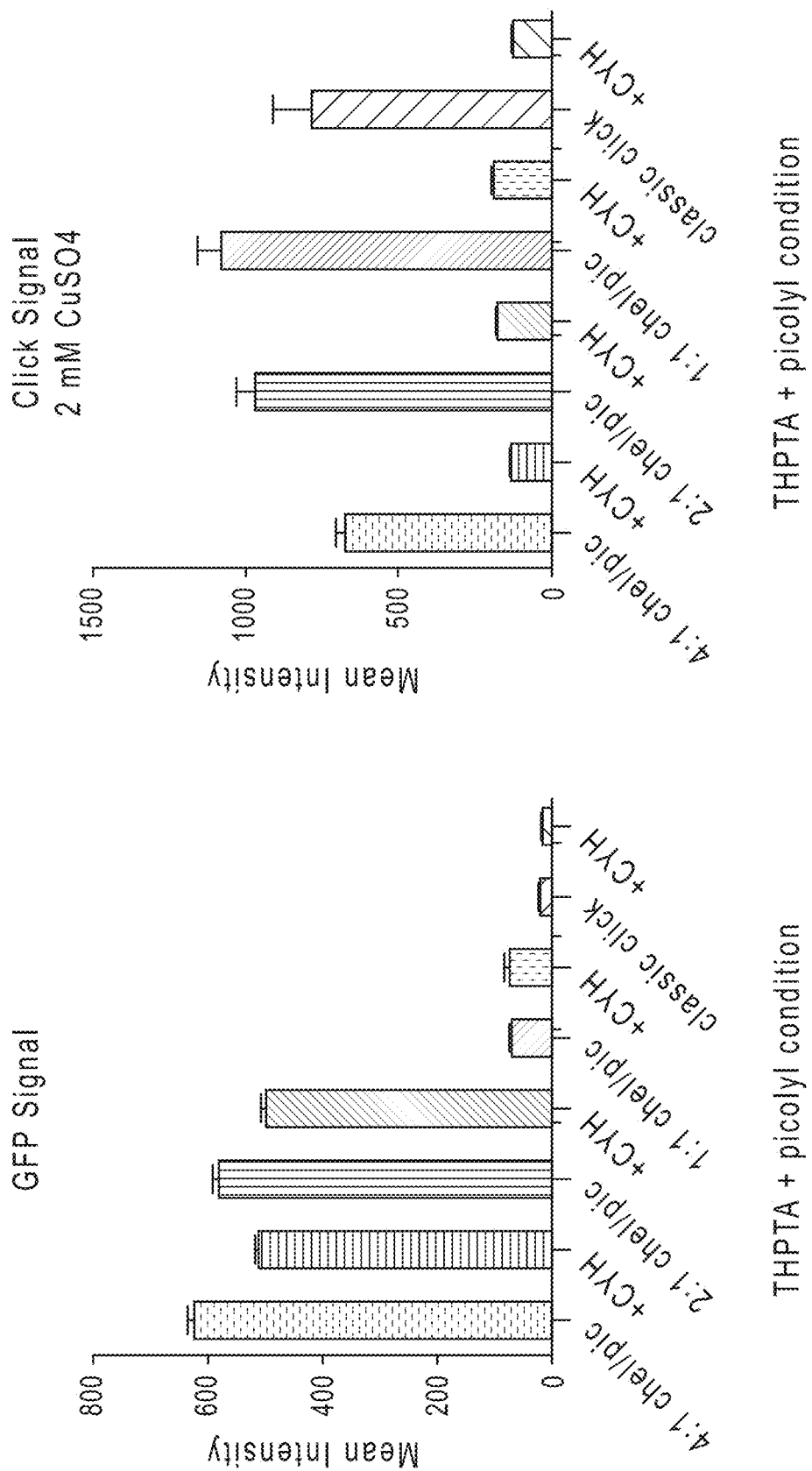
FIG. 15 shows graphical representation of GFP stability and progression of click reaction with HPG at 2 mM copper as described in Example 7.
Figure 16:
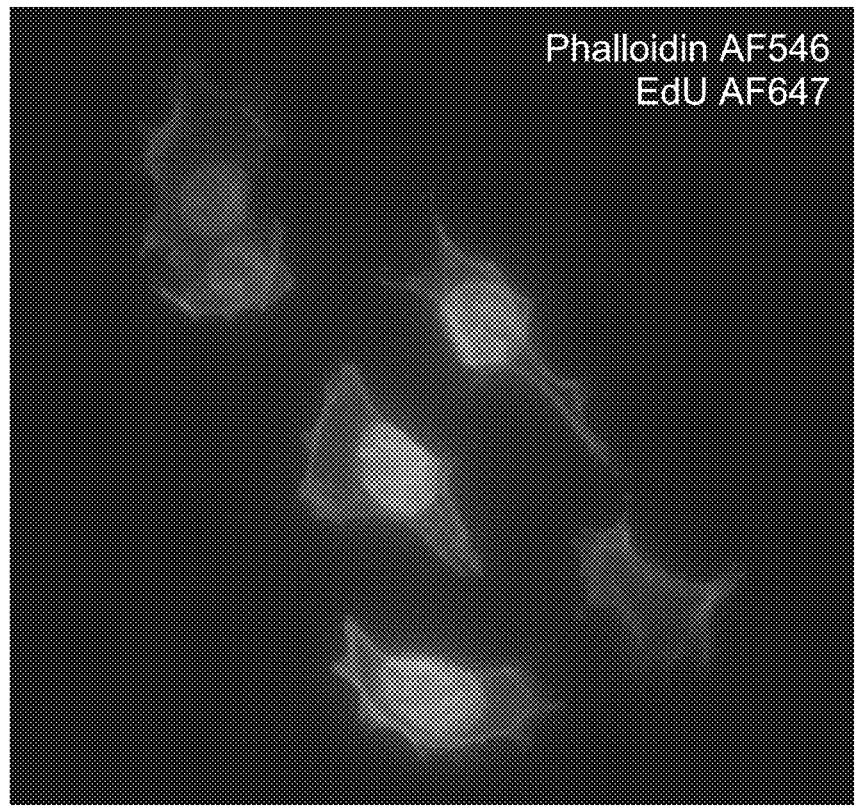
FIG. 16 shows shows Click Labeling of HPG with AF647-picolyl azide followed by phalloidin staining in presence of GPF with THPTA as described in Example 8.
Figure 17:
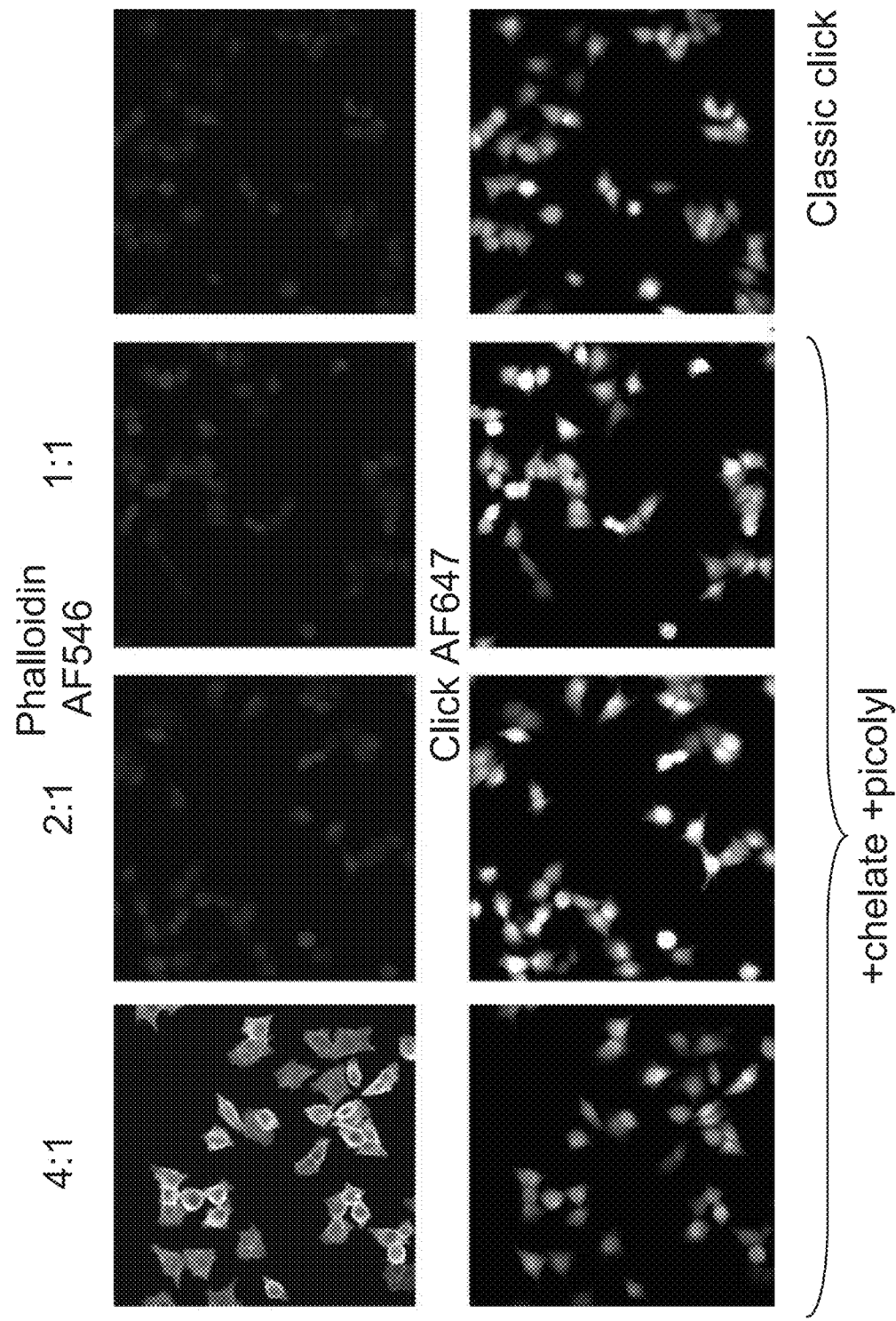
FIG. 17 shows click Labeling of HPG with AF647-picolyl azide or AF647 azide in presence of GPF with THPTA as ligand with various molar ratio of Cu:THPTA as described in Example 8.

To determine whether the GFP degradation would be significant during the time frame for completing a click reaction, click reactions between Oregon Green® ("OG") alkyne and QSY-azide were carried under the same four conditions (plus a copper-less control) described above. As shown in FIG. 7B, the click reactions in the presence of THPTA and low copper, which resulted in the least degradation of GFP signal in FIG. 7A, were the fastest. At the lowest concentration of Cu(II) with THPTA (0.125 mM Cu(II) plus 0.5 mM THPTA and 10 mM sodium ascorbate), the click reaction was complete in about 20 minutes, at which time the GFP signal was still about 95% of maximum (see FIG. 7A). These results show that copper-catalyzed click reactions can be carried out in biological systems without significant protein degradation.

Example 6

General Procedure for EU Labeling of RNA in Cells: A375 Cells Stably Transfected with GFP Expressing Erk2 are Plated Overnight at 5000 Cells/Well Cell Density.

Human malignant melanoma (A375) cells expressing Erk2-GFP (Life Technologies) were cultured in L-glutamine-containing Dulbecco's modified Eagle Medium (Life Technologies) supplemented with 10% v/v fetal bovine serum (Life Technologies), non-essential amino acids (Life Technologies), and 5 µg/mL blasticidin. All cells were maintained at 37° C. under 5% CO$_2$.

These cells are pulse with 200 µM 5-ethynyl uridine (EU) for 1 hour followed by fixation with 3.7% formalin in PBS for 15 minutes. The cells are then washed twice with 3% BSA in PBS followed by permeabilization with 0.5% Triton in PBS for 20 minutes. The permeabilized cells were washed twice with 3% BSA in PBS. Click reaction was carried out for 1 hr at RT followed by washing the cells twice with 3% BSA in PBS and rinsed twice with PBS. The click conditions were combinations of with or without chelate and AF647-picolyl azide or AF647-azide. The clicked cells were then stained with Hoechst stain (1 ug/mL in PBS) for 30 min at RT followed by three times washing with PBS. The cells were imaged on ArrayScan.

Example 7

General Procedure for HPG Labeling of Proteins in Cells.

A375 cells stably transfected with GFP expressing Erk2 are plated overnight at 5000 cells/well cell density.

These cells were pulse with with 50 µM L-homopropargylglycine (HPG) for 1 h in presence or absence of 40 µM cycloheximide followed by fixation with 3.7% formalin in PBS for 15 minutes. The cells are then washed twice with 3% BSA in PBS followed by permeabilization with 0.5% Triton in PBS for 20 minutes. The permeabilized cells were washed twice with 3% BSA in PBS. Click reaction was carried out for 1 hr at RT using 2 mM $CuSO_4$ and 10 mM Sodium Ascorbate, followed by washing the cells twice with 3% BSA in PBS and rinsed twice with PBS. The click reactions were carried out following combinations of chelate, Cu and AF647-picolyl azide or AF647-azide.
a. 4:1 chelate/copper+picolyl azide
b. 2:1 chelate/copper+picolyl azide
c. 1:1 chelate/copper+picolyl azide
d. No chelate NO picolyl=Classic click The clicked cells were then stained with Hoechst stain (1 ug/mL in PBS) for 30 min at RT followed by three times washing with PBS. The cells were imaged on ArrayScan.

Example 8

General Procedure for Labeling with Phalloidin AF546 after Click HPG Labeling of Proteins in Cells.

A375 cells stably transfected with GFP expressing Erk2 are plated overnight at 5000 cells/well cell density. Prior to incubation with HPG containing medium, cells were washed once with DPBS with calcium and magnesium, then grown in methionine-free DMEM (Life Technologies) for 30 mM. These cells were pulsed with 50 µM HPG for 1 hr in presence or absence of 40 µM cycloheximide followed by fixation with 3.7% formalin in PBS for 15 minutes. The cells are then washed twice with 3% BSA in PBS followed by permeabilization with 0.5% Triton in PBS for 20 minutes. The permeabilized cells were washed twice with 3% BSA in PBS. Click reaction was carried out for 1 hr at RT using 2 mM $CuSO_4$ and 10 mM Sodium Ascorbate, followed by washing the cells twice with 3% BSA in PBS and rinsed twice with PBS. The click reactions were carried out using 4:1 chelate/copper and AF647-picolyl azide The clicked cells were then stained with Phalloidin-AF546 (30 mM at rt) conjugate followed by Hoechst stain (1 ug/mL in PBS) for 30 mM at RT followed by three times washing with PBS. The cells were imaged on ArrayScan.

FIGS. 13 through 17 further illustrate the generality of the use of chelation-assisted copper (I)-catalyzed azide-alkyne cycloaddition using picolyl azides to label metabolically alkynes in proteins and found much higher detection sensitivity compared without chelation assistance.

Example 9

Figure 18:
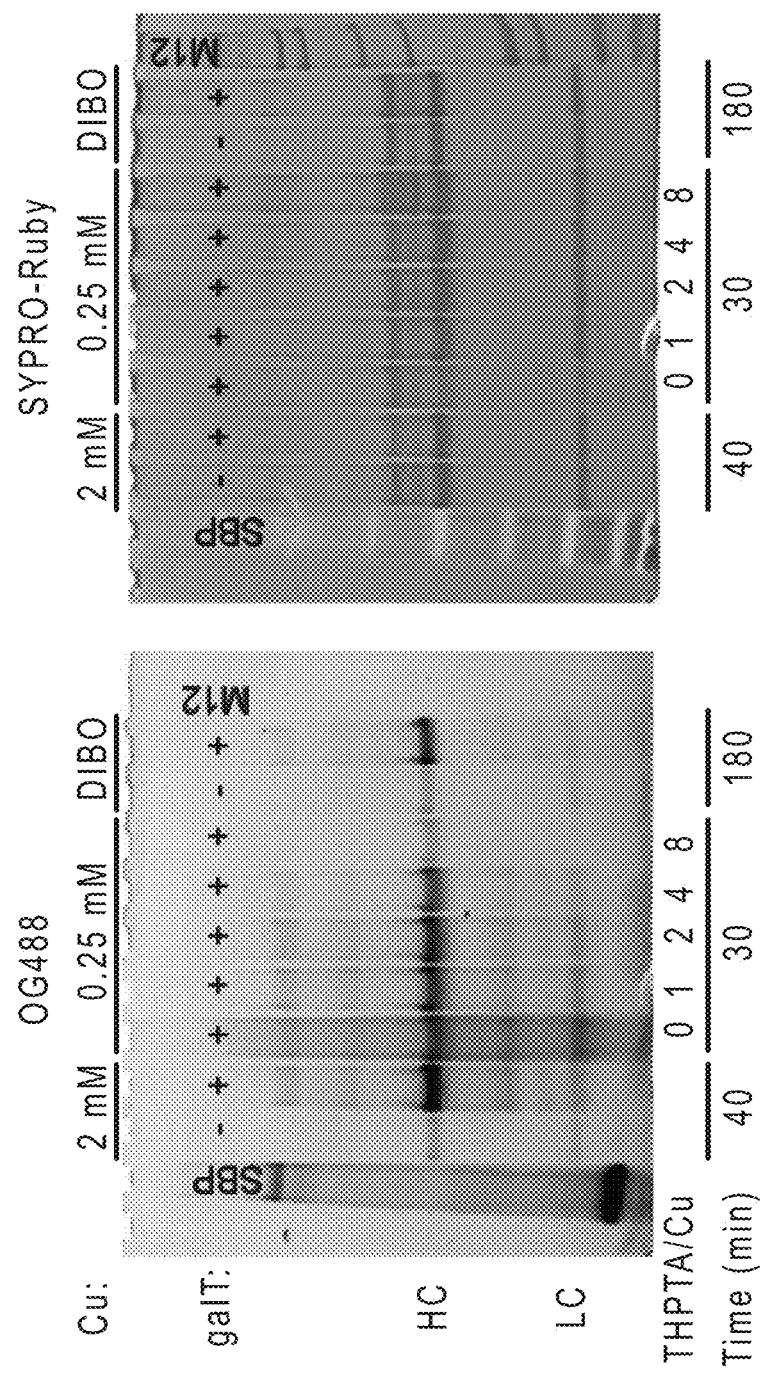
FIG. 18 shows a SDS-PAGE gel GalNAz-labeled monoclonal anti-TSH click reacted with either DIBO or click reacted THPTA/Picolyl, where in the latter the THPTA is varied with respect to the Cu concentration.

Monoclonal antibody anti-TSH was modified at its GlcNAc sites with UDPGalNAz using galactoyltransferase. The GalNAz groups were then click reacted either with the standard click reaction using BCS, with DIBO click reaction or with THPTA/Picolyl click reaction. Cu 2 mM is the original Cu Click reaction with 2 mM Cu+10 mM Ascorbate for 4 mM, followed by addition of 10 mM BCS with incubation for 30 mM. THPTA/Picolyl click reactions were carried out with 0.25 mM Cu, supplemented with THPTA at a molar ratio of 0:1, 1:1, 2:1, 4:1, and 8:1 for 40 minutes in the presence of 10 mM ascorbate. For all Cu containing reactions 10 µM picolyl Oregon green alkyne was used. DIBO click reactions were carried out with DIBO-Oregon Green 488 at 20 µM for 3 h. In FIG. 18, samples of control antibodies are indicated with galT-(no galactosyltransferase was added in the GalNAz modification step). SBP (See-Blue® Plus 2 Pre-Stained Standard; LC5925) and M12 (Mark 12™ Unstained Standard; LC5677) were used as molecular weight standards. Gels were imaged with a FUJI-FILM FLA-9000 for fluorescence detection for 488 nm dyes followed by SYPRO® Ruby General Protein Stain.

Example 10

Figure 19:
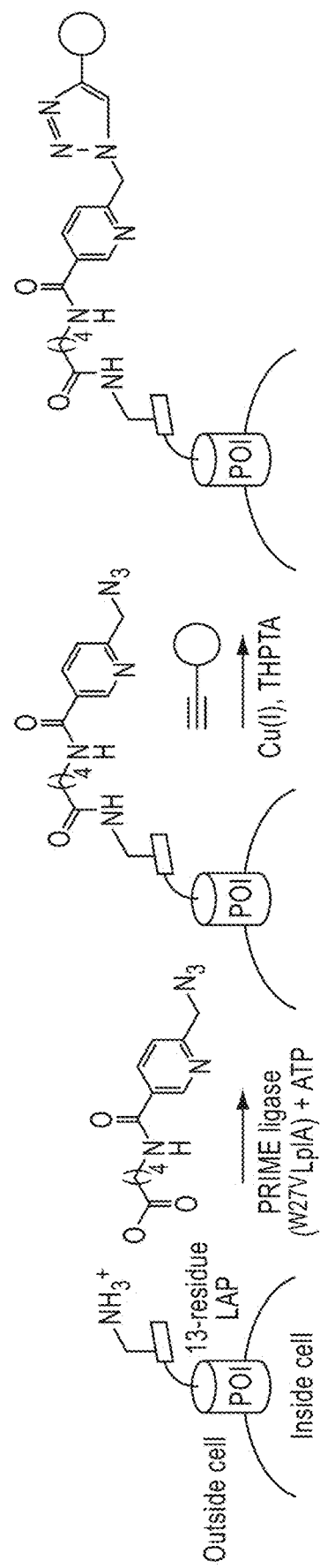
FIG. 19 shows the ligation of a picolyl azide derivative bearing a carboxylate terminal onto recombinant proteins expressed on the surface of living mammalian cells, as described in Example 10.

Site Specific Labeling of Cell Surface Proteins with an Engineered Picolyl Azide Ligase and Chelation-Assisted Copper(I)-Catalyzed Azide-Alkyne Cycloaddition The picolyl azide structure was converted into a substrate (for example, 5-(6-(azidomethyl)nicotinamido)pentanoic acid as shown below) for lipoic acid ligase, an *Escherichia coli* enzyme useful for site-specific protein labeling in cells. The data showed that the W37V mutant of *E. coli* lipoic acid ligase (Lp1A) was found to efficiently catalyze the ligation of a picolyl azide derivative bearing a carboxylate terminal onto recombinant proteins expressed on the surface of living mammalian cells as shown in FIG. 19. The ligated picolyl azide was then chemoselectively derivatized with various alkyne-fluorophores, under extremely mild conditions with 50 µM copper, in high yield and with minimal observable cytotoxicity, even on living neurons. A side-by-side comparison of our chelation-assisted copper(I)-catalyzed azide-alkyne cycloaddition protocol for specific protein labeling on the cell surface, against an analogous labeling protocol with alkyl azide followed by chelation-assisted copper(I)-catalyzed azide-alkyne cycloaddition showed that the former gives a 9-fold higher signal, with minimal background, after only 5 min of labeling (for the second step).

Synthesis of
5-(6-(azidomethyl)nicotinamido)pentanoic acid

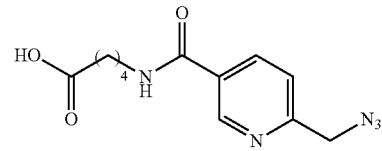

To a solution of 6-azidomethylnicotinic acid (30 mg, 0.168 mmol; from Example 4) in anhydrous DMF (500 µL) was added disuccinimidyl carbonate (DSC; 65 mg, 0.253 mmol) and triethylamine (TEA; 120 µL, 0.840 mmol). The reaction was allowed to proceed for 3 hours at ambient temperature. The reaction mixture was diluted with chloroform and water. Layers were separated, and the aqueous layer was extracted with chloroform three times. The combined organic layer was washed with brine, dried over $MgSO_4$, and concentrated in vacuo. The residual mixture was purified by silica chromatography (1:1 hexanes:ethyl acetate) to afford the succinimidyl ester of 6-azidomethylnicotinic acid. Rf=0.67 in 9:1 chloroform:methanol.

To a solution of 5-azidomethylnicotinic acid succinimidyl ester (15 mg, 0.055 mmol) in anhydrous DMF (500 µL) was added 5-aminovaleric acid (32 mg, 0.273 mmol) and TEA (38 µL, 0.273 mmol). The reaction proceeded for 12 hours at ambient temperature. TEA and DMF were then removed in vacuo, and the resulting residue was dry-loaded in 9:1 chloroform:methanol onto a silica column, and purified using 9:1 chloroform:methanol as eluent. Rf=0.19 in 9:1 chloroform:methanol. $^1$H NMR (D$_2$O, 500 MHz): 8.83 (s, 1H), 8.18 (d, 1H, J=8.5 Hz), 7.59 (d, 1H, J=8 Hz), 4.62 (s, 2H), 3.42 (m, 2H), 2.32 (m, 2H), 1.65 (m, 4H).

In Vitro Lp1A-Catalyzed Picolyl Azide Ligation for Preparation of a LAP-Picolyl Azide Adduct.

Figure 20:
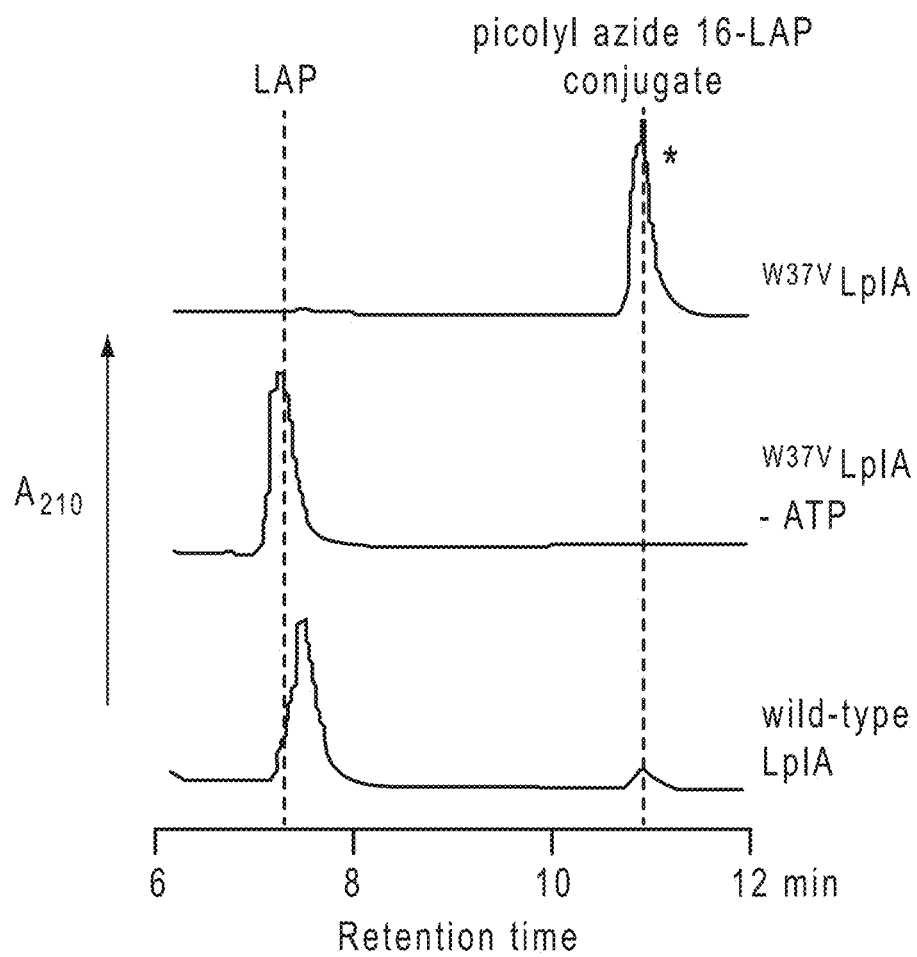
FIG. 20 shows the HPLC analysis of $^{W37V}$Lp1A-catalyzed ligation of picolyl azide (5-(6-(azidomethyl)nicotinamido) pentanoic acid) onto LAP peptide, as described in Example 10.

The enzymatic reaction was assembled as follows: 150 μM LAP (amino acid sequence: GFEIDKVWYDLDA), 5 μM W37VLp1A, 500 μM 5-(6-(azidomethyl) nicotinamido) pentanoic acid, 1 mM ATP, and 5 mM Mg(OAc)2 in 20% v/v glycerol in Dulbecco's phosphate-buffered saline (DPBS) at 30° C. for 30 min. The reaction was quenched with EDTA (final concentration 50 mM) to give the LAP-picolyl azide adduct and analyzed on a Varian Prostar HPLC using a reverse phase C18 Microsorb-MV100 column (250×4.6 mm). Chromatograms were recorded at 210 nm. A 10-min gradient of 30-60% acetonitrile in water with 0.1% trifluoroacetic acid at a flow rate of 1 mL/min was used. FIG. 20 shows these chromatograms. LAP had a retention time of 7.5 min; after ligation to the picolyl azide, the retention time increased to 11 min. The data showed that the W37V1p1A catalyzes the attachment of the picolyl azide to LAP.

Cell Culturing.

Human embryonic kidney (HEK) cells were cultured in minimal essential medium (MEM, Mediatech) supplemented with 10% v/v fetal bovine serum (PAA Laboratories).

For hippocompal neuron cultures, Spague Dawley rat pups were sacrificed at embryonic day 18. Hippocampal tissue was digested with papain (Worthington) and DNaseI (Roche) and plated on glass coverslips pretreated with poly-D-lysine (Sigma) and mouse laminin (Life Technologies) in L-glutamine-containing MEM (Sigma) supplemented with 10% v/v fetal bovine serum (PAA Laboratories) and B27 (Life Technologies). At 3 days in vitro, half of the growth medium was replaced with Neurobasal medium (Life Technologies) supplemented with B27 and GlutaMAX (Life Technologies).

Genetic Constructs.

Complete nucleotide sequences of the following constructs are known in the art: Lp1A variants in pYFJ16 for expression in E. coli; LAP-CFP in pDisplay; LAP-neurexin-1β in pECFP-N1; and LAP-neuroligin-1 in pNICE.

Imaging.

Fluorescence imaging. For FIGS. 21 and 22, cells were imaged in Tyrode's buffer or DPBS in epifluorescence or confocal modes. For epifluorescence imaging, we used a Zeiss AxioObserver inverted microscope with a 40× oil-immersion objective. CFP (420Y20 excitation, 425 dichroic, 475Y40 emission), Alexa Fluor® 647 (630Y20 excitation, 660 dichroic, 680Y30 emission) and differential interference contrast (DIC) images were collected and analyzed using Slidebook software (Intelligent Imaging Innovations). For confocal imaging, we used a Zeiss Axiovert 200M inverted microscope with a 40× oil-immersion objective. The microscope was equipped with a Yokogawa spinning disk confocal head, a Quad-band notch dichroic mirror (405Y488Y568Y647), and 491 (DPSS), 561 nm (DPSS), 640 nm (DPSS) lasers (all 50 mW). YFP/Alexa Fluor® 488 (491 laser excitation, 528Y38 emission), Alexa Fluor® 568 (561 laser excitation, 617Y73 emission), Alexa Fluor® 647 (640 laser excitation, 680/30 emission), and DIC images were collected using Slidebook software. Fluorescence images in each experiment were normalized to the same intensity ranges. Acquisition times ranged from 10-1000 milliseconds.

General Protocol for Cell-Surface Protein Labeling with PRIME Method Followed by Chelation-Assisted Copper(I)-Catalyzed Azide-Alkyne Cycloaddition.

Human embryonic kidney (HEK) cells were transfected at ~80% confluency with expression plasmids for LAP-tagged neurexin-1β (400 ng for a 0.95 cm2 dish) and yellow fluorescent protein-tagged histone 2B protein (H2B-YFP; 100 ng) using lipofectamine 2000 (Invitrogen). 24 hr after transfection, cells were treated with 10 μM purified W37VLp1A, 200 μM 5-(6-(azidomethyl)nicotinamido)pentanoic acid made above, 1 mM ATP, and 5 mM Mg(OAc)2 in cell growth medium for 20 min at room temperature. After excess Lp1A labeling reagents had been removed by quickly replacing the medium 2-3 times, cells were further labeled with 20 μM Alexa Fluor® 647-alkyne, 50 μM CuSO4, 250 μM THPTA, and 2.5 mM sodium ascorbate in DPBS for 5 min at room temperature. Cells were immediately imaged after excess CuAAC labeling reagents were removed by 2-3 quick washes with fresh growth medium.

Figure 21:
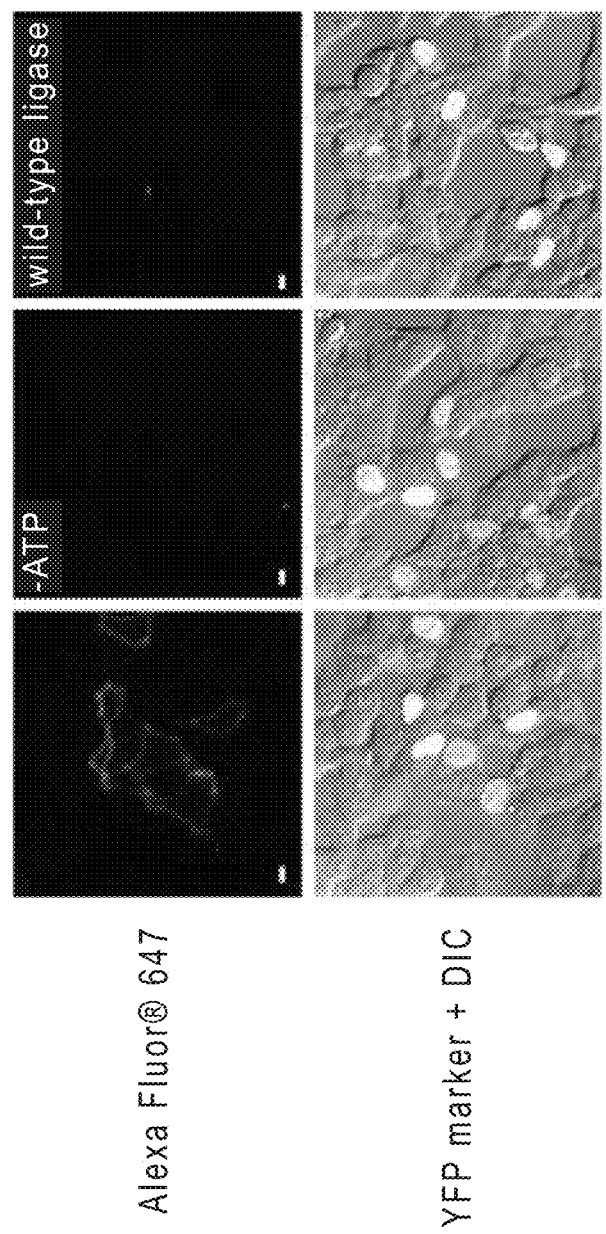
FIG. 21 shows the chelation-assisted copper(I) catalyzed azide-alkyne cycloaddition for tagging of Alexa Fluor® 647 onto neurexin in living HEK cells. Negative controls are shown with ATP omitted (second column) or wild-type Lp1A in place of $^{W37V}$Lp1A (third column). H2B-YFP is the nuclear-localized YFP transfection marker, as described in Example 10.

FIG. 21 shows the results of chelation-assisted copper(I) catalyzed azide-alkyne cycloaddition for tagging of Alexa Fluor® 647 onto neurexin in living HEK cells. Negative controls are shown with ATP omitted (second column) or wild-type Lp1A in place of $^{W37V}$Lp1A (third column). H2B-YFP is the nuclear-localized YFP transfection marker. Negative controls are shown with ATP omitted (second column) or wild-type Lp1A in place of $^{W37V}$Lp1A (third column). H2B-YFP is the nuclear-localized YFP transfection marker. Confocal images are shown. Scale bars for all images, 10 μm.

Labeling of LAP-Neuroligin-1 in Live Dissociated Neurons with PRIME Followed by Chelation-Assisted CuAAC.

Neurons were transfected at 5 days in vitro with expression plasmids for LAP-tagged neuroligin-1 (500 ng for a 1.9 cm2 dish) and green fluorescent protein-tagged Homer1b (Homer-GFP; 100 ng for a 1.9 cm2 dish) using Lipofectamine 2000, using half the amount of the manufacturer's recommended reagent quantity. Neurons were labeled at 11 days in vitro with 10 μM purified W37VLp1A, 200 μM of 5-(6-(azidomethyl) nicotinamido)pentanoic acid made above, 1 mM ATP, and 5 mM Mg(OAc)2 in preconditioned supplemented Neurobasal medium for 20 min at 37° C. After brief rinsing in supplemented preconditioned medium, neurons were further labeled with 20 μM Alexa Fluor® 647-alkyne, 50 μM Tempol, 50 μM CuSO4, 250 μM THPTA, and 2.5 mM sodium ascorbate in Tyrode's buffer for 5 min at room temperature. The labeling solution was then replaced with supplemented Neurobasal medium containing 500 μM bathocuproin sulfonate, which was incubated with neurons for 30 sec. Neurons were imaged live in Tyrode's buffer after 2 further washes with supplemented Neurobasal medium.

Figure 22:
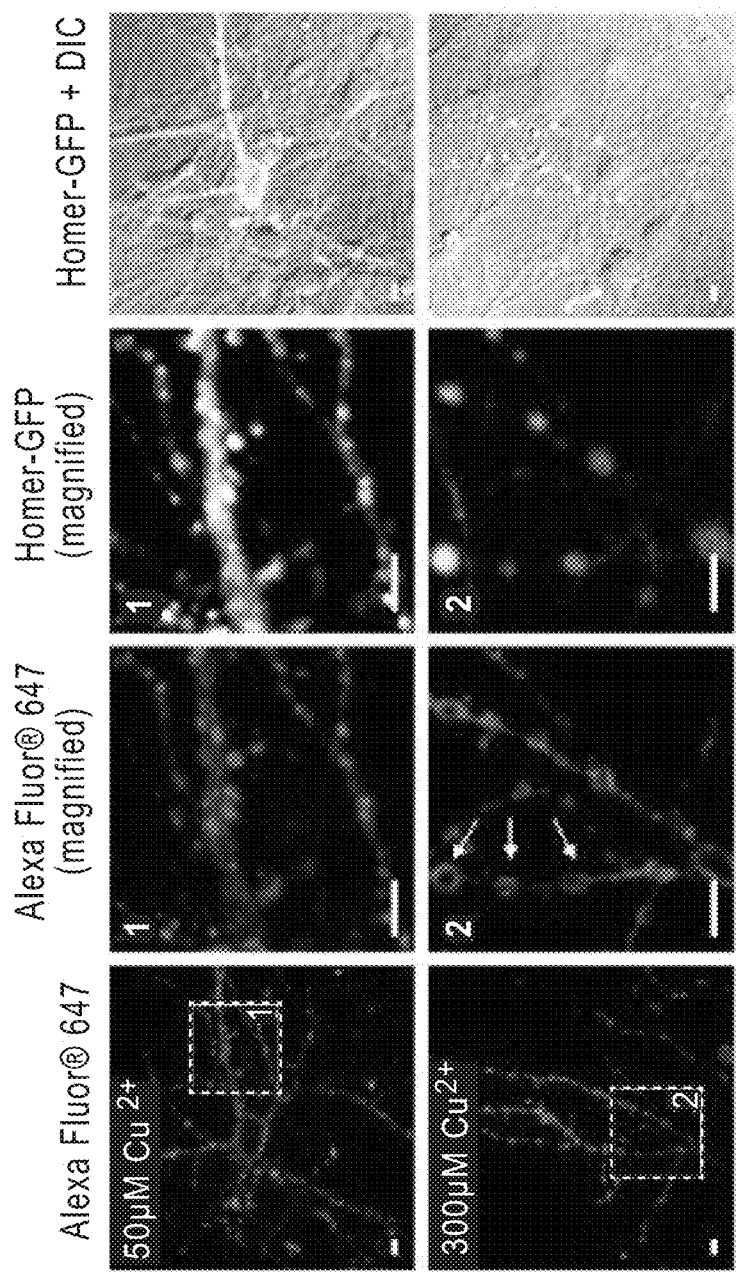
FIG. 22 shows the chelation-assisted copper(I) catalyzed azide-alkyne cycloaddition for tagging of Alexa Fluor® 647 onto neuroligin-1 in living hippocampal neurons, as described in Example 10.

FIG. 22 shows chelation-assisted copper(I) catalyzed azide-alkyne cycloaddition for tagging of Alexa Fluor® 647 onto neuroligin-1 in living hippocampal neurons. DIV11 (11 days in vitro) rat hippocampal neurons expressing LAP-neuroligin-1 and GFP-tagged Homer1b were labeled with 5-(6-(azidomethyl)nicotinamido)pentanoic acid via $^{W37V}$Lp1A, then with Alexa Fluor® 647-alkyne via chelation-assisted copper(I) catalyzed azide-alkyne cycloaddition, and imaged live after brief rinsing. Labeling conditions were the same as in the above general protocol for cell-surface protein labeling with PRIME method, except: 1) higher [CuSO$_4$] of 300 μM was used for the bottom row; 2) a radical scavenger Tempol (50 μM) was added to the CuAAC labeling solution; and 3) a biocompatible copper chelator bathocuproine sulfonate (500 μM) was used during the first rinse to immediately quench the click reaction. Alexa Fluor® 647 images in the second column correspond to the boxed regions 1 and 2, shown at higher zoom. White arrows denote regions of focal swelling when 300 μM CuSO₄ is used. Confocal images are shown. Scale bars for all images, 10 μm.

The invention claimed is:

1. A compound of the formula:

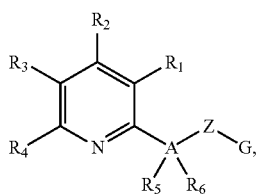

(I)

wherein:
A is a carbon;
$R_1$, $R_2$, $R_4$, $R_5$, and $R_6$, are hydrogen;
$R_3$ comprises X-L-, wherein:
X is selected from a reporter molecule, a carrier molecule, a solid support, and a reactive group, that are optionally bound to one or more additional fluorophores, wherein:
the reporter molecule comprises a chromophore, a fluorophore, a fluorescent protein, a phosphorescent dye, a tandem dye, a particle, a hapten, an enzyme, or a radioisotope;
the carrier molecule is an amino acid, a peptide, a protein, an antibody, an antibody fragment, an antigen, a polysaccharide, a nucleoside, a nucleotide, an oligonucleotide, a nucleic acid, a hapten, a psoralen, a hormone, a lipid, a lipid assembly, a tyramine, a synthetic polymer, a polymeric microparticle, a biological cell, a cellular compartment, an ion chelating moiety, an enzymatic substrate, or a virus;
the solid support is an aerogel, a hydrogel, a resin, a silica gel, a bead, a biochip, a microfluidic chip, a silicon ship, a multi-well plate, a membrane, a polymeric membrane, a particle, a derivatized plastic film, a glass bead, cotton, a plastic bead, alumina gel, polysaccharide, poly(acrylate), polystyrene, poly(acrylamide), polyol, agarose, agar, cellulose, dextran, starch, heparin, glycogen, amylopectin, mannan, inulin, nitrocellulose, diazocellulose, polyvinylchloride, polypropylene, polyethylene, nylon, latex bead, a conducting metal, a nonconducting metal, glass, magnetic bead, paramagnetic bead, superparamagnetic bead, or a magnetic support;
the reactive group is a carboxylic acid, an activated ester of carboxylic acid, an amine, a hydrazine, a haloacetamide, an alkyl halide, an isothiocynate or a maleimide group; and
L is NH—(CH₂)ₙ—NH—C(O)—, wherein n is 1 to 12;
Z is a single covalent bond; and
G is an azide.

2. The compound of claim 1, wherein the fluorophore is a xanthene, coumarin, cyanine, pyrene, oxazine, borapolyazaindacene, or carbopyranine.

3. The compound of claim 1, wherein the enzyme is horseradish peroxidase, alkaline phosphatase, beta-galactosidase, or beta-lactamase.

4. A method of modifying a biomolecule comprising the step of reacting in a solution a biomolecule comprising an azide reactive moiety with a compound of claim 1 to provide a modified biomolecule.

5. The method of claim 4, wherein the azide reactive moiety comprises a terminal alkyne, an activated alkyne, or triarylphosphine.

6. The method of claim 4, wherein the biomolecule is a nucleic acid, oligonucleotide, protein, peptide, carbohydrate, polysaccharide, glycoprotein, lipid, hormone, drug, or prodrug.

7. The method of claim 4, wherein the solution further comprises copper ions.

8. The method of claim 7, wherein the method further comprises at least one reducing agent.

9. The method of claim 7, wherein the method further comprises a copper chelator.

10. A kit comprising a compound of claim 1.

11. The kit of claim 10, wherein the kit further comprises a copper ion source.

12. The kit of claim 10, wherein the kit further comprises at least one reducing agent.

13. The kit of claim 10, wherein the kit further comprises a copper chelator.

14. A compound selected from the group consisting of:

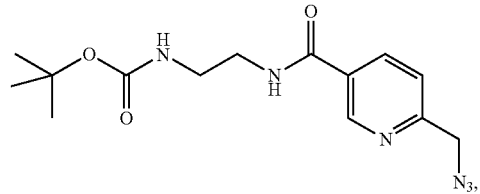

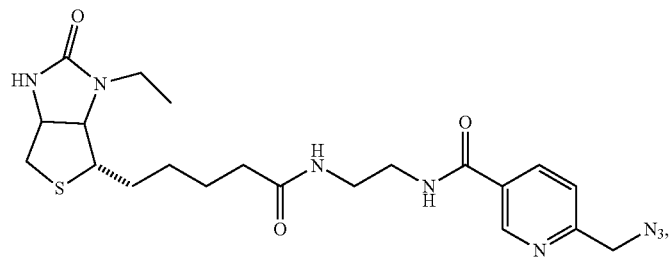

-continued
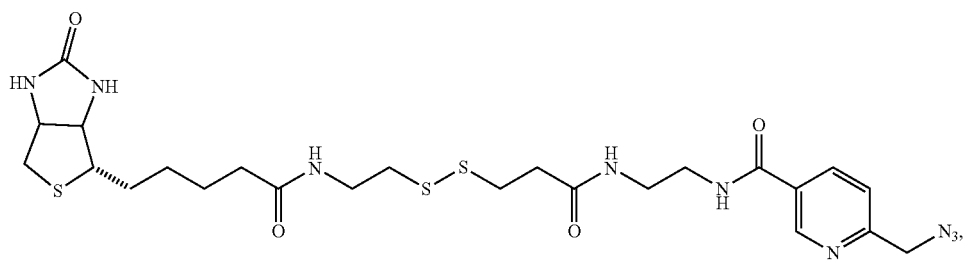
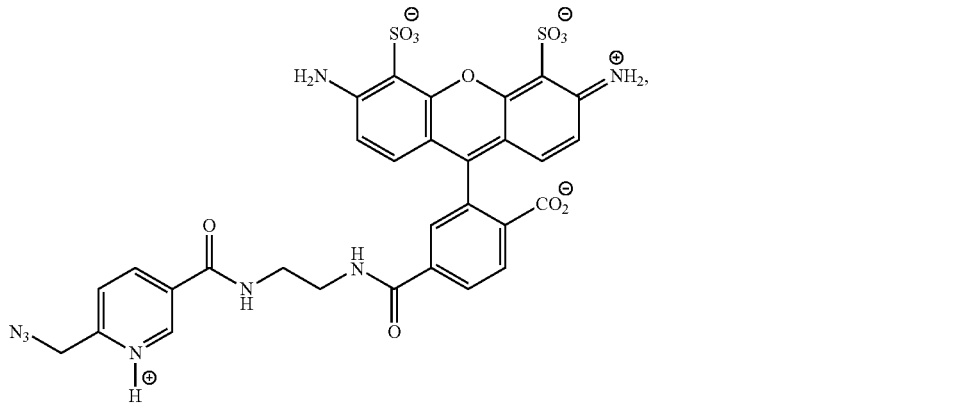
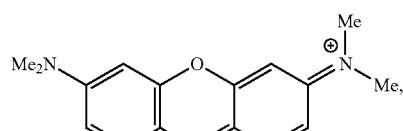
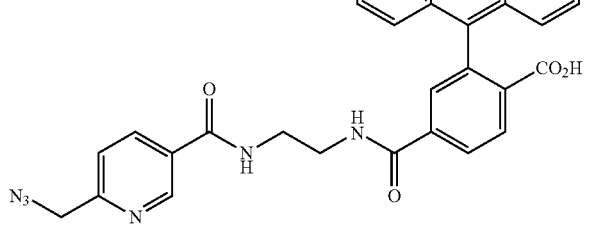
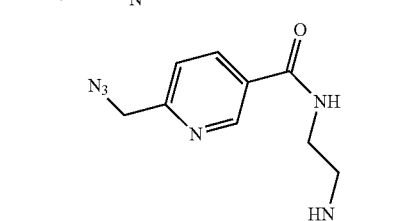
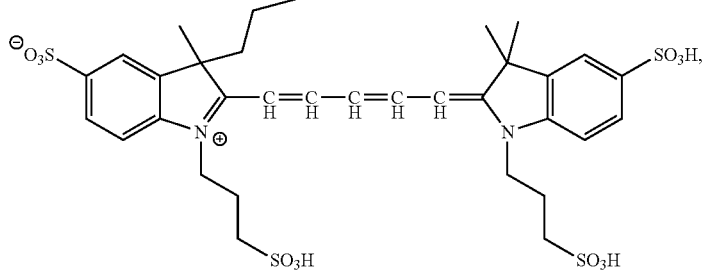

-continued
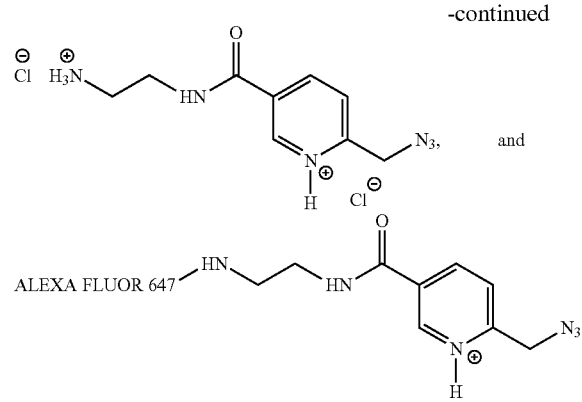
and
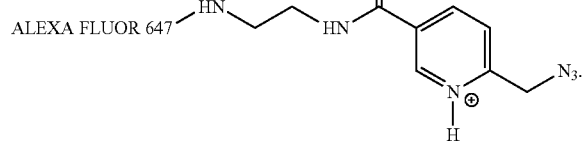
* * * * *